US008389469B2

(12) United States Patent
Yoong et al.

(10) Patent No.: US 8,389,469 B2
(45) Date of Patent: Mar. 5, 2013

(54) **BACTERIOPHAGE LYSINS FOR *BACILLUS ANTHRACIS***

(75) Inventors: Pauline Yoong, Boston, MA (US); Raymond Schuch, New York, NY (US); Daniel Nelson, Rockville, MD (US); Vincent A. Fischetti, West Hempstead, NY (US)

(73) Assignee: The Rockefeller University, New York, NY (US)

( * ) Notice: Subject to any disclaimer, the term of this patent is extended or adjusted under 35 U.S.C. 154(b) by 742 days.

(21) Appl. No.: 11/916,208

(22) PCT Filed: May 31, 2006

(86) PCT No.: PCT/US2006/021094
§ 371 (c)(1),
(2), (4) Date: Dec. 18, 2009

(87) PCT Pub. No.: WO2008/018854
PCT Pub. Date: Feb. 14, 2008

(65) Prior Publication Data

US 2010/0120673 A1 May 13, 2010

Related U.S. Application Data

(60) Provisional application No. 60/688,270, filed on Jun. 6, 2005.

(51) Int. Cl.
*A61K 38/16* (2006.01)
*A61P 31/04* (2006.01)
*C07K 14/195* (2006.01)

(52) U.S. Cl. .... 514/2.4; 514/2.3; 424/185.1; 424/246.1; 530/350

(58) Field of Classification Search ........................ None
See application file for complete search history.

(56) References Cited

U.S. PATENT DOCUMENTS

| | | | |
|---|---|---|---|
| 4,179,337 | A | 12/1979 | Davis et al. |
| 4,301,144 | A | 11/1981 | Iwashita et al. |
| 4,496,689 | A | 1/1985 | Mitra |
| 4,615,697 | A | 10/1986 | Robinson |
| 4,640,835 | A | 2/1987 | Shimizu et al. |
| 4,670,417 | A | 6/1987 | Iwasaki et al. |
| 4,680,338 | A | 7/1987 | Sundoro |
| 4,791,192 | A | 12/1988 | Nakagawa et al. |
| 4,948,580 | A | 8/1990 | Browning |
| 5,413,792 | A | 5/1995 | Ninomiya et al. |
| 5,428,130 | A | 6/1995 | Capon et al. |
| 5,554,380 | A | 9/1996 | Cuca et al. |
| 5,654,010 | A | 8/1997 | Johnson et al. |
| 5,808,022 | A | 9/1998 | Huse |
| 5,863,560 | A | 1/1999 | Osborne |
| 5,942,243 | A | 8/1999 | Shah |
| 5,976,862 | A | 11/1999 | Kauffman et al. |
| 6,056,954 | A | 5/2000 | Fischetti et al. |
| 6,056,955 | A | 5/2000 | Fischetti et al. |
| 7,402,309 | B2 | 7/2008 | Fischetti et al. |
| 7,569,223 | B2 | 8/2009 | Fischetti et al. |
| 7,582,291 | B2 | 9/2009 | Yoong et al. |
| 7,638,600 | B2 | 12/2009 | Fischetti et al. |
| 2003/0109017 | A1 | 6/2003 | Conerly et al. |
| 2005/0004030 | A1 | 1/2005 | Fischetti et al. |
| 2008/0221035 | A1 | 9/2008 | Fischetti et al. |

FOREIGN PATENT DOCUMENTS

| | | | |
|---|---|---|---|
| WO | WO 87/05330 | A1 | 9/1987 |
| WO | WO 96/07399 | A1 | 3/1996 |
| WO | WO 96/40072 | A2 | 12/1996 |
| WO | WO 97/03692 | A1 | 2/1997 |
| WO | WO2010/002959 | | 1/2010 |

OTHER PUBLICATIONS

Witkowski et al (Biochemistry 38:11643-11650, 1999).*
Seffernick et al., ( J. Bacteriol. 183(8): 2405-2410, 2001).*
Broun et al (; Science 282:1315-1317, 1998).*
International Search Report—PCT/US2006/21094—mailed on Jul. 29, 2008.
"An a-tubulin epitope peptide" (Skinner et al., J. Biol. Chem., 266: 14163-14166 (1991).
"Biological roles of two new murein hydrolases of *Streptococcus* pneumonia representing examples of module shuffling", Res. Microbiol. 151 :437-443.
"Casette mutagenesis", Wells et al., Gene, 34:315 (1985).
"Chemical cleavage",Cotton et al. (1985). Proc. Natl. Acad. Sci. USA 85:4397-4401).
"Direct DNA sequencing" (Church and Gilbert (1988). Proc. Natl. Acad. Sci. USA 81:1991-1995).
"Discrimination on the basis of electrophoretic mobility in gels with denaturing reagent" (Myers and Maniatis (1986). Cold Spring Harbor Symp. Quant. Biol. 51 :275-284).
"Enzymatic cleavage of carbohydrate moieties on polypeptides can be achieved by the use of a variety of endo- and exo-glycosidases" Thotakura et al., Meth. Enzymol., 138:350 (1987).
"*LactoBacillus* delbrueckki bacteriophage LL H lysin, and bacteriophage N11 of *Staphyloccous aureus*". (Loessner, et al., Journal of Bacteriology, Aug. 1999, p. 4452-4460).
"Restriction selection mutagenesis", Wells et al., Philos. Trans. R. Soc. London SerA, 317:415 (1986).
"Site Directed Mutagenesis", Carter et al., Nucl. Acids Res., 13:4331 (1985).
"The KT3 epitope peptide", Martin et al., Science 255:192-194 (1992).
"The ligase-mediated detection procedure", (Landegren et al., 1988).
"The lytic enzyme of the pneumococcal phage Dp-1: a chimeric enzyme of intergeneric orgin", Mol. Microbial. 25:717-725.
"The Proteins", (W. H. Freeman & Co., N. Y.); Chothia, J. Mol. Biol. 150:1 (1976).
"The T7 gene 10 protein peptide tag", (Lutz-Freyermuth et al., Proc. Natl. Acad. Sci. USA, 87:6393-6397 (1990).
"The use of restriction enzymes" (Flavell et al. (1978). Cell 15:25).
Arkin and Yourvan (1992) Proc. Natl. Acad. Sci. USA 89:7811-7815.

(Continued)

*Primary Examiner* — Padma V Baskar
(74) *Attorney, Agent, or Firm* — Klauber & Jackson LLC

(57) ABSTRACT

The present disclosure relates to methods, compositions and articles of manufacture useful for the treatment of *Bacillus anthracis* and *B. cereus* bacteria and spores, and related conditions. The disclosure further relates to compositions comprising various phage associated lytic enzyme that rapidly and specifically detect and kill *Bacillus anthracis* and other bacteria. Related articles of manufacture, methods of degrading spores and methods of treatment of infections or bacteria populations of, or subjects exposed to or at risk for exposure to *Bacillus anthracis* are also provided.

15 Claims, 18 Drawing Sheets

OTHER PUBLICATIONS

Athamna, A., M. Athamna, N. Abu-Rashed, B. Medlej, D. J. Bast, and E. Rubinstein. 2004. "Selection of *Bacillus anthracis* isolates resistant to antibiotics", J. AntimicroB. Chemother. 54:424-428.
Ausubel et al., "Current Protocols in Molecular Biology", Wiley Interscience Publishers, (1995).
Bolton and McCarthy (1962). Proc. Natl. Acad. Sci. USA 48:1390.
Bonner et al. (1973). J. Mol. Biol. 81:123.
Broudy, T.and V. A. Fischetti. 2003. "In vivo lysogenic conversion of Tox-*Streptococcus* pyogenes to Tox+ with lysogenic *streptococci* or free phage". Infect. Immun. 71 :3782-3786.
Brown, E. R. & Cherry, W. B. "Specific identification of *Bacillus anthracis* by means of a variant bacteriophage," J Infect Dis 96, 34-9 (1955).
Bryskier, A. 2002. "*Bacillus anthracis* and antibacterial agents", Clin. Microbiol. Infect. 8:467-478.
Cheng, Q., D. Nelson, S. Zhu, and V. A. Fischetti. 2005. "Removal of group B *streptococci* colonizing the vagina and oropharynx of mice with a bacteriophage lytic enzyme", AntimicroB. Agents Chemother. 49:111-117.
Choe, C. H., S. S. Bouhaouala, I. Brook, T. B. Elliott, and G. B. Knudson. 2000. "In vitro development of resistance to ofloxacin and doxycycline in *Bacillus anthracis* Sterne", AntimicroB. Agents Chemother. 44:1766.
Cleland, "Design and Production of Single Immunization Vaccines Using Polylactide Polyglycolide Microsphere Systems." in Vaccine Design: The Subunit and Adjuvant Approach, Powell and Newman, eds, (Plenum Press: New York, 1995), pp. 439-462.
Cunningham and Wells, Science. 244: 1081-1085 (1989).
D.H. Duckworth, P.A. Gulig, "Bacteriophages: Potential treatment for bacterial infections," BioDrugs, 16(1), 57-62 (2002).
Davis et al., "Basic Methods in Molecular Biology", (1986).
Delgrave et al. (1993) Protein Engineering 6(3):327-331).
Diaz et al. Proc. Natl. Acad. Sci. U.S.A., 87:8125 (1990).
Edge et al., Anal. Biochem., 118:131 (1981).
EMBL Submission Q81PJ7, 01_BACAN, Jun. 2003. Retrieved from the internet: <URL:http://www.ebi.ac.uk/cgi-bin/dbfetch?db=uniprot&id=Q81PJ7__BACAN&style=raw>.
Evan et al., "Molecular and Cellular Biology", 5:3610-3616 (1985).
Field et al., Mol. Cell. Biol., 8:2159-2165 (1988).
Fischetti, V. A. 2001. "Phage antibacterials make a comeback". Nature Biotechnol. 19:734-735.
Fischetti, V. A. 2003. "Novel method to control pathogenic bacteria on human mucous membranes", Ann. N. Y. Acad. Sci. 987:207-214.
Garcia et al., "Gene", 86: 81-88 (1990).
Garcia et al., "Streptococcal Genetics"(J.J. Ferretti and Curtis eds., (1987).
Garcia et al., Proc. Natl. Acad. Sci. USA 85: 914-918 (1988).
Gebeyehu et al., Nucleic Acids Res. 15:4513-4534 (1987).
H .W. Ackermann, et al., "New *Bacillus* bacteriophage species," Archives of Virology, 135(3-4), 333-344 (1994).
Hakimuddin, et al., Arch. Biochem. Biophys., 259:52 (1987).
Helgason, E., O. A. Okstad, D. A Caugant, H. A Johansen, A Fouet, M. Mock, I. Hegna, and A-B. Kolsto. 2000. "*Bacillus anthracis, Bacillus cereus*, and *Bacillus thuringiensis*—one species on the basis of genetic evidence". Appl. Environ. Microbiol. 66:2627-2630.
Hopp et al., "BioTechnology", 6:1204-1210 (1988).
Hora et al., Bio/Technology. 8:755-758 (1990).
HW. Ackerman, M.S. Dubrow, "Viruses of prokaryotes: General properties of bacteriophages", Boca Raton, FL, CRC Press, Inc. (1989).
Ike et al. (1983) Nucleic Acid Res. 11:477.
Itakura et al. (1984) Science 198:1056.
Jado, I., R. Lopez, E. Garcia, A. Fenoll, J. Casal, and P. Garcia. 2003. "Phage lytic enzymes as therapy for antibiotic-resistant *Streptococcus pneumoniae* infection in a murine sepsis model", J. AntimicroB. Chemother. 52:967-973.
Johnson et al., Nat. Med., 2:795-799 (1996).
Koehler, T. M. 2000. "*Bacillus anthracis"*, p. 519-528.
Lewin "Genes V" Oxford University Press Chapter 1, pp. 9-13 (1994).
Loeffler, J. M., D. Nelson, and V, A. Fischetti. 2001. "Rapid killing of *Streptococcus pneumoniae* with a bacteriophage cell wall hydrolase", Science. 294:2170-2172.
Loeffler, J. M., S. Djurkovic, and V. A. Fischetti. 2003. "Phage lytic enzyme Cpl-1 as a novel antimicrobial for pneumococcal bacteremia", Infect. Immun. 71 :6199-6204.
Loessner, M., G. Wend linger, and S. Scherer. 1995. "Heterogeneous endolysins in Listeria monocytogenes bacteriophages: a new class of enzymes and evidence for conserved holin genes within the siphovirallysis cassettes. Mol. Microbial", 16:1231-1241.
Loessner, M., K. Kramer, F. Ebel, and S. Scherer. 2002. "C-terminal domains of Listeria monocytogenes bacteriophage murein hydrolases determine specific recognition and high-affinity binding to bacterial cell wall carbohydrates". Mol. Microbial. 44:335-349.
Loessner, M., S. K. Maier, H. DaubekPuza, G. Wendlinger, and S. Scherer. 1997. "Three *Bacillus cereus* bacteriophage endolysins are unrelated but reveal high homology to cell wall hydrolases from different bacilli. J. Bacterial", 179:2845-2851.
Lopez et al., FEMS Microbiol. Lett. 100: 439-447 (1992).
Lopez, R., E. Garcia, P. Garcia, and J. L. Garcia. 1997. "The pneumococcal cell wall degrading enzymes: a modular design to create new lysins?" MicroB. Drug Resist. 3:199-211.
Lopez, R., M. P. Gonzalez, E. Garcia, J. L. Garcia, and P. Garcia. 2000, Res. Microbiol. 151:437-443.
M. Chasin and R. Langer (Eds.), Biodegradable Polymers as Drul: Delivery Systems (Marcel Dekker: New York, 1990), pp. 1-41.
Mordenti, J. and Chappell, W. "The use of interspecies scaling in toxicokinetics" In Toxicokinetics and New Drug Development, Yacobi et al., Eds., Pergamon Press, New York 1989, pp. 42-96.
Narang (1983) Tetrahedron 39:3.
Navarre "Identification of a D alanyl glycine endopeptidase activity". J Bioi Chem. May 28, 1999;274:15847 56.
Nelson, D., L. Loomis, and V. A. Fischetti. 2001. "Prevention and elimination of upper respiratory colonization of mice by group a *streptococci* by using a bacteriophage lytic enzyme", Prot. Natl. Acad. Sci. USA. 98:4107-4112).
Paborsky et al., "Protein Engineering": (6):547-553 (1990).
RNase protection (Myers et al. (1985). Science 230:1242-45.
Romero et al., J. Bacteriol. 172: 5064-5070 (1990).
Ronda et al., Eur. J. Biochem. 164: 621-624 (1987).
Sambrook et al. (1989), "In Molecular Cloning: A Laboratory Manual", Cold Spring Harbor, N. Y., chapters 9 and 11.
Sanchez et al., Gene 61: 13-19 (1987).
Schuch, R., D. Nelson, and V. A. Fischetti, "A bacteriolytic agent that detects and kills *Bacillus anthracis," Nature* 418,884-889 (2002).
Stepanov, A. V., L. I. Marinin, A. P. Pomerantsev., and N. A. Staritsin. 1996. "Development of novel vaccines against anthrax in man", J. Biotechnol. 44:155-160).
Stoflet et al. Science 239:491-494, (1988).
Swartz, M. N. 2001. "Recognition and management of anthrax—an update", N. Eng. J. Med. 345:1621-1626.
T. E. Creighton, "Proteins: Structure and Molecular Properties", W. H. Freeman & Co., San Francisco, pp. 79-87 (1983).
Ticknor, L. O., A.-B. Kolsto, K. K. Hill, P. Kein, M. T. Laker, M. Tonks, and P. J. Jackson. 2001. "Fluorescent amplified fragment length polymorphism analysis of Norwegian *Bacillus cereus* and *Bacillus thuringiensis* soil isolates". Appl. Environ. Microbiol. 67:4863-4873.
Turnbull, P. C. B. 2002. "Introduction: anthrax history, disease and ecology", Curro Top. Microbiol. Immunol. 271:1-19.
Turnbull, P. C. B. Definitive identification of *Bacillus anthracis*—a review. J Appl Microbiol 87, 237-40 (1999).
Wallace et al. (1986). Cold Spring Harbor Symp. Quant. Biol. 51:257-261.
Walter, MH, Baker, DO, "Three *Bacillus anthracis* bacteriophages from topsoil," Curr Microbiol. Jul. 2003; 47(1): 55-58.
Ward and Langer et al. Proc. Natl. Acad. Sci. USA 78:6633-6637 (1981).
Wein, L. M., Y. Liu, and T. J. Leighton. 2005. "HEPA/vaccine plan for indoor anthrax remediation". Emerging Infect. Dis. 11 :69-76).
Yasuda, Biomed. Ther., 27:1221-1223 (1993).
Young, et al. Trends in Microbiology v. 8, No. 4, Mar. 2000.

Young, R. 1992. "Bacteriophage lysis: mechanism and regulation". Microbiol. Rev. 56:430-481.
Zoller et al., Nucl. Acids Res., 10:6487-6500 (1982).
Branden et al., Introduction to Protein Structure, Garland Publishing Inc., New York, p. 247, 1991.
Witkowski et al., "Biochemistry", 38:11643-11650,1999.
Seffernick et al., Journal of Bacteriology 183(8):2405-2410 (2001).
Internet exerpt entitled "Bacteriophage;" New Horizons Diagnostics Inc.; obtained at the internet address:nhdiag.com/phage.shtml; Jan. 13, 2004; two pages.
Internet excerpt entitled "*Bacillus anthracis* (spore) Lateral Flow Screening Assay," New Horizons Diagnostics Inc.; obtained at the internet address: nhdiag.com/anthrax.shtml; Jan. 13, 2004; two pages.

* cited by examiner

Figure 1 shows selected Open Reading Frames (ORFs) in Bacillis anthracis genomes PlyPH (SEQ ID NO:1),PlyG (SEQ ID NO:2), BA3767 (SEQ ID NO:3), BA2446 (SEQ ID NO: 4), BA4073 (SEQ ID NO:5) and BA3737 (SEQ ID NO:6).

SEQ ID NO: 1 PlyPH (BA2805)
MGYIVDISKWNGNINWDVAAPQLDFVIARVQDGSNYIDPLYKSYVQAMKTRNIPFGNYAFCRFI
SIADAKKEAQDFWNRGDKSATVWVADVEVKTMDDMIAGTQAFIDELRRLGAKKVGLYVGHHM
YGPFGMANVKSDFVWIPRYGGNKPAYPCDIWQYTETGNVPGIGKCDLNQLIGNKPLSWFTES
VPKQENIQAQVSKQNIIQSGAFSPYETPDVMGALTSLKMTATFILQSDGLTYFVTEPTSDTQLN
ALKSWLDRKGWWYEVK.

SEQ ID NO: 2 PlyG
MEIQKKLVDPSKYGTKCPYTMKPKYITVHNTYNDAPAENEVSYMISNNNEVSFHIAVDDKKAIQ
GIPLERNAWACGDGNGSGNRQSISVEICYSKSGGDRYYKAEDNAVDVVRQLMSMYNIPIENV
RTHQSWSGKYCPHRMLAEGRWGAFIQKVKNGNVATTSPTKQNIIQSGAFSPYETPDVMGALT
SLKMTADFILQSDGLTYFISKPTSDAQLKAMKEYLDRKGWWYEVK

SEQ ID NO: 3 BA3767
MEIRKKLVDPSKYCIKCPYTMNPEFITVHNTYNDATAENEVAYMIRNDNQVSFHIAVDDKEAVQ
GIPLERNAWHTGDGNGNGNRKSIGVEICYSLSGGDRYYKAEDNAAIVVAQLMKQYNIPIKKVR
THQSWSGKYCPHRMLAEGRWNNFIERVQNAYNGDGKVTPTLIPPSTNGTGIAYIEGNGINLRK
GLGTGYGVIRQLGKGESYEVWGQSNGWLNLGGNQWIYNDSSYIRYTGESTPTSSQSVNNGV
GIVTITADVLRVRKGPGTNYDIVKNVYQGEQYQSWGYRDGWYNVGGDQWVSGEYVKFED.

SEQ ID NO: 4 BA2446
MARYSLHAGHNSIVQGANYGNRKEHIMDRQVKDAVVAKLRALGHTVYDDTDEVGTTQAQNL
NNIVSKTNSHDVDLVVSFHLNSYDTRANGVEVLYYDQQALSAKIAAQLSKDIGWSNRGAKERK
DLYVLSNTKAPAILIELGFIDNEADMAKWNPDKIANSIVYALTGQSGGTTPPSKQNIIQSGAFSP
YETPDVMGALTSLKMTANFILQSDGLTYFISEPTSDAQLKGMTDYLDRRGWWYEVK.

SEQ ID NO: 5 BA4073
MEIRKKLVVPSKYGTKCPYTMKPKYITVHNTYNDAPAENEVNYMITNNNEVSFHVAVDDKQAI
QGIPWERNAWACGDGNGPGNRESISVEICYSKSGGDRYYKAENNAVDVVRQLMSMYNIPIEN
VRTHQSWSGKYCPHRMLAEGRWGAFIQKVKSGNVASATVTPKQNIIQTGAFSPYELPDAVGA
LKSLNMTGKAIINPEGLTYIVTDPTSDVQLQAFKEYLERKDWWYDDK.

SEQ ID NO: 6 BA3737
MICVLSSMMKKGFYNVLAASIVFSMVTIPNYSYANELDKTVTVSPDEQALKSIENHMKDEDGR
GEDKGVRNEVQGEFLVHIVKEVPLYDSSNFQKETGVRISNQVVKAEKRKGNAYYVQTSSGTG
WIQNSDGNVEVKEIHPLLSEKLIVNEETSTYSEPFASYKEENVLEPQTIQAIGQAGEWFQVKINN
EMKWIHSPSAKFEGTKASLIQGAAPIRTKYAAAMYAAPIEEKTTDIYGVPLKEMIVPKGNENIRP
GYAMNPKYITIHETDNYSVGANARNHAIYLYNQATGTEDRSASWHFTVDDKEIYQHLPLNENA
WHAGDGAEGTGNRESIAIEIAVNEDGDYNKAVENARKLAAYLMGELNIPLENVKKHQFWSGKI
CPAIMIKNNGWEPFLQGTKMYYDANHKDDITGGWYEAAIRELDKRGIMVGDGKGSYWPERLV
TRGEFANFISRSLQLPEGSSNFSDLNAAHPSLIDGINRAASAGIISGRGNGIFAPNDTIKRDEVVI
MIDRALQYKKIKGNLVPLPFSDQDLAYDKQAVQRVYGLGIVKGNENNEFMPKGSATRGESAAF
INRMLEVIESN.

Figure 2 shows Optical Density (OD) results from a 30 minute OD assay of lysates from all induced clones against B. cereus 4342. All clones were induced for 4 hours at 37°C. One hundred microliters of B. cereus 4342 suspension was mixed with an equal volume of each cell lysate with changes in optical density at 600nm monitored on an automated spectrophotometer over 30 minutes, with readings taken every 15 seconds.

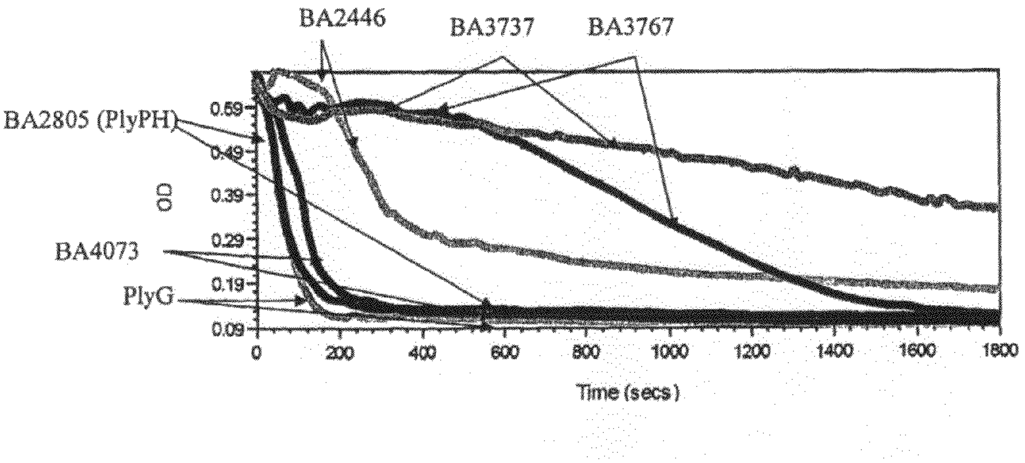

Figure 3 shows the results of purification of lysates containing PlyPH through a cation exchange column (HiTrap SP HP) with a buffer at pH 5.5 PlyPH eluted in a single protein peak centered around 210mM NaCl.
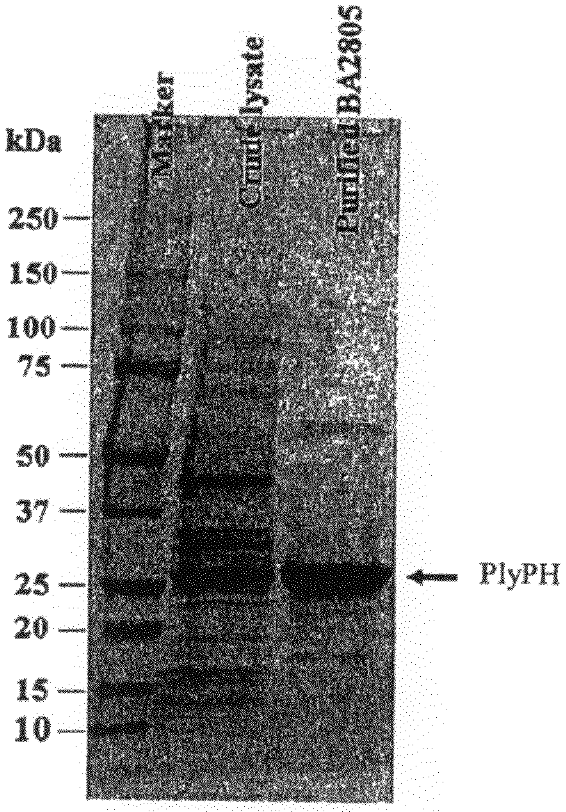

Figure 4 shows an alignment of PlyPH (SEQ ID NO:1) with Bacillus phage lysins identified in a BLAST search conducted with the PlyPH amino acid sequence (SEQ ID NO:1) as having a high degree of sequence identity to PlyPH (LambdaBa04, a lysogenic phage within B. anthracis; phBC6A52, a B. cereus phage; and Bam35c, a B. thuringiensis phage). Identical residues are highlighted by the darkest boxes, while conserved residues are not highlighted. Residues without significant conservation are highlighted by gray boxes.

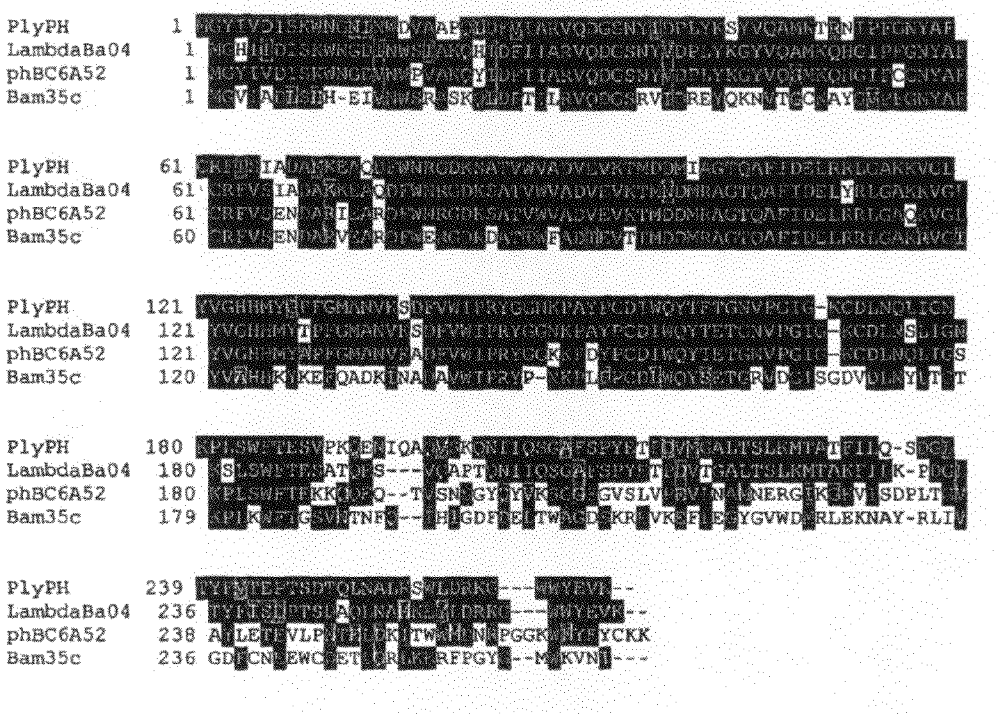

Figure 5 shows an alignment of the amino acid sequences of the phage lysins PlyPH (SEQ ID NO:1) and PlyG (SEQ ID NO:2). Identical residues are highlighted by the darkest boxes, while conserved residues are not highlighted. Residues without significant conservation are highlighted by gray boxes.

```
PlyG      1 ----MEIQKKLVDPSKYGTKCPYTMKPKYITVHNTYNDAPAENEVSYMISNNNEVSFHIA
PlyPH     1 MQYIVDISKWNGNINWDVAAPQLDFVIARVQDGSNYIDPLYKSYVQAMKTRNIPFGNYAF

PlyG     57 VDDKKAIQGIPLERNAWACGDGNGSGNRQSISVEICYSKSGG------DRYYKAEDNAVDV
PlyPH    61 CRFISIADAKKEAQDFWNRGDKSATVWVADVEVKTMDDMIAGIQAFIDELRRLGAKKVGL

PlyG    112 VRQLMSMYNIPIENVRTHQSWSGKYCPHR-------------------------MLAEG
PlyPH   121 YVGHHMYGPFGMANVKSDFVWIPRYGGNKPAYPCDIWQYTETGNVPGIGKCDLNQLIGNK

PlyG    146 RWGAFIQKVKNGNVATTSPTKQNIIQSGAFSPYETPDVMGALTSLKMTADFILQSDGLTY
PlyPH   181 PLSWKTESVPKQENIQAQVSKQNIIQSGAFSPYETPDVMGALTSLKMTATPILQSDGLTY

PlyG    206 FISKPTSDAQLKAMKEYLDRKGWWYEVK
PlyPH   241 FVIEPTSLTQLNALKSWLDRKGNWYFVK
```

Figure 6 shows the specific activities of PlyPH and PlyG obtained by incubating an equal amount of each enzyme with B. cereus 4342 in viability assays.
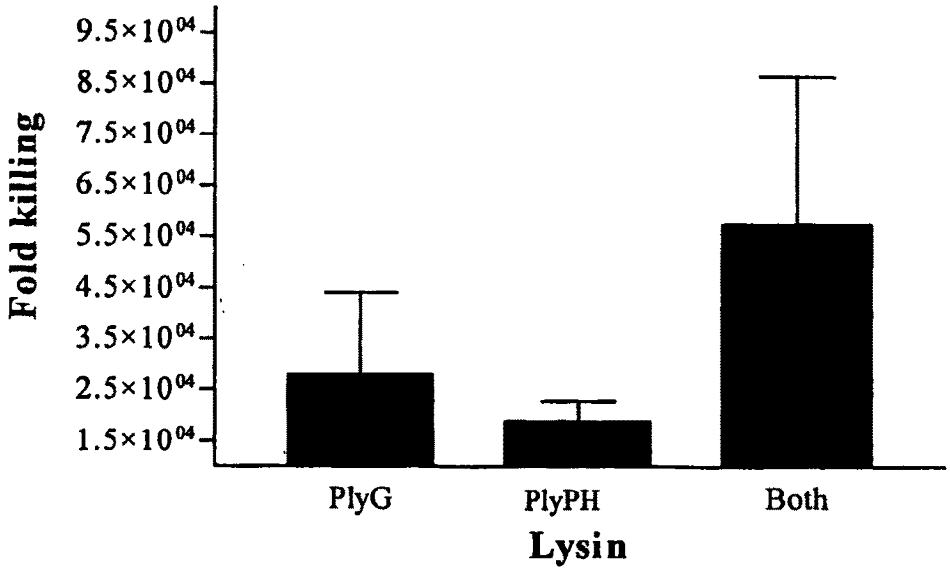

Figures 7A-D show thin section transmission electron microscopy of the bacterial cytoplasm extruding from the B. cereus 4342 cell at points of the cell wall that have been weakened by the lytic action of PlyPH (arrows). PlyPH at various concentrations were incubated with B. cereus 4342 for 1 minute, followed by the addition of a fixative to stop the reactions.
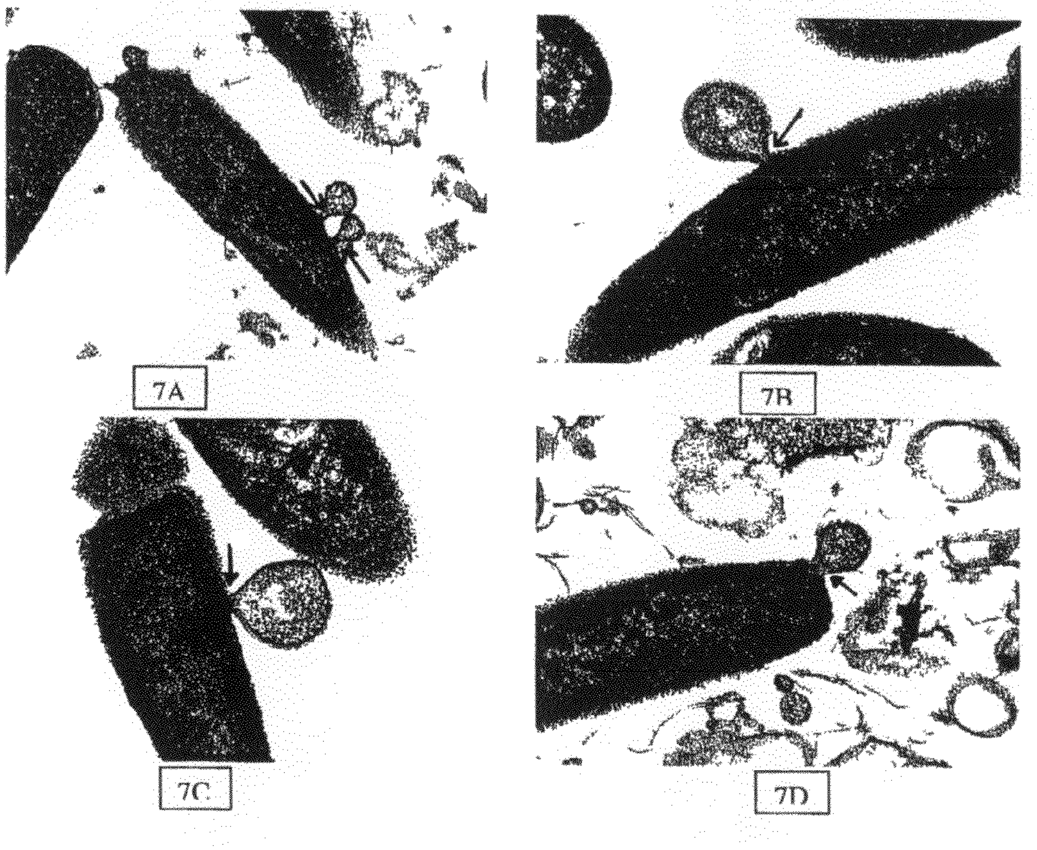

Figure 8 shows PlyPH activity against B. cereus RSVF1 tested in buffers between pH values of 2 and 12. All reactions were incubated at room temperature for 15 minutes, followed by plating on BHI agar plates for viability counts. At the end of the incubation, the pH of each reaction was rechecked with narrow range pH paper.
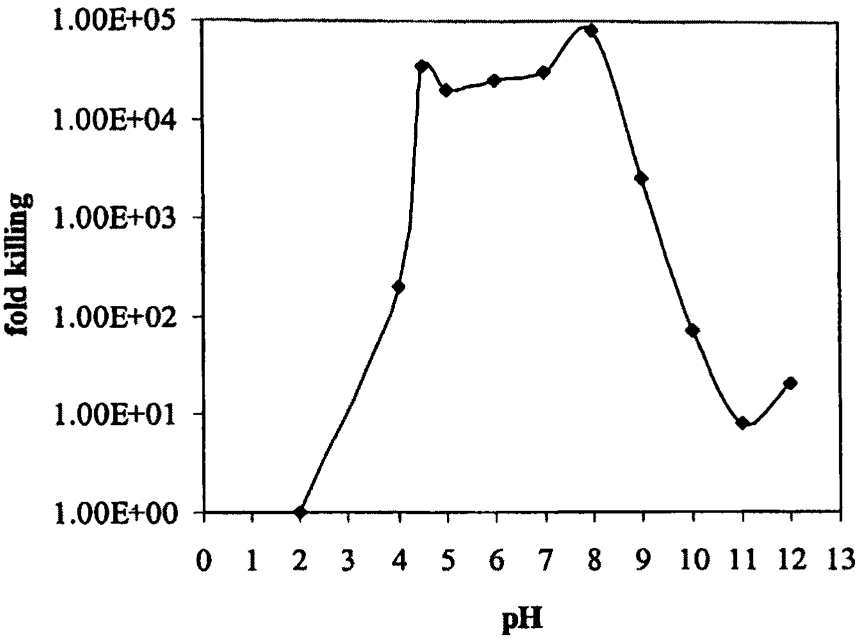

Figure 9 shows the lytic efficiency of PlyPH at a particular salt concentration measured by the decrease of B. cereus 4342 viability as compared to a parallel reaction where PBS was added instead of PlyPH. The results are represented graphically as fold killing of B. cereus 4342. Various amounts of a 5M sodium chloride stock solution was added to B. cereus RSVF1-PlyPH lytic assays, with lytic effects measured by 15 minute viability assays. A control reaction with no sodium chloride added was also measured, in addition to reactions with NaCl added to 50mM, 200mM and 500mM.

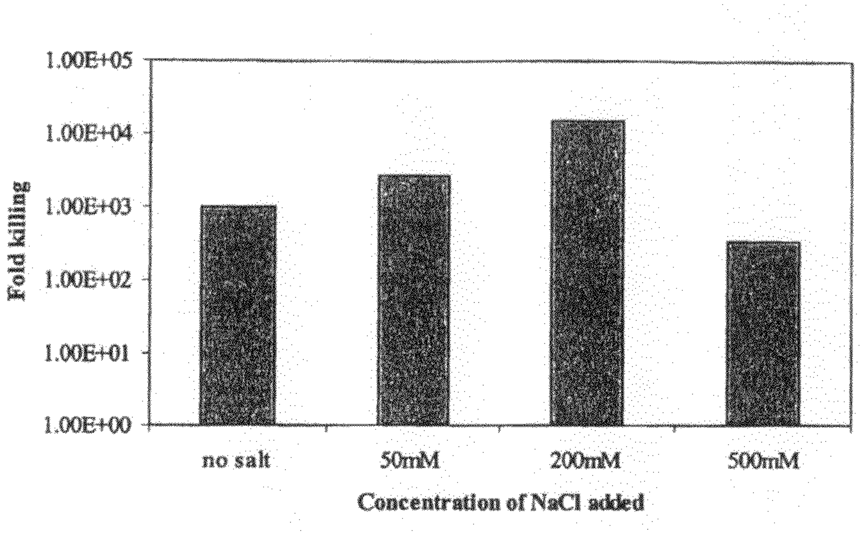

Figure 10 shows the lytic activity of PlyPH against B. cereus strain 4342 in 15 minute activity assays when the PlyPH is incubated at temperatures between 4°C and 60°C for 1 hour prior to exposure to the B. cereus strain 4342.
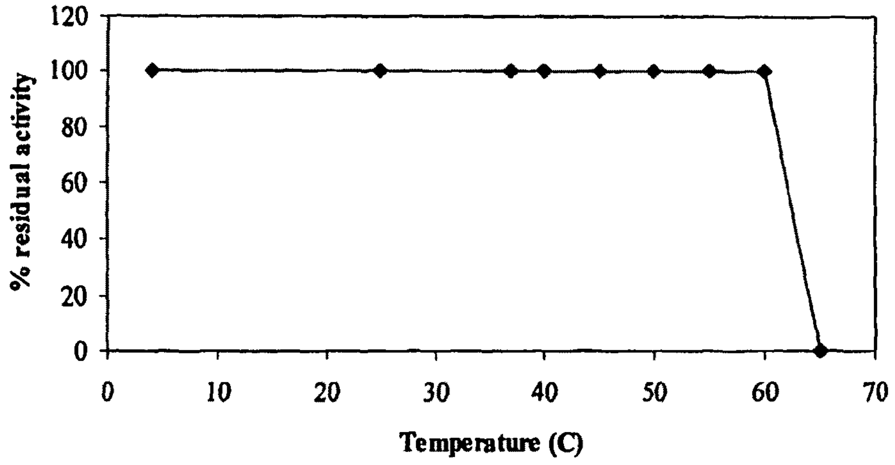

Figure 11 shows the results of a viability assay of various bacterial strains in the presence of PlyPH. The bacterial strains were grown in BHI liquid media for 3 hours with gyratory shaking at 30°C, washed and suspended in PBS at half the original culture volume. One hundred microliters of each bacterial strain suspension was added to 100μL of purified PlyPH at 300μg/mL or 40 units/mL. In control experiments, PBS was used instead of PlyPH. All reactions were incubated at 15 minutes at room temperature, followed by immediate serial dilutions and plating on BHI agar for viability counts. The lytic effect of PlyPH was calculated as the ratio of Bacillus viability incubated with PBS to viability upon incubation with PlyPH.

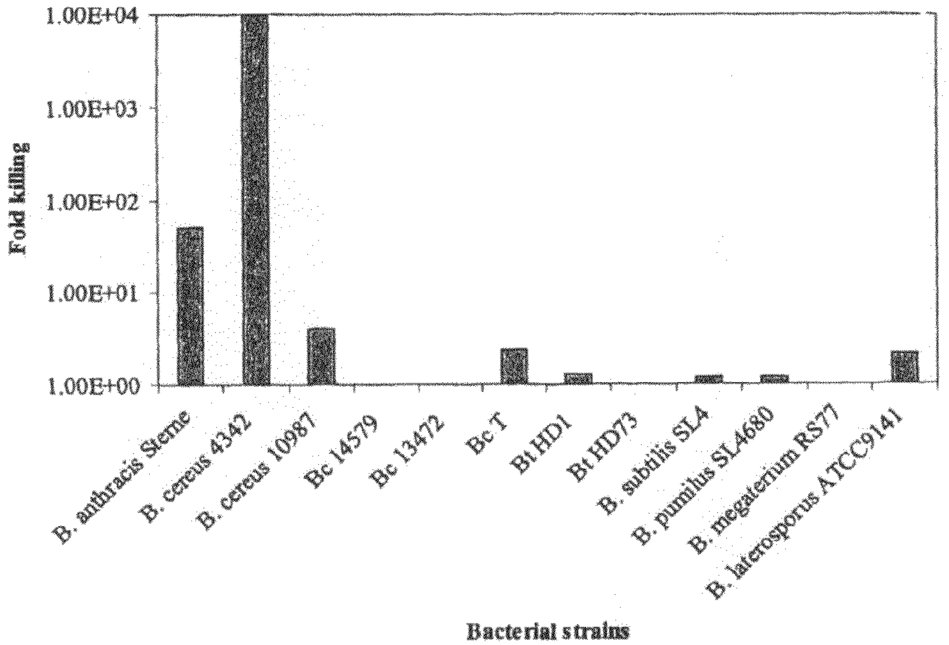

Figure 12A shows results from a viability assay of a mixture of various bacterial strains in the presence of PlyPH measured by luminescence assay, showing specificity of lytic action of PlyPH against certain bacteria in the mixture. This experiment demonstrates that PlyPH is able to selectively kill B. cereus 4342 in a mixture of bacteria (Figure 12A). In contrast, Figure 12B shows the results from a comparable viability assay of a similar mixture of bacterial strains shown in Figure 12A exposed to Bacterial Cell Releasing Agent (BRA) instead of PlyPH.

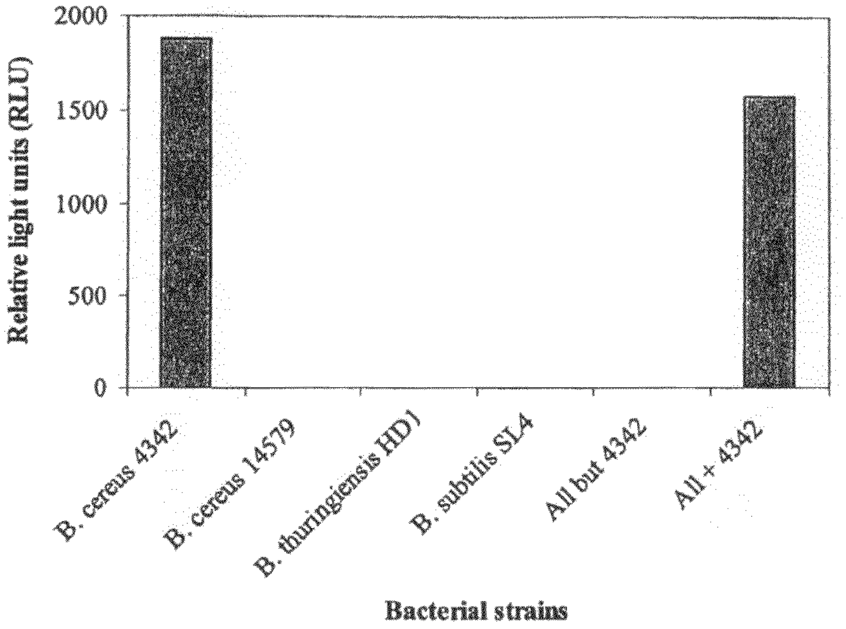

Figure 12B shows that BRA has a broad spectrum of activity and kills non-discriminately compared to PlyPH. BRA is a non-specific bacterial lysis reagent that should lyse and release ATP from all bacterial samples indiscriminately.
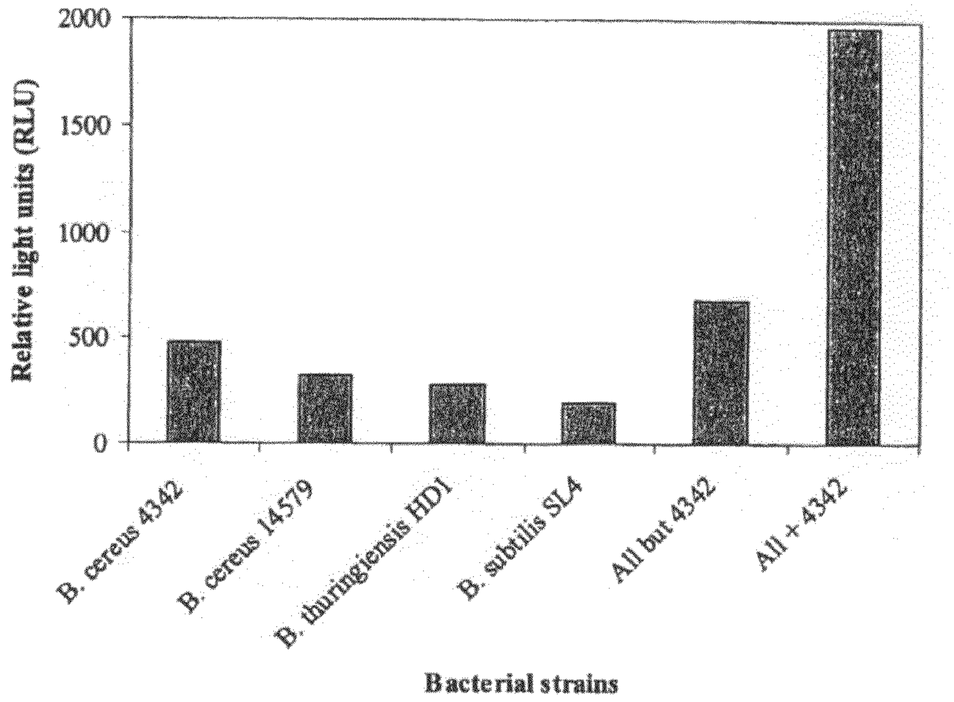

Figure 13A shows the effect of preimmune and hyperimmune rabbit sera on PlyPH activity. The effects were measured by differences in viability of B. cereus 4342 compared with control reactions: 50µL of PlyPH at 800µg/mL protein, or 128 units/mL lytic activity was incubated with 50µL of each serum dilution for several minutes prior to the addition of 100µL of B. cereus 4342 suspension. The assays were incubated at room temperature for 15 minutes, followed by plating on BHI agar for B. cereus viability counts. The starting B. cereus counts prior to the addition of serum or lysin (starting bact counts), and a B. cereus-lysin assay in the absence of serum (no ab added) served as controls. Five sets of serum dilutions are represented in the center, with 1 being undiluted, 2 being a two-fold, 4 being four-fold, 8 being eight-fold and 16 being sixteen fold dilution in Phosphate Buffered Saline (PBS). The effects of preimmune sera are represented in grey, while the effects of hyperimmune sera are represented in black.

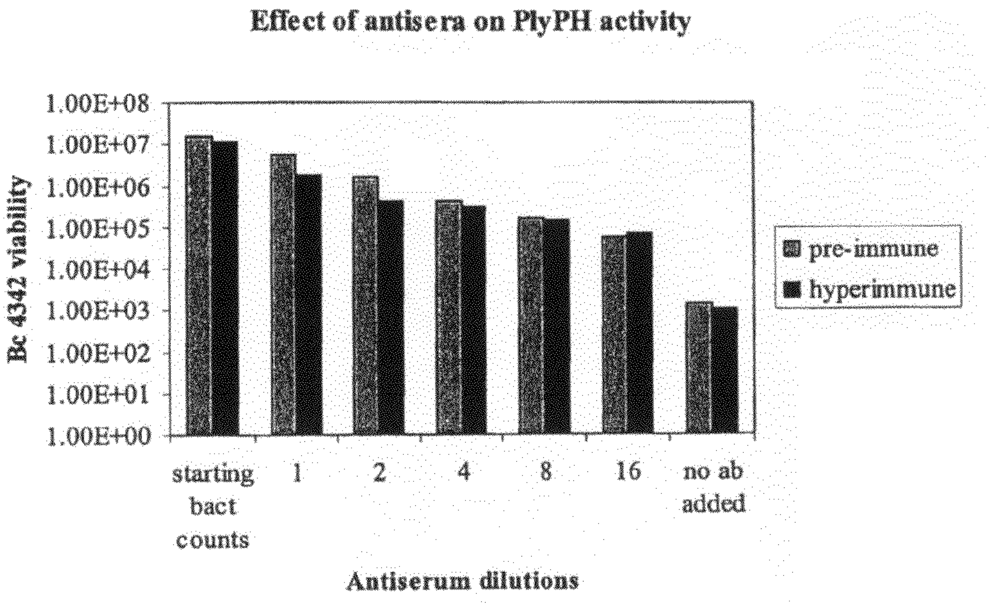

Figure 13B shows the effect of preimmune and hyperimmune rabbit sera on PlyG activity. The effects were measured by differences in viability of B. cereus 4342 compared with control reactions: 50μL of PlyG at 800μg/mL protein, or 128 units/mL lytic activity was incubated with 50μL of each serum dilution for several minutes prior to the addition of 100μL of B. cereus 4342 suspension. The assays were incubated at room temperature for 15 minutes, followed by plating on BHI agar for B. cereus viability counts. The starting B. cereus counts prior to the addition of serum or lysin (starting bact counts), and a B. cereus-lysin assay in the absence of serum (no ab added) served as controls. Five sets of serum dilutions are represented in the center, with 1 being undiluted, 2 being a two-fold, 4 being four-fold, 8 being eight-fold and 16 being sixteen fold dilution in Phosphate Buffered Saline (PBS). The effects of preimmune sera are represented in grey, while the effects of hyperimmune sera are represented in black.

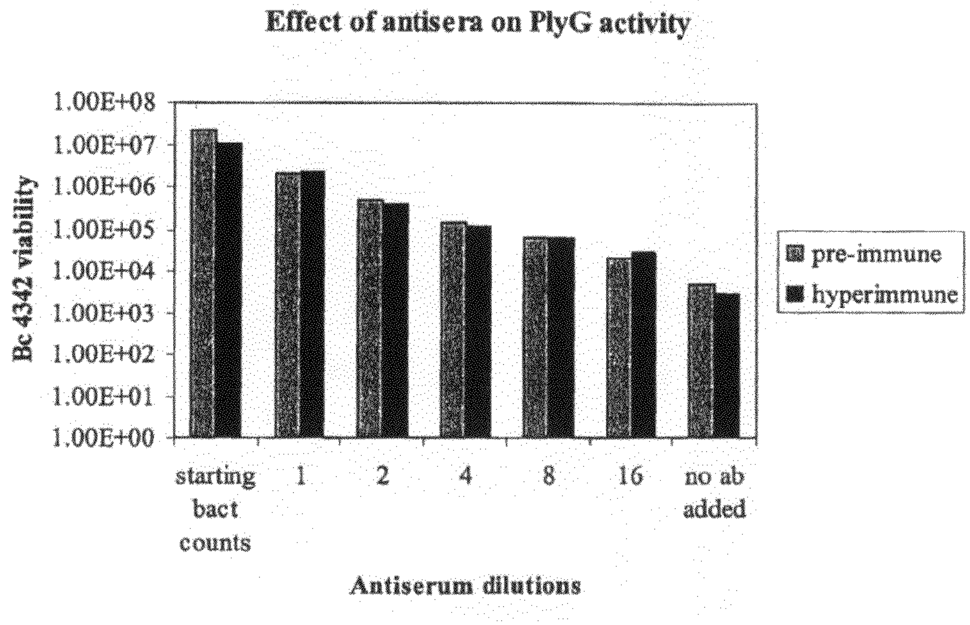

Figure 14 shows the survival of BALB/c mice injected with B. cereus RSVF1 through the intraperitoneal route, then treated with buffer or PlyPH, as indicated. Each BALB/c mouse was injected with a B. cereus 4342 PBS suspension containing approximately 2.5x106 CFU in 100μL into the intraperitoneal cavity. About 10 minutes later, mice were either injected with 400μL sterile buffer, or 400μL purified and filter sterilized PlyPH containing an estimated 300 units/mL.

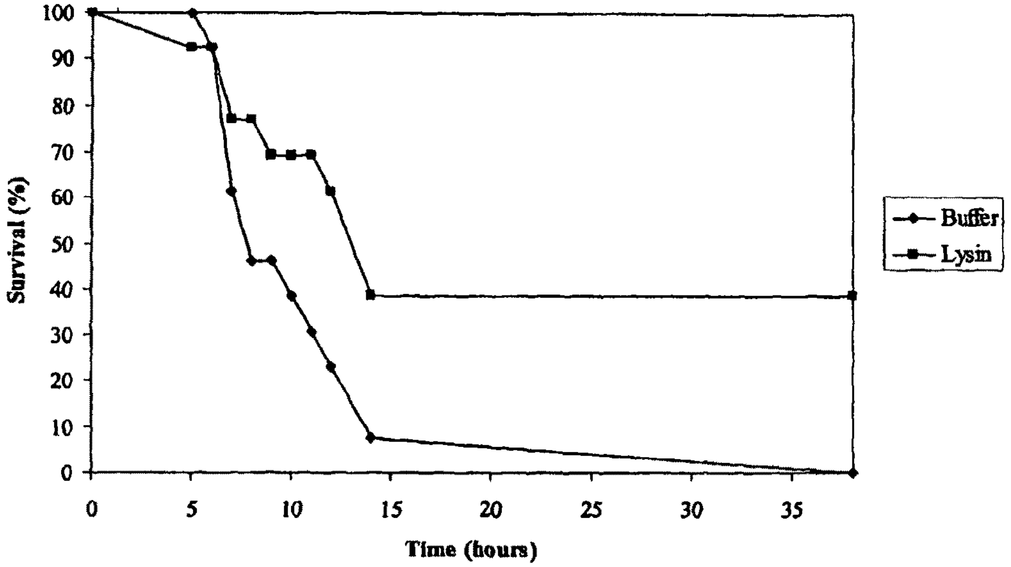

Figure 15 shows the increased killing of germinated spores of B. cereus 4342 exposed to the PlyPH enzyme, compared to a germinating spore suspension incubated with PBS instead. PlyPH was able to decrease the viability of germinating B. cereus 4342 spores by almost 3 logs after 5 hours.
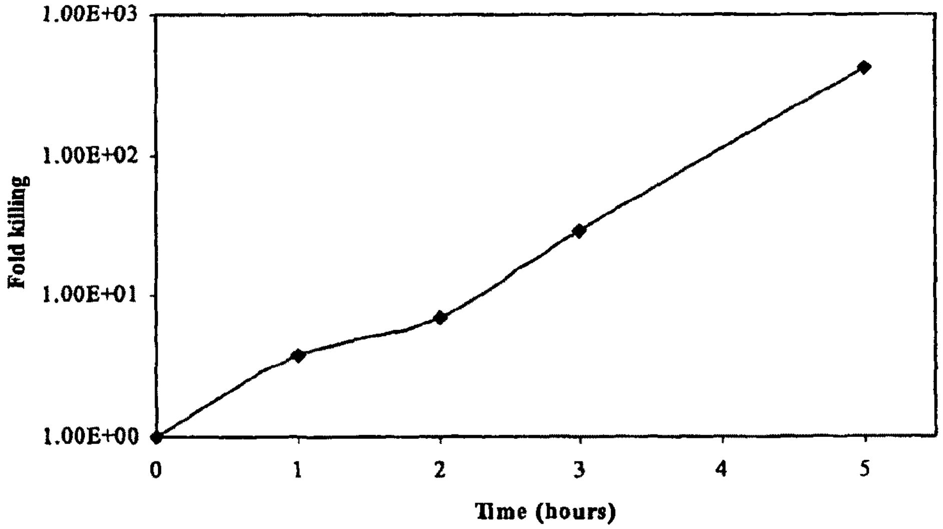

Figure 16 shows the effect of PlyPH on pronase treated, sodium periodate (NaIO4) treated and untreated B. cereus 4342 as observed by 15 minute OD assays are shown on the left panels. Control reactions with PBS instead of PlyPH are shown on the right panels. An inhibition assay of PlyPH lytic activity on B. cereus 4342 by 4342 extracted surface carbohydrates is shown on the bottom. Where viability assays were carried out, the bacterial counts after 15 minute incubation were listed adjacent to the corresponding reaction. The number below each graph is the Vmax value, which represents the change in optical density per unit time.

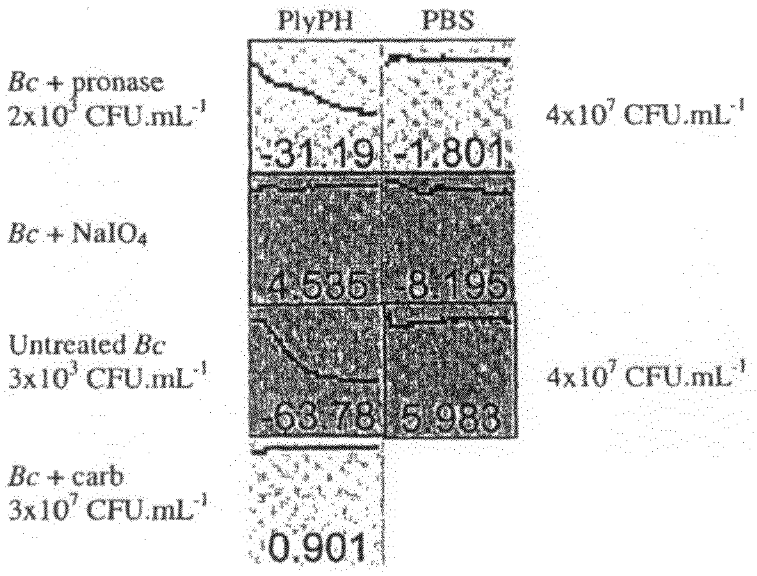

SEQUENCE LISTING

```
<160> NUMBER OF SEQ ID NOS: 6

<210> SEQ ID NO 1
<211> LENGTH: 268
<212> TYPE: PRT
<213> ORGANISM: Bacillus anthracis

<400> SEQUENCE: 1

Met Gly Tyr Ile Val Asp Ile Ser Lys Trp Asn Gly Asn Ile Asn Trp
1               5                   10                  15

Asp Val Ala Ala Pro Gln Leu Asp Phe Val Ile Ala Arg Val Gln Asp
            20                  25                  30

Gly Ser Asn Tyr Ile Asp Pro Leu Tyr Lys Ser Tyr Val Gln Ala Met
        35                  40                  45

Lys Thr Arg Asn Ile Pro Phe Gly Asn Tyr Ala Phe Cys Arg Phe Ile
    50                  55                  60

Ser Ile Ala Asp Ala Lys Lys Glu Ala Gln Asp Phe Trp Asn Arg Gly
65                  70                  75                  80

Asp Lys Ser Ala Thr Val Trp Val Ala Asp Val Glu Val Lys Thr Met
                85                  90                  95

Asp Asp Met Ile Ala Gly Thr Gln Ala Phe Ile Asp Glu Leu Arg Arg
            100                 105                 110

Leu Gly Ala Lys Lys Val Gly Leu Tyr Val Gly His His Met Tyr Gly
        115                 120                 125

Pro Phe Gly Met Ala Asn Val Lys Ser Asp Phe Val Trp Ile Pro Arg
    130                 135                 140

Tyr Gly Gly Asn Lys Pro Ala Tyr Pro Cys Asp Ile Trp Gln Tyr Thr
145                 150                 155                 160

Glu Thr Gly Asn Val Pro Gly Ile Gly Lys Cys Asp Leu Asn Gln Leu
                165                 170                 175

Ile Gly Asn Lys Pro Leu Ser Trp Phe Thr Glu Ser Val Pro Lys Gln
            180                 185                 190

Glu Asn Ile Gln Ala Gln Val Ser Lys Gln Asn Ile Ile Gln Ser Gly
        195                 200                 205

Ala Phe Ser Pro Tyr Glu Thr Pro Asp Val Met Gly Ala Leu Thr Ser
    210                 215                 220

Leu Lys Met Thr Ala Thr Phe Ile Leu Gln Ser Asp Gly Leu Thr Tyr
225                 230                 235                 240

Phe Val Thr Glu Pro Thr Ser Asp Thr Gln Leu Asn Ala Leu Lys Ser
                245                 250                 255

Trp Leu Asp Arg Lys Gly Trp Trp Tyr Glu Val Lys
            260                 265


<210> SEQ ID NO 2
<211> LENGTH: 233
<212> TYPE: PRT
<213> ORGANISM: Bacillus anthracis

<400> SEQUENCE: 2

Met Glu Ile Gln Lys Lys Leu Val Asp Pro Ser Lys Tyr Gly Thr Lys
```

-continued 1 5 10 15

Cys Pro Tyr Thr Met Lys Pro Lys Tyr Ile Thr Val His Asn Thr Tyr
20 25 30

Asn Asp Ala Pro Ala Glu Asn Glu Val Ser Tyr Met Ile Ser Asn Asn
35 40 45

Asn Glu Val Ser Phe His Ile Ala Val Asp Asp Lys Lys Ala Ile Gln
50 55 60

Gly Ile Pro Leu Glu Arg Asn Ala Trp Ala Cys Gly Asp Gly Asn Gly
65 70 75 80

Ser Gly Asn Arg Gln Ser Ile Ser Val Glu Ile Cys Tyr Ser Lys Ser
85 90 95

Gly Gly Asp Arg Tyr Tyr Lys Ala Glu Asp Asn Ala Val Asp Val Val
100 105 110

Arg Gln Leu Met Ser Met Tyr Asn Ile Pro Ile Glu Asn Val Arg Thr
115 120 125

His Gln Ser Trp Ser Gly Lys Tyr Cys Pro His Arg Met Leu Ala Glu
130 135 140

Gly Arg Trp Gly Ala Phe Ile Gln Lys Val Lys Asn Gly Asn Val Ala
145 150 155 160

Thr Thr Ser Pro Thr Lys Gln Asn Ile Ile Gln Ser Gly Ala Phe Ser
165 170 175

Pro Tyr Glu Thr Pro Asp Val Met Gly Ala Leu Thr Ser Leu Lys Met
180 185 190

Thr Ala Asp Phe Ile Leu Gln Ser Asp Gly Leu Thr Tyr Phe Ile Ser
195 200 205

Lys Pro Thr Ser Asp Ala Gln Leu Lys Ala Met Lys Glu Tyr Leu Asp
210 215 220

Arg Lys Gly Trp Trp Tyr Glu Val Lys
225 230

<210> SEQ ID NO 3
<211> LENGTH: 310
<212> TYPE: PRT
<213> ORGANISM: Bacillus anthracis

<400> SEQUENCE: 3

Met Glu Ile Arg Lys Lys Leu Val Asp Pro Ser Lys Tyr Cys Ile Lys
1 5 10 15

Cys Pro Tyr Thr Met Asn Pro Glu Phe Ile Thr Val His Asn Thr Tyr
20 25 30

Asn Asp Ala Thr Ala Glu Asn Glu Val Ala Tyr Met Ile Arg Asn Asp
35 40 45

Asn Gln Val Ser Phe His Ile Ala Val Asp Asp Lys Glu Ala Val Gln
50 55 60

Gly Ile Pro Leu Glu Arg Asn Ala Trp His Thr Gly Asp Gly Asn Gly
65 70 75 80

Asn Gly Asn Arg Lys Ser Ile Gly Val Glu Ile Cys Tyr Ser Leu Ser
85 90 95

Gly Gly Asp Arg Tyr Tyr Lys Ala Glu Asp Asn Ala Ala Ile Val Val
100 105 110

Ala Gln Leu Met Lys Gln Tyr Asn Ile Pro Ile Lys Lys Val Arg Thr
115 120 125

His Gln Ser Trp Ser Gly Lys Tyr Cys Pro His Arg Met Leu Ala Glu
130 135 140

Gly Arg Trp Asn Asn Phe Ile Glu Arg Val Gln Asn Ala Tyr Asn Gly

```
145                 150                 155                 160

Asp Gly Lys Val Thr Pro Thr Leu Ile Pro Pro Ser Thr Asn Gly Thr
                165                 170                 175

Gly Ile Ala Tyr Ile Glu Gly Asn Gly Ile Asn Leu Arg Lys Gly Leu
            180                 185                 190

Gly Thr Gly Tyr Gly Val Ile Arg Gln Leu Gly Lys Gly Glu Ser Tyr
        195                 200                 205

Glu Val Trp Gly Gln Ser Asn Gly Trp Leu Asn Leu Gly Gly Asn Gln
    210                 215                 220

Trp Ile Tyr Asn Asp Ser Ser Tyr Ile Arg Tyr Thr Gly Glu Ser Thr
225                 230                 235                 240

Pro Thr Ser Ser Gln Ser Val Asn Asn Gly Val Gly Ile Val Thr Ile
                245                 250                 255

Thr Ala Asp Val Leu Arg Val Arg Lys Gly Pro Gly Thr Asn Tyr Asp
            260                 265                 270

Ile Val Lys Asn Val Tyr Gln Gly Glu Gln Tyr Gln Ser Trp Gly Tyr
        275                 280                 285

Arg Asp Gly Trp Tyr Asn Val Gly Gly Asp Gln Trp Val Ser Gly Glu
    290                 295                 300

Tyr Val Lys Phe Glu Asp
305                 310


<210> SEQ ID NO 4
<211> LENGTH: 245
<212> TYPE: PRT
<213> ORGANISM: Bacillus anthracis

<400> SEQUENCE: 4

Met Ala Arg Tyr Ser Leu His Ala Gly His Asn Ser Ile Val Gln Gly
1               5                   10                  15

Ala Asn Tyr Gly Asn Arg Lys Glu His Ile Met Asp Arg Gln Val Lys
            20                  25                  30

Asp Ala Val Val Ala Lys Leu Arg Ala Leu Gly His Thr Val Tyr Asp
        35                  40                  45

Asp Thr Asp Glu Val Gly Thr Thr Gln Ala Gln Asn Leu Asn Asn Ile
    50                  55                  60

Val Ser Lys Thr Asn Ser His Asp Val Asp Leu Val Val Ser Phe His
65                  70                  75                  80

Leu Asn Ser Tyr Asp Thr Arg Ala Asn Gly Val Glu Val Leu Tyr Tyr
                85                  90                  95

Asp Gln Gln Ala Leu Ser Ala Lys Ile Ala Ala Gln Leu Ser Lys Asp
            100                 105                 110

Ile Gly Trp Ser Asn Arg Gly Ala Lys Glu Arg Lys Asp Leu Tyr Val
        115                 120                 125

Leu Ser Asn Thr Lys Ala Pro Ala Ile Leu Ile Glu Leu Gly Phe Ile
    130                 135                 140

Asp Asn Glu Ala Asp Met Ala Lys Trp Asn Pro Asp Lys Ile Ala Asn
145                 150                 155                 160

Ser Ile Val Tyr Ala Leu Thr Gly Gln Ser Gly Gly Thr Thr Pro Pro
                165                 170                 175

Ser Lys Gln Asn Ile Ile Gln Ser Gly Ala Phe Ser Pro Tyr Glu Thr
            180                 185                 190

Pro Asp Val Met Gly Ala Leu Thr Ser Leu Lys Met Thr Ala Asn Phe
        195                 200                 205

Ile Leu Gln Ser Asp Gly Leu Thr Tyr Phe Ile Ser Glu Pro Thr Ser
```

```
    210                 215                 220

Asp Ala Gln Leu Lys Gly Met Thr Asp Tyr Leu Asp Arg Arg Gly Trp
225                 230                 235                 240

Trp Tyr Glu Val Lys
                245


<210> SEQ ID NO 5
<211> LENGTH: 234
<212> TYPE: PRT
<213> ORGANISM: Bacillus anthracis

<400> SEQUENCE: 5

Met Glu Ile Arg Lys Lys Leu Val Val Pro Ser Lys Tyr Gly Thr Lys
1               5                   10                  15

Cys Pro Tyr Thr Met Lys Pro Lys Tyr Ile Thr Val His Asn Thr Tyr
            20                  25                  30

Asn Asp Ala Pro Ala Glu Asn Glu Val Asn Tyr Met Ile Thr Asn Asn
        35                  40                  45

Asn Glu Val Ser Phe His Val Ala Val Asp Asp Lys Gln Ala Ile Gln
    50                  55                  60

Gly Ile Pro Trp Glu Arg Asn Ala Trp Ala Cys Gly Asp Gly Asn Gly
65                  70                  75                  80

Pro Gly Asn Arg Glu Ser Ile Ser Val Glu Ile Cys Tyr Ser Lys Ser
                85                  90                  95

Gly Gly Asp Arg Tyr Tyr Lys Ala Glu Asn Asn Ala Val Asp Val Val
            100                 105                 110

Arg Gln Leu Met Ser Met Tyr Asn Ile Pro Ile Glu Asn Val Arg Thr
        115                 120                 125

His Gln Ser Trp Ser Gly Lys Tyr Cys Pro His Arg Met Leu Ala Glu
    130                 135                 140

Gly Arg Trp Gly Ala Phe Ile Gln Lys Val Lys Ser Gly Asn Val Ala
145                 150                 155                 160

Ser Ala Thr Val Thr Pro Lys Gln Asn Ile Ile Gln Thr Gly Ala Phe
                165                 170                 175

Ser Pro Tyr Glu Leu Pro Asp Ala Val Gly Ala Leu Lys Ser Leu Asn
            180                 185                 190

Met Thr Gly Lys Ala Ile Ile Asn Pro Glu Gly Leu Thr Tyr Ile Val
        195                 200                 205

Thr Asp Pro Thr Ser Asp Val Gln Leu Gln Ala Phe Lys Glu Tyr Leu
    210                 215                 220

Glu Arg Lys Asp Trp Trp Tyr Asp Asp Lys
225                 230


<210> SEQ ID NO 6
<211> LENGTH: 583
<212> TYPE: PRT
<213> ORGANISM: Bacillus anthracis

<400> SEQUENCE: 6

Met Ile Cys Val Leu Ser Ser Met Met Lys Lys Gly Phe Tyr Asn Val
1               5                   10                  15

Leu Ala Ala Ser Ile Val Phe Ser Met Val Thr Ile Pro Asn Tyr Ser
            20                  25                  30

Tyr Ala Asn Glu Leu Asp Lys Thr Val Thr Val Ser Pro Asp Glu Gln
        35                  40                  45

Ala Leu Lys Ser Ile Glu Asn His Met Lys Asp Glu Asp Gly Arg Gly
    50                  55                  60
```

```
Glu Asp Lys Gly Val Arg Asn Glu Val Gln Gly Glu Phe Leu Val His
65                  70                  75                  80

Ile Val Lys Glu Val Pro Leu Tyr Asp Ser Ser Asn Phe Gln Lys Glu
                85                  90                  95

Thr Gly Val Arg Ile Ser Asn Gln Val Val Lys Ala Glu Lys Arg Lys
            100                 105                 110

Gly Asn Ala Tyr Tyr Val Gln Thr Ser Ser Gly Thr Gly Trp Ile Gln
        115                 120                 125

Asn Ser Asp Gly Asn Val Glu Val Lys Glu Ile His Pro Leu Leu Ser
    130                 135                 140

Glu Lys Leu Ile Val Asn Glu Glu Thr Ser Thr Tyr Ser Glu Pro Phe
145                 150                 155                 160

Ala Ser Tyr Lys Glu Glu Asn Val Leu Glu Pro Gln Thr Ile Gln Ala
                165                 170                 175

Ile Gly Gln Ala Gly Glu Trp Phe Gln Val Lys Ile Asn Asn Glu Met
            180                 185                 190

Lys Trp Ile His Ser Pro Ser Ala Lys Phe Glu Gly Thr Lys Ala Ser
        195                 200                 205

Leu Ile Gln Gly Ala Ala Pro Ile Arg Thr Lys Tyr Ala Ala Ala Met
    210                 215                 220

Tyr Ala Ala Pro Ile Glu Glu Lys Thr Thr Asp Ile Tyr Gly Val Pro
225                 230                 235                 240

Leu Lys Glu Met Ile Val Pro Lys Gly Asn Glu Asn Ile Arg Pro Gly
                245                 250                 255

Tyr Ala Met Asn Pro Lys Tyr Ile Thr Ile His Glu Thr Asp Asn Tyr
            260                 265                 270

Ser Val Gly Ala Asn Ala Arg Asn His Ala Ile Tyr Leu Tyr Asn Gln
        275                 280                 285

Ala Thr Gly Thr Glu Asp Arg Ser Ala Ser Trp His Phe Thr Val Asp
    290                 295                 300

Asp Lys Glu Ile Tyr Gln His Leu Pro Leu Asn Glu Asn Ala Trp His
305                 310                 315                 320

Ala Gly Asp Gly Ala Glu Gly Thr Gly Asn Arg Glu Ser Ile Ala Ile
                325                 330                 335

Glu Ile Ala Val Asn Glu Asp Gly Asp Tyr Asn Lys Ala Val Glu Asn
            340                 345                 350

Ala Arg Lys Leu Ala Ala Tyr Leu Met Gly Glu Leu Asn Ile Pro Leu
        355                 360                 365

Glu Asn Val Lys Lys His Gln Phe Trp Ser Gly Lys Ile Cys Pro Ala
    370                 375                 380

Ile Met Ile Lys Asn Asn Gly Trp Glu Pro Phe Leu Gln Gly Thr Lys
385                 390                 395                 400

Met Tyr Tyr Asp Ala Asn His Lys Asp Asp Ile Thr Gly Gly Trp Tyr
                405                 410                 415

Glu Ala Ala Ile Arg Glu Leu Asp Lys Arg Gly Ile Met Val Gly Asp
            420                 425                 430

Gly Lys Gly Ser Tyr Trp Pro Glu Arg Leu Val Thr Arg Gly Glu Phe
        435                 440                 445

Ala Asn Phe Ile Ser Arg Ser Leu Gln Leu Pro Glu Gly Ser Ser Asn
    450                 455                 460

Phe Ser Asp Leu Asn Ala Ala His Pro Ser Leu Ile Asp Gly Ile Asn
465                 470                 475                 480

Arg Ala Ala Ser Ala Gly Ile Ile Ser Gly Arg Gly Asn Gly Ile Phe
```

-continued

```
                485                 490                 495

Ala Pro Asn Asp Thr Ile Lys Arg Asp Glu Val Val Ile Met Ile Asp
            500                 505                 510

Arg Ala Leu Gln Tyr Lys Lys Ile Lys Gly Asn Leu Val Pro Leu Pro
        515                 520                 525

Phe Ser Asp Gln Asp Leu Ala Tyr Asp Lys Gln Ala Val Gln Arg Val
    530                 535                 540

Tyr Gly Leu Gly Ile Val Lys Gly Asn Glu Asn Asn Glu Phe Met Pro
545                 550                 555                 560

Lys Gly Ser Ala Thr Arg Gly Glu Ser Ala Ala Phe Ile Asn Arg Met
                565                 570                 575

Leu Glu Val Ile Glu Ser Asn
            580
```

BACTERIOPHAGE LYSINS FOR *BACILLUS ANTHRACIS*

RELATED APPLICATIONS

This application is the national phase under 35 U.S.C. §371 of PCT International Application No, PCT/US2006/021094, which has an International Filing Date of May 31, 2006 and designated the United States of America and is incorporated herein by reference in its entirety, and which in turn claims the benefit to U.S. provisional patent application Ser. No. 60/688,270, entitled "BACTERIOPHAGE LYSINS FOR BACILLUS ANTHRACIS," filed Jun. 6, 2005 by Yoong et al., which is hereby incorporated by reference in its entirety.

TECHNICAL FIELD

The present disclosure relates to the identification and use of phage associated lytic enzymes to rapidly and specifically detect and kill *Bacillus anthracis* and certain related bacteria.

BACKGROUND

Anthrax is a disease believed to be caused by the spore-forming bacterium, *Bacillus anthracis* ("*B. anthracis*"), a bacterium that is readily found in soil. *B. anthracis* is believed to primarily cause disease in plant-eating animals. Though infrequent, when humans do become infected, they usually acquire the bacterium from contact with infected animals, animal hides or hair, or animal feces. The human disease has a relatively short incubation period (less than a week) and usually progresses rapidly to a fatal outcome.

In humans, anthrax may occur in three different forms: cutaneous anthrax, gastrointestinal anthrax and inhalation anthrax. Cutaneous anthrax, the most common form in humans, is usually acquired when the bacterium, or spores of the bacterium, enter the body through an abrasion or cut on the skin. The bacteria multiply at the site of the abrasion, cause a local edema, and a series of skin lesions—papule, vesicle, pustule and necrotic ulcer—are sequentially produced. Lymph nodes nearby the site are eventually infected by the bacteria and, in cases where the organisms then enter the bloodstream (20% of cases), the disease is often fatal. Gastrointestinal anthrax can be caused by eating contaminated meat. Initial symptoms include nausea, vomiting and fever. Later, infected individuals present with abdominal pain, severe diarrhea and vomiting of blood. This type of anthrax is fatal in 25% to 60% of cases. Inhalation anthrax (also called woolsorters' disease) can be acquired through inhalation of the bacteria or spores. Initial symptoms are similar to those of a common cold. Symptoms then worsen and these individuals present with high fever, chest pain and breathing problems. The infection normally progresses systemically and produces a hemorrhagic pathology. Inhalation anthrax is fatal in almost 100% of cases. Cutaneous anthrax is acquired via injured skin or membranes, entry sites where the spore germinate into vegetative cells. Proliferation of vegetative cells results in gelatinous edema. Alternatively, inhalation of the spores results in high fever and chest pain. Both types may be fatal unless the invasive aspect of the infection may be intercepted.

*B. anthracis* is able to form highly resistant spores that can survive in the environment for prolonged periods of time. Only the spore form of *B. anthracis* is believed to be infectious, the vegetative form of the organism has not been shown to be transmittable. The vegetative bacilli are believed to survive very poorly outside the host. In fact, it is believed that the complete *B. anthracis* life cycle may solely occur within the mammalian host. Once *B. anthracis* spores enter the body, they are phagocytosed by macrophages. The incubation period of *B. anthracis* spores within the human body can be up to 60 days prior to germination. Not only do spores survive within the macrophage, but it is believed that they germinate within the macrophage phagosomal compartment. The macrophages are also believed to serve as a vehicle for transporting the bacteria to regional lymph nodes, particularly the mediastinal lymph nodes, where escape from macrophages allows their entry into the bloodstream. *B. anthracis* expression of a toxin causes macrophage lysis, and allows bacteria to enter the bloodstream. Vegetative bacterial counts can reach up to $10^8$ per milliliter of blood. Once germination has occurred within the body, the bacteria remain in their vegetative form, with sporulation being suppressed in the absence of air.

*B. anthracis* is believed to possess two major virulence components. The first virulence component is a polysaccharide capsule which contains poly-D-glutamate polypeptide. The poly-D-glutamate capsule is not believed to be toxic, but plays an important role in protecting the bacterium against anti-bacterial components of serum and phagocytic engulfment. As the *B. anthracis* bacterium multiplies in the host, it produces a secreted toxin which is the second virulence component of the organism. This anthrax toxin mediates symptoms of the disease in humans. Full virulence of *B. anthracis* is believed to require the production of a protein capsule and two toxins, namely the lethal toxin and the edema toxin. Strains lacking any one of these virulence factors are attenuated. However, the diseases caused by *B. anthracis* are believed to be toxin mediated, with the injection of both anthrax toxins being able to reproduce anthrax disease progression in animals. This further accentuates the need for early diagnosis and treatment as elimination of vegetative bacilli may not improve patient prognosis if high levels of toxins are already present in the bloodstream, as evidenced in animal studies. The factors essential for *B. anthracis* virulence all function in some manner to evade or suppress the host immune system.

The anthrax toxin is believed to comprise three distinct proteins encoded by the bacterium: protective antigen (PA), lethal factor (LF) and edema factor (EF). PA is the component of the anthrax toxin that is believed to bind to host cells using an unidentified cell-surface receptor. Once it binds to cell surfaces, EF or LF may subsequently interact with the bound PA. The complexes are then internalized by the host cell with significant effects. EF is an adenylate cyclase which causes deregulation of cellular physiology, resulting in edema. LF is a metalloprotease that cleaves specific signal transduction molecules within the cell (MAP kinase isoforms), causing deregulation of said pathways, and cell death. Injection of PA, LF or EF alone, or LF in combination with EF, into experimental animals produces no effects. However, injection of PA plus EF produces edema. Injection of PA plus LF is lethal, as is injection of PA plus EF plus LF.

As an acute, febrile disease of virtually all warm-blooded animals, including man, anthrax can be used in biological weapons (BW). For example, ten grams of anthrax spore may kill as many people as a ton of the chemical warfare agent, sarin. Terrorists have included dry spores in letters. Biological weapons of mass destruction have been developed that contain large quantities of anthrax spores for release over enemy territory. Once released, spores may contaminate a wide geographical area, infecting nearly all susceptible mammals. Due to the spore's resistance to heat and dry conditions, contaminated land may remain a danger for years. In view of the serious threat posed by the disease, effective diagnostic tools are needed to assist in prevention and control of natural and man-made outbreaks. Due to the highly lethal nature of anthrax and BW agents in general, there is great need for the development of sensitive and rapid BW agent detection. Current detection technology for biological warfare agents have traditionally relied on time-consuming laboratory analysis or onset of illness among people exposed to the BW agent.

Bacteriophages specific for *B. anthracis* and related *B. cereus* bacteria strains may be isolated and used to detect and treat these bacteria. Bacteriophages near *B. anthracis* spores during spore germination may be used to infect and lyse the bacteria. A variety of phage-based bacterial therapies have been reviewed. D. H. Duckworth, P. A. Gulig, "Bacteriophages: Potential treatment for bacterial infections," BioDrugs, 16(1), 57-62 (2002). There are various environmental bacteriophages present in soils that may infect and lyse *B. anthracis* under controlled conditions. H. W. Ackermann, et al., "New *Bacillus* bacteriophage species," Archives of Virology, 135(3-4), 333-344 (1994); H. W. Ackerman, M. S. Dubrow, Viruses of prokaryotes: General properties of bacteriophages, Boca Raton, Fla., CRC Press, Inc. (1989). Bacteriophages for *B. anthracis* may be isolated from various sources. For instance, Walter et al. report the isolation of Phages Nk, DB and MH for *B. anthracis* in topsoil. Walter, M H, Baker, D D, "Three *Bacillus anthracis* bacteriophages from topsoil," Curr Microbiol. 2003 July; 47(1): 55-58.

The direct introduction of bacteriophages into an animal to prevent or fight diseases can be subject to certain potential difficulties. For example, both the bacteria and the phage have to be in the correct and synchronized growth cycles for the phage to attach. Additionally, the number of phages has to be calibrated to attach to the bacteria; if there are too many or too few phages, there will be either no attachment or no production of the lysing enzyme. The phage is preferably active enough to be effective. The phages may also be inhibited by many things including bacterial debris from the organism it is going to attack. Further complicating the direct use of a bacteriophage to treat bacterial infections is the possibility of immunological reactions within the subject being treated, potentially rendering the phage non-functional. The ability of bacteriophages to lyse and kill target bacterial may also be decreased by sunlight, UV light, desiccation or other conditions encountered during storage or use of a phage-containing therapeutic agent.

One promising approach to the detection and treatment of *B. anthracis* is the use of bacteriophage lytic enzymes as bacteriolytic agents. Bacteriophage lytic enzymes responsible for bacterial host lysis are also known as lysins. Many lysins can rapidly break down the bacterial cell wall in order to release progeny phage (Young, R. 1992. Bacteriophage lysis: mechanism and regulation. Microbial. Rev. 56:430-481). Structurally, lysins are commonly found as modular proteins with an amino terminal domain that confers the enzymatic activity for a peptidoglycan bond and a carboxy terminal domain that confers binding specificity to a carbohydrate epitope in the bacterial cell wall (Loessner, M., K. Kramer, F. Ebel, and S. Scherer. 2002. C-terminal domains of *Listeria monocytogenes* bacteriophage murein hydrolases determine specific recognition and high-affinity binding to bacterial cell wall carbohydrates. Mol. Microbiol. 44:335-349; Lopez, R., E. Garcia, P. Garcia, and J. L. Garcia. 1997. The pneumococcal cell wall degrading enzymes: a modular design to create new lysins? MicroB. Drug Resist. 3:199-211; Lopez, R., M. P. Gonzalez, E. Garcia, J. L. Garcia, and P. Garcia. 2000. Biological roles of two new murein hydrolases of *Streptococcus pneumoniae* representing examples of module shuffling. Res. Microbiol. 151:437-443; Sheehan, M. M., J. L. Garcia, R. Lopez, and P. Garcia. 1997. The lytic enzyme of the pnemococcal phage Dp-1: a chimeric enzyme of intergeneric origin. Mol. Microbiol. 25:717-725). Lysin are believed to provide at least one of the following enzymatic activities against a peptidoglycan substrate: muramidases, glucosaminidases, N-acetylmuramyl-L-alanine amidase and endopeptidases (Young, R. 1992. Bacteriophage lysis: mechanism and regulation. Microbiol. Rev. 56:430-481). Purified lysin from a bacteriophage can be applied exogenously to affect bacterial lysis (Loeffler, J. M., D. Nelson, and V. A. Fischetti. 2001. Rapid killing of *Streptococcus pneumoniae* with a bacteriophage cell wall hydrolase. Science. 294:2170-2172; Loessner, M., G. Wendlinger, and S. Scherer. 1995. Heterogeneous endolysins in *Listeria monocytogenes* bacteriophages: a new class of enzymes and evidence for conserved holin genes within the siphoviral lysis cassettes. Mol. Microbiol. 16:1231-1241; Loessner, M., S. K. Maier, H. Daubek-Puza, G. Wendlinger, and S. Scherer. 1997. Three *Bacillus cereus* bacteriophage endolysins are unrelated but reveal high homology to cell wall hydrolases from different bacilli. J. Bacteriol. 179:2845-2851; Nelson, D., L. Loomis, and V. A. Fischetti. 2001. Prevention and elimination of upper respiratory colonization of mice by group A streptococci by using a bacteriophage lytic enzyme. Prot. Natl. Acad. Sci. USA. 98:4107-4112).

Lysins are normally very specific to the bacterial species from which the lysin derived phage was isolated (Fischetti, V. A. 2003. Novel method to control pathogenic bacteria on human mucous membranes. Ann. N.Y. Acad. Sci. 987:207-214; Fischetti, V. A. 2001. Phage antibacterials make a comeback. Nature Biotechnol. 19:734-735). Although the range of bacteria targeted by lysins is less restrictive than the corresponding bacteriophage, lysins still maintain a degree of specificity, having minimal effects on other bacteria including commensal organisms. While bacteriophage host ranges are largely restrictive, recognizing only one specific antigen on its bacterial host, phage lysins are less restrictive, recognizing a specific carbohydrate molecule common to the particular species of host bacteria.

Bacterial resistance to phage lysins is believed to be less likely to arise as compared with bacteriophage adsorption for at least two reasons: firstly, because bacterial lysis upon exposure to lysin is almost immediate, not giving bacteria much possibility for mutation and secondly, because lysins bind to highly conserved molecules in the bacterial cell wall that are under selective pressure not to mutate. This is evidenced by the lysins from *S. pneumoniae* phages binding to choline, an essential component on the *S. pneumoniae* cell wall, and a lysin, PlyC, targeting *S. pyogenes* by specifically binding the alternating ($\alpha 1 \rightarrow 2$) and ($\alpha 1 \rightarrow 3$) linked polyrhamnose backbone of surface carbohydrates. The exposure of bacteria to subinhibitory lysin concentrations and mutagenesis studies have not identified bacteria that are resistant to the action of phage lysins (Schuch, R., D. Nelson, and V. A. Fischetti. 2002. A bacteriolytic agent that detects and kills *Bacillus anthracis*. Nature. 418:884-888). In contrast, bacterial resistance to many antibiotics are easily identified using the techniques used above. Furthermore, the problem with lysogenic conversion is completely eliminated with phage lysins, and animal testing have determined lysins to be safe. Of course lysin dosage will need to be worked out, taking into account the specific activity of each lysin considered, the route of injection, and the nature of infection being treated. Unlike phages, the use of lysin will not be complicated by its uncontrolled multiplication in the host.

The use of highly specific phage lysins have an advantage over antibiotics in that lysin only effects targeted bacterial strains, while having minimal effect on other bacteria including commensals. This property of targeted bacteriocidal activity makes lysins suitable for development into an alternative therapeutic agent. In fact, through mouse models, lysins have successfully been applied in the elimination of *S. pyogenes, S. pneumoniae* and group B streptococcal colonization on mucosal surfaces, and the treatment of bacteremia caused by *S. pneumoniae* and a *B. anthracis*-like *B. cereus* strain (Cheng, Q., D. Nelson, S. Zhu, and V. A. Fischetti. 2005. Removal of group B streptococci colonizing the vagina and oropharynx of mice with a bacteriophage lytic enzyme. AntimicroB. Agents Chemother. 49:111-117; Jado, I., R. Lopez, E. Garcia, A. Fenoll, J. Casal, and P. Garcia. 2003. Phage lytic enzymes as therapy for antibiotic-resistant *Streptococcus pneumoniae* infection in a murine sepsis model. J. AntimicroB. Chemother. 52:967-973; Loeffler, J. M., D. Nelson, and V. A. Fischetti. 2001. Rapid killing of *Streptococcus pneumoniae* with a bacteriophage cell wall hydrolase. Science. 294:2170-2172; Loeffler, J. M., S. Djurkovic, and V. A. Fischetti. 2003. Phage lytic enzyme Cpl-1 as a novel antimicrobial for pneumococcal bacteremia. Infect. Immun. 71:6199-6204; Nelson, D., L. Loomis, and V. A. Fischetti. 2001. Prevention and elimination of upper respiratory colonization of mice by group A streptococci by using a bacteriophage lytic enzyme. Prot. Natl. Acad. Sci. USA. 98:4107-4112; Schuch, R., D. Nelson, and V. A. Fischetti. 2002. A bacteriolytic agent that detects and kills *Bacillus anthracis*. Nature. 418:884-888).

There is an ongoing need for therapies and agents effective in the diagnosis and control of bacterial contamination, colonization and infection, particularly with respect to *B. anthracis*. In addition, compounds with bacteriocidal effects may be useful in the decontamination of bacteria on inanimate surfaces and objects. The bactiophage lytic enzymes provided herein are useful in providing agents useful in the detection, treatment and decontamination of *B. anthracis* and related bacteria.

SUMMARY

The present disclosure relates to approaches to control and treat anthrax infections and anthrax spore decontamination using lytic enzymes obtained from bacterial viruses, known as bacteriophages, which can be used to break down the bacterial cell wall of target bacteria, such as *Bacillus anthracis*. The bacteriophage lytic enzymes are naturally produced during the lytic life cycle of bacteriophages which occurs in the bacterial cytoplasm. The end of this cycle results in the production of a lytic enzyme that lyses the bacterial to release the viral progeny. The lytic enzyme, termed a lysin, can be purified from the lysate or produced recombinantly. Administration of small quantities of preferred lytic enzymes to Gram-positive bacteria cause a rapid lysis and death of the Gram-positive bacterial organism.

Bacteriophage lytic agents effective against *B. anthracis* and related bacteria are provided herein, along with corresponding polypeptide and polynucleotide sequences relating to the same. Compositions comprising the lytic enzymes provided herein are useful in the diagnosis, treatment, and decontamination applications relating to *B. anthracis*. Also provided are methods of treatment and decontamination using compositions comprising the lytic enzymes, polypeptides or polynucleotide sequences disclosed herein.

One particularly preferred bacteriophage lytic enzyme is a lysin amplified from the genome of *B. anthracis* designated PlyPH, and polypeptide variants thereof. PlyPH is highly specific for *B. anthracis* and *B. anthracis*-like strains over a broad pH range described herein. PlyPH is believed to be active against *B. anthracis* over a broader pH range than other lysins. PlyPH exerts a highly specific lytic effect on *B. cereus* RSVF1, a strain representative of *B. anthracis* cured of its virulence plasmids. Notably, PlyPH maintains its activity over a desirably wide range of temperature, pH, and salt concentrations. PlyPH is a phage lysin effective in vitro and in vivo in the killing of *B. anthracis*-like *B. cereus*, thereby adding another potential therapeutic option in treating anthrax. Furthermore, with its broad pH range, and high temperature and salt stability, PlyPH may be applied in more varied environments and treatments.

While certain preferred embodiments are illustrated with respect to PlyPH, other preferred lytic enzymes specific to anthrax are also provided herein, including lysins that maintain phage lytic activity over desirable ranges of pH, temperature and/or salt concentrations. Preferred lysins include fragments and variants of PlyPH and other lysins described herein that maintain specificity for killing target bacteria, such as *B. anthracis*.

In one embodiment, compositions comprising one or more lytic enzymes, or related polypeptides or polynucleotides, are provided. For example, compositions comprising PlyPH, or PlyPH in combination with the phage lysin PlyG or other *B. anthracis* killing agents, are described herein.

Methods and compositions relating to the diagnosis and treatment of *B. anthracis* infection or colonization are also provided. Furthermore, methods and compositions for the decontamination of anthrax are also provided. For example, sprayable compositions comprising PlyPH, either alone or in combination with PlyG or other antibacterial agents, can be used for decontamination of *B. anthracis*.

BRIEF DESCRIPTION OF THE DRAWINGS

FIG. 1 shows polypeptide sequences for certain bacteriophage lysins for *Bacillus anthracis*.

FIG. 2 is a graph showing a comparison of the lytic activities of *Bacillus anthracis* lysogenic phage lysins with that of PlyG expressed in *E. coli* XL1-Blue by OD assays of *B. cereus* 4342.

FIG. 3 shows the results of a purification of PlyPH on a cation exchange column.

FIG. 4 shows an alignment of the amino acid sequence of the *B. anthracis* lysogenic phage lysin PlyPH with lysins from three other *Bacillus* bacteriophages.

FIG. 5 shows an alignment of the amino acid sequences of PlyPH and PlyG phage lysins.

FIG. 6 is a graph showing specific lytic activities of PlyPH (BA2805) and PlyG.

FIGS. 7A, 7B, 7C and 7D are thin section transmission electron micrographs of *B. cereus* 4342 exposed to the PlyPH enzyme.

FIG. 8 is a graph showing PlyPH activity at different pH conditions.

FIG. 9 is a graph showing the effect of increasing salt concentrations on PlyPH activity.

FIG. 10 is a graph showing the temperature profile of PlyPH activity.

FIG. 11 is a graph showing the range of activity of PlyPH against various bacterial strains.

FIG. 12A is a graph showing the specificity of PlyPH lytic action on a mixture of *Bacillus* strains by the detection of ATP release through luciferin/luciferase luminescence.

FIG. 12B is a graph showing the specificity of PlyPH lytic action on a mixture of *Bacillus* strains by the indirect detection of ATP release through luciferin/luciferase luminescence.

FIG. 13A is a graph showing serum inhibition of PlyPH and PlyG.

FIG. 13B is a graph showing serum inhibition of PlyPH and PlyG.

FIG. 14 is a graph showing the survival rates of BALB/c mice infected with *B. cereus* 4342 through the intraperitoneal route, followed by treatment with buffer or PlyPH.

FIG. 15 is a graph showing the lytic activity of PlyPH on germinating *B. cereus* 4342 spores as a function of time.

FIG. 16 shows graphs from OD and viability assays experiments relating to the binding epitope of PlyPH on the surface of *B. cereus* 4342.

DETAILED DESCRIPTION

A definition of terms used and their applicability to the disclosure are provided below.

The term "isolated" means separated, and preferably purified, from a starting material. The term "purified" means that the biological material has been measurably increased in concentration by any purification process, including by not limited to, column chromatography, HPLC, precipitation, electrophoresis, etc., thereby partially, substantially or completely removing impurities such as precursors or other chemicals involved in preparing the material. Hence, material that is homogenous or substantially homogenous (e.g., yields a single protein signal in a separation procedure such as electrophoresis or chromatography) is included within the meanings of isolated and purified. Skilled artisans will appreciated that the amount of purification necessary will depend upon the use of the material. For example, compositions intended for administration to humans ordinarily must be highly purified in accordance with regulatory standards.

In this context of the embodiments, the term "lytic enzyme genetically coded for by a bacteriophage" means a polypeptide having at least some lytic activity against the host bacteria.

"Polypeptide" refers to a molecule comprised of natural or synthetic amino acids or amino acid derivatives. The polypeptide may include conservative substitutions wherein the naturally occurring amino acid is replaced by one having similar properties, where such conservative substitutions do not alter the function of the polypeptide (see, for example, Lewin "Genes V" Oxford University Press Chapter 1, pp. 9-13 1994).

"A native sequence phage associated lytic enzyme" is a polypeptide having the same amino acid sequence as an enzyme derived from nature. Such native sequence enzyme can be isolated from nature or can be produced by recombinant or synthetic means. The term "native sequence enzyme" specifically encompasses naturally occurring forms (e.g., alternatively spliced or modified forms) and naturally-occurring variants of the enzyme. In one embodiment of the disclosure, the native sequence enzyme is a mature or full-length polypeptide that is genetically coded for by a gene from a bacteriophage specific for *Bacillus anthracis*. Of course, a number of variants are possible and known, as acknowledged in publications such as Lopez et al., Microbial Drug Resistance 3: 199-211 (1997); Garcia et al., Gene 86: 81-88 (1990); Garcia et al., Proc. Natl. Acad. Sci. USA 85: 914-918 (1988); Garcia et al., Proc. Natl. Acad. Sci. USA 85: 914-918 (1988); Garcia et al., Streptococcal Genetics (J. J. Ferretti and Curtis eds., 1987); Lopez et al., FEMS Microbiol. Lett. 100: 439-448 (1992); Romero et at, J. Bacteriol. 172: 5064-5070 (1990); Ronda et al., Eur. J. Biochem. 164: 621-624 (1987) and Sanchez et al., Gene 61: 13-19 (1987). The contents of each of these references, particularly the sequence listings and associated text that compares the sequences, including statements about sequence homologies, are specifically incorporated by reference in their entireties.

Recitation of "SEQ ID Nos. 1-6" means "SEQ ID NO:1, SEQ ID NO:2, SEQ ID NO:3, SEQ ID NO:4, SEQ ID NO:5, or SEQ ID NO:6."

The term "effective amount" refers to an amount of an active ingredient sufficient to achieve a desired affect without causing an undesirable side effect. In some cases, it may be necessary to achieve a balance between obtaining a desired effect and limiting the severity of an undesired effect. It will be appreciated that the amount of active ingredient used will vary depending upon the type of active ingredient and the intended use of the composition of the present invention.

A "variant polypeptide sequence phage associated lytic enzyme" means a lytic enzyme genetically coded for by a bacteriophage specific for *Bacillus anthracis* having at least 50%, 55%, 60%, 65%, 70%, 75%, 80%, 85%, 90%, 95%, 97%, 98%, 99%, or even at least 99.5% amino acid sequence identity with a sequence described herein.

"Percent (%) polypeptide sequence identity" or "Percent (%) identity" with respect to the lytic enzyme polypeptide sequences identified herein is defined as the percentage of amino acid residues in a candidate sequence that are identical with the amino acid residues in the specific lytic enzyme polypeptide sequence, after aligning the sequences and introducing gaps, if necessary, to achieve the maximum percent sequence identity, and not considering any conservative substitutions as part of the sequence identity. Methods for alignment for purposes of determining percent amino acid sequence identity are described below.

Lysins Against *B. Anthracis*

The present disclosure provides various bacteriophage lysins with specific activity against *Bacillus anthracis*. Certain preferred bacteriophage lysin with specific activity against *Bacillus anthracis*, including PlyPH, were identified and characterized in a series of exemplary embodiments described below. Other embodiments provide lysins with specific activity against *B. anthracis*, which include variants of the lysins described herein.

Lysins generally occur in a modular structure. The N-terminal module consists of a catalytic domain believed to possess the ability to break down the bacterial cell wall of certain bacteria. Ezymatic activities often associated with the catalytic domain are amidases, endopeptidases, glucosamidases and muramidases. The C-terminal module consists of a binding domain that is believed to have an affinity for a carbohydrate epitope on the target bacteria cell wall. The binding domain is believed to determine the specificity of the lysin.

PlyPH is a prophage lysin that was originally identified in the *B. anthracis* Ames genome sequence and subsequently amplified from *B. anthracis* ΔSterne genomic DNA. More specifically, in the examples described below, the efficacy of PlyPH in killing *B. anthracis* and *B. anthracis*-like *B. cereus* was studied both in vitro and in vivo. The PlyPH lysin was cloned, purified and biochemically characterized, with its spectrum of activity examined against a range of bacterial species. The catalytic activity and binding affinity of the lysin were also investigated. The PlyPH *B. anthracis* phage lysin was also studied in combination with the phage lysin PlyG. PlyG was previously isolated from the γ phage and shown to have activity against *B. anthracis* (Schuch, R., D. Nelson, and V. A. Fischetti. 2002. A bacteriolytic agent that detects and kills *Bacillus anthracis*. Nature. 418:884-888, incorporated herein by reference in its entirety).

The embodiments disclosed here are not limited to the use of the PlyPH lytic enzyme. Indeed, any lytic enzyme genetically coded for by a bacteriophage which is specific for *Bacillus anthracis* and which itself is specific for *Bacillus anthracis*, may be used to identify and treat *Bacillus anthracis*, including SEQ ID NOs: 1-6 and polypeptide variants thereof (including fragments thereof). The polypeptide sequences of SEQ ID NOs: 1-6 (FIG. 1) are provided herein, as well as variants thereof.

The following references relating to the therapeutic application of lytic enzymes as an antibacterial agent are incorporated herein by reference in their entirety: Broudy, T. B., and V. A. Fischetti. 2003. In vivo lysogenic conversion of Tox− *Streptococcus pyogenes* to Tox+ with lysogenic streptococci or free phage. Infect. Immun. 71:3782-3786; Cheng, Q., D. Nelson, S. Zhu, and V. A. Fischetti. 2005. Removal of group B streptococci colonizing the vagina and oropharynx of mice with a bacteriophage lytic enzyme. AntimicroB. Agents Chemother. 49:111-117; Fischetti, V. A. 2003. Novel method to control pathogenic bacteria on human mucous membranes. Ann. N.Y. Acad. Sci. 987:207-214; Fischetti, V. A. 2001. Phage antibacterials make a comeback. Nature Biotechnol. 19:734-735; Koehler, T. M. 2000. *Bacillus anthracis*., p. 519-528. In V. A. Fischetti, R. P. Novick, J. J. Ferretti, D. A. Portnoy, and J. I. Rood (ed.), Gram-positive pathogens. American Society for Microbiology, Washington, D.C.; Loeffler, J. M., D. Nelson, and V. A. Fischetti. 2001. Rapid killing of *Streptococcus pneumoniae* with a bacteriophage cell wall hydrolase. Science. 294:2170-2172; Loeffler, J. M., S. Djurkovic, and V. A. Fischetti. 2003. Phage lytic enzyme Cpl-1 as a novel antimicrobial for pneumococcal bacteremia. Infect. Immun. 71:6199-6204; and Nelson, D., L. Loomis, and V. A. Fischetti. 2001. Prevention and elimination of upper respiratory colonization of mice by group A streptococci by using a bacteriophage lytic enzyme. Prot. Natl. Acad. Sci. USA. 98:4107-4112.

The present disclosure provides various preferred lysins with one or more particularly desirable characteristics. Preferred lysins such as PlyPH can be highly specific for *B. anthracis* ΔSterne and *B. cereus* strain 4342 which possesses *B. anthracis*-like properties. In one embodiment, a preferred lysin such as PlyPH can be cloned from the genome of *B. anthracis* ΔSterne and purified by cation exchange chromatography. Preferrably, a preferred lysin, including PlyPH, is durable enough to retain catalytic activity under various conditions. For example, one embodiment provides preferred lysins, such as PlyPH, that are thermostable up to an hour at 60° C. Preferred lysins can, in one embodiment, possess enhanced activity with the addition of salt up to 50 mM, 200 mM or 500 nM NaCl. Most preferably, lysins such as PlyPH retain lytic activity to various degrees between pH values of 4 and 12, with maximal activity between pH 4.5 and 8. Another embodiment provides combinations of lysins, such as PlyPH and PlyG, or combinations of other phage lysins with specificity for *B. anthracis*. Preferably the combination of two or more lysins results in an enhanced killing effect than either enzyme used alone. In one embodiment, a lysin (such as PlyG) is highly thermostable, preferably retaining 100% of its lytic activity after an incubation of 3 months at 40° C. Combinations of lysins, such as PlyG and PlyPH, are provided, for example to use as reagents for decontamination applications.

Additionally, other specific phage associated lytic enzymes specific for other bacteria may be included with a composition containing or comprising any phage associated lytic enzyme specific for *Bacillus anthracis*. For example, PlyG is a phage lysin isolated from the γ ("gamma") phage that specifically infects *B. anthracis* and *B. anthracis*-like strains. PlyG is a potential therapeutic agent in the treatment of anthrax infections, and anthrax decontamination. The polypeptide sequence corresponding to PlyG is provided in SEQ ID NO:2 (FIG. 1). The gamma phage of *Bacillus anthracis* can also be used as a *B. anthracis* lysin, for example in combination with PlyPH. Brown, E. R. & Cherry, W. B. "Specific identification of *Bacillus anthracis* by means of a variant bacteriophage," J Infect Dis 96, 34-9 (1955) The gamma phage infects >85% of all *Bacillus anthracis* isolates, including some closely related but rare *B. cereus* strains that could act as an environmental reservoir of potential anthracis progenitors. Turnbull, P. C. B. Definitive identification of *Bacillus anthracis* a review. J Appl Microbiol 87, 237-40 (1999). The gamma phage can be isolated, for example, from *Bacillus anthracis* obtained from Hans W. Ackermann (Laval University, Quebec, Canada). A high titer phage stock containing $2.2\times10^{10}$ plaque forming units (pfu)/mL can be prepared using RSVF1 by a previously described method (Loeffler, J. M., Nelson, D. & Fischetti, V. A. Rapid killing of *Streptococcus pneumoniae* with a bacteriophage cell wall hydrolase. Science 294, 2170-2 (2001)). A pfu is a single phage that forms a small clearing zone, or plaque, after successive rounds of infection, growth, and release on lawns of susceptible bacteria.

Cloning of Phage Lysins from *Bacillus* Bacteriophages

A genomic DNA library of ϕW2, a *Bacillus* phage isolated from a Pennsylvania soil sample, was generated using the adapter amplified shotgun expression libraries (AASEL) technique (see Examples). A positive clone identified by its lysis of overlaid *B. cereus* strain 4342 was sequenced. Interestingly, the DNA sequence revealed a protein whose amino acid sequence was practically identical to that of PlyG, the lysin from the *B. anthracis* gamma phage (Schuch, R., D. Nelson, and V. A. Fischetti, "A bacteriolytic agent that detects and kills *Bacillus anthracis*," *Nature* 418, 884-888 (2002)). One amino acid difference between PlyG and the ϕW2 lysin is found at position 91. PlyG harbors an isoleucine residue while the ϕW2 lysin contains a valine residue at that position, both hydrophobic amino acids. Surprisingly, a PlyG mutant named PlyG1 isolated from a mutagenesis screen of plyG passaged through the *E. coli* XL1-Red strain contained the identical 191V mutation, resulting in a sequence that is identical to that of the ϕW2 lysin.

Five lysogenic phage lysins were identified from sequenced *B. anthracis* genomes, and amplified by PCR using *B. anthracis* ΔSterne strain genomic DNA as the template. All five ORFs were successfully amplified and cloned into pBAD24. The five putative lysogenic phage lysin open reading frames were selected for cloning by performing a BLAST search against four *B. anthracis* strains on the NCBI website using PlyG (SEQ ID NO:2), the lysin from the *B. anthracis* γ phage, as the query sequence (Schuch, R., D. Nelson, and V. A. Fischetti, "A bacteriolytic agent that detects and kills *Bacillus anthracis*," *Nature* 418, 884-888 (2002), incorporated herein by reference). The *B. anthracis* genomes searched included the 'Ames Ancestor', Ames, A2012 and ΔSterne strains. The ORFs selected were PlyPH (SEQ ID NO:1), BA3767 (SEQ ID NO:3), BA2446 (SEQ ID NO: 4), BA4073 (SEQ ID NO:5) and BA3737 (SEQ ID NO:6), nomenclature based on the *B. anthracis* Ames strain. Although the names used for these ORFs correspond to the *B. anthracis* Ames strain, they were amplified by PCR using DNA from the attenuated *B. anthracis* ΔSterne strain. All ORFs were directionally cloned into pBAD24.

Expression and Purification of *B. Anthracis* Lysogenic Phage Lysins

All five clones of *B. anthracis* lysogenic phage lysins were induced for 4 hours with arabinose, and the chloroform extracted lysates tested for lytic activity against *B. cereus* 4342 by the OD assay. A pBAD18 clone expressing PlyG was induced in parallel, for comparison of its lytic activity with those of the putative lysogenic phage lysins.

FIG. 2 shows a 30 minute OD assay of lysates from all induced clones against *B. cereus* 4342. All clones were induced for 4 hours at 37° C. One hundred microliters of *B. cereus* 4342 suspension was mixed with an equal volume of each cell lysate with changes in optical density at 600 nm monitored on an automated spectrophotometer over 30 minutes, with readings taken every 15 seconds. Each lysin is labeled in FIG. 2. Of the five putative *B. anthracis* lysogenic phage lysins, three were selected for purification from cell lysates by ion exchange chromatography. BA4073 (SEQ ID NO:5) was not chosen as it is very similar to PlyG, with about 82% amino acid sequence identity throughout the length of both proteins, while BA3737 (SEQ ID NO:6) was not chosen as it had the slowest rate of *B. cereus* 4342 lysis as judged by OD analysis (FIG. 2).

The three selected proteins, PlyPH (SEQ ID NO:1), BA3767 (SEQ ID NO:3) and BA2446 (SEQ ID NO:4), have predicted pI's of 5.85, 6.15 and 6.96 respectively. Therefore, these proteins would be expected to adhere to an anion exchange column (HiTrap Q FF) when applied with a running buffer at pH 7.4, however they did not. Both PlyPH and BA3767 lytic activities were retrieved from the column flow through, while BA2446 lytic activity was neither isolated from the flow through nor salt gradient elution fractions.

Purification of lysates containing PlyPH and BA3767 were attempted through a cation exchange column (HiTrap SP HP) with a buffer at pH 5.5. While both proteins bound to the cation exchange column and were successfully eluted by increasing salt concentration, BA3767 eluted over a large number of fractions, across salt concentrations ranging from approximately 125 to over 500 mM, and over 2 distinct protein peaks (not shown). In contrast, PlyPH eluted in a single protein peak centered around 210 mM NaCl. This purification step resulted in PlyPH that is estimated to be over 90% pure (FIG. 3). PlyPH exhibited the highest lytic efficiency against *B. cereus* 4342 by the OD assay among the three proteins.

Referring again to FIG. 3, selected lytic enzymes were purified from the lysate of *E. coli*/pBAD24-plyPH through a cation exchange column on fast performance liquid chromatography (FPLC). This resulted in a semi-pure lysin fraction (arrow in FIG. 3 indicates the PlyPH fraction corresponding to about 30 kDa). The PlyPH enzyme was expressed from *E. coli* XL1-Blue/pBAD24-EF2805 by induction with arabinose for 4 hours. The cell lysate was purified through cation exchange columns (Hi Trap SP HP, Amersham Biosciences). Elution fractions containing lysin activity were pooled and subjected to separation by sodium dodecyl sulfate-polyacrylamide gel electrophoresis (SDS-PAGE). PlyPH has a predicted molecular weight of about 30 kDa. Its position of migration is indicated by the arrow.

Comparison of PlyPH and Other Phage Lysins

The PlyPH gene was identified from a BLAST search of *B. anthracis* genomes using the amino acid sequence of another known *B. anthracis* phage lysin, PlyG (SEQ ID NO:2), as the query sequence. Then the PlyPH gene was cloned into an *E. coli* expression vector, pBAD24, inducible by arabinose. The resulting plasmid was designated pBAD24-plyPH. A BLAST search conducted with the PlyPH amino acid sequence (SEQ ID NO:1) identified a number of *Bacillus* phage lysins with a high degree of sequence identity. Those phages include LambdaBa04, a lysogenic phage within *B. anthracis*; phBC6A52, a *B. cereus* phage; and Bam35c, a *B. thuringiensis* phage. An alignment of PlyPH (SEQ ID NO:1) with these lysins is shown in FIG. 4. Identical residues are highlighted by the darkest boxes, while conserved residues are not highlighted. Residues without significant conservation are highlighted by gray boxes.

The amino acid sequences of the phage lysins PlyPH (SEQ ID NO:1) and PlyG (SEQ ID NO:2) were aligned as shown in FIG. 5. The alignment shows extensive sequence identity in the carboxy terminal half of the protein sequence where the binding domains lie. However, there is little sequence identity in the amino terminal portion of the proteins suggesting that the catalytic domains differ although both were annotated as putative amidases, possibly belonging to different families of amidases. The extensive sequence identity in the carboxy terminal portions of both lysins suggests that they may bind the same epitope on the surface of a target bacteria such as *Bacillus anthracis* or similar bacteria. Identical residues are highlighted by black boxes, while conserved residues are highlighted with gray boxes.

The specific activities of PlyPH and PlyG were compared by incubating an equal amount of each enzyme with *B. cereus* 4342 in viability assays. The specific activities of PlyPH and PlyG at 30 μg each were comparable, decreasing *B. cereus* 4342 viability by approximately $2\times10^4$ CFU after 15 minutes (FIG. 6). When PlyPH and PlyG were combined and tested at 15 μg each, it decreased *B. cereus* 4342 viability by $6\times10^4$ CFU, showing a slightly enhanced effect as compared with PlyPH or PlyG alone. One hundred microliters of *B. cereus* 4342 suspension was mixed with either an equal volume of purified PlyPH or purified PlyG, each containing 30 μg of protein. Also, *B. cereus* 4342 was mixed with both PlyPH and PlyG at 15 μg each. The viability assays were incubated at room temperature for 15 minutes before plating on BHI agar for viability counts. The effect of the lysins individually and together on *B. cereus* 4342 viability is represented as fold killing. This data was gathered from three independent experiments.

Analysis of the Lytic Activity of PlyPH Under Different Conditions

PlyPH was exposed to a range of different biochemical conditions, including pH, temperature and salinity, to determine the conditions optimal to its activity against *B. anthracis*.

Despite the multiple assays employed indicating that the PlyPH enzyme exerts a lytic effect on *B. cereus* 4342, in order to view the direct effect of PlyPH on *B. cereus*, the reactions were captured by thin section transmission electron microscopy (FIG. 7). The election micrographs illustrate the bacterial cytoplasm extruding from the cell at points (see arrows) of the cell wall that have been weakened by the lytic action of PlyPH. PlyPH at various concentrations were incubated with *B. cereus* 4342 for 1 minute, followed by the addition of a fixative to stop the reactions. Microscopy was carried out by the Rockefeller University Bio-Imaging Resource Center.

PlyPH activity against *B. cereus* RSVF1 was tested in buffers between pH values of 2 and 12, with killing activity at each pH indicated in FIG. 8. PlyPH activity against *B. cereus* strain 4342 in buffers between pH values of 2 and 12 were tested. All reactions were incubated at room temperature for 15 minutes, followed by plating on BHI agar plates for viability counts. PlyPH was exposed to *B. cereus* 4342 suspended in buffers of varying pH values for 15 minutes prior to plating for viability counts. At the end of the incubation, the pH of each reaction was rechecked with narrow range pH paper. The killing efficiency of PlyPH at a particular pH value was represented as the ratio of *B. cereus* 4342 viability at that pH value to *B. cereus* 4342 viability after exposure to the PlyPH enzyme at the same pH value. PlyPH was found to work at 100% efficiency between the pH of 4.5 and 8, while still maintaining partial activity at pH 4, 9, 10 11 & 12 (FIG. 8). Typically, lysins are most active between pH 5 and 7 with activity tapering rapidly beyond those values. These are believed to be the first lysins described to be active in such a wide pH range.

Preferably, in one embodiment, a composition comprises PlyPH at a pH of about 4.0, 5.0, 6.0, 7.0, 8.0, 9.0, 10.0, 11.0, 12.0, or any pH interval of 0.05 therebetween, or any interval that is a multiple of 0.05 therebetween, including pH values of 4.5, 7.3 or 8.5.

As an increase in salt concentration has been found to enhance the activity of some other phage lysins, testing was conducted to determine if this was also true for PlyPH. The lytic efficiency of PlyPH at a particular salt concentration was measured by the decrease of *B. cereus* 4342 viability as compared to a parallel reaction where PBS was added instead of PlyPH. The results are represented graphically as fold killing of *B. cereus* 4342 in FIG. 9. Various amounts of a 5M sodium chloride stock solution was added to *B. cereus* RSVF1-PlyPH lytic assays, with lytic effects measured by 15 minute viability assays. A control reaction with no sodium chloride added was also measured, in addition to reactions with NaCl added to 50 mM, 200 mM and 500 mM. The addition of 50 mM and 200 mM NaCl to *B. cereus* 4342-PlyPH viability assays resulted in slightly enhanced killing of *B. cereus* compared with the reaction where no salt was added. However, the addition of 500 mM NaCl to a *B. cereus* 4342-PlyPH viability assay reduced the lytic effect of PlyPH by about half a log (FIG. 9).

Preferably, in one embodiment, a composition comprises PlyPH at a salt concentration of about 0.9% salt (sodium chloride). Other embodiments provide compositions comprising PlyPH in a sodium and/or chloride concentration of about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 340, 350, 360, 370, 380, 390, 400, 410, 420, 430, 440, 450, 460, 470, 480, 490, 500 mM or greater, more preferably between about 50 mM and about 500 mM, including intervals of 1 mM therebetween, and most preferably between about 100 mM and about 300 mM, including about 200 mM.

As shown in FIG. 10, PlyPH was incubated at various temperatures for 1 hour, followed by its exposure to *B. cereus* strain 4342 in 15 minute activity assays. PlyPH retains 100% of its lytic activity when incubated at temperatures between 4° C. and 60° C. for 1 hour prior to testing with *B. cereus* 4342, as confirmed by viability assays (FIG. 10). However, PlyPH is almost completely inactivated after incubation at 65° C. for 1 hour.

Preferably, in one embodiment, a composition comprising PlyPH at a pH at a temperature of between about 5° C. and 60° C., including 10, 15, 20, 25, 30, 35, 40, 45, 50, and 55° C., or any temperature interval of 1° C. therebetween, or any interval that is a multiple thereof therebetween, including temperatures of about 25° C. and about 37° C.

Specificity of PlyPH Action

The lytic activity of PlyPH (SEQ ID NO:1) appears to be highly specific towards *B. anthracis* ΔSterne and *B. cereus* 4342 when compared to other *Bacillus* strains tested, including other strains of *B. cereus* and *B. thuringiensis* (FIG. 11). Its range of activity against other *Bacillus* strains is identical to that of PlyG (SEQ ID NO:2). See, e.g., Schuch, R., D. Nelson, and V. A. Fischetti. 2002. A bacteriolytic agent that detects and kills *Bacillus anthracis*. Nature. 418:884-888, incorporated herein by reference in its entirety. Referring to FIG. 11, all *Bacillus* strains were grown in BHI liquid media for 3 hours with gyratory shaking at 30° C., washed and suspended in PBS at half the original culture volume. One hundred microliters of each *Bacillus* strain suspension was added to 100 μL of purified PlyPH at 300 μg/mL or 40 units/mL. In control experiments, PBS was used instead of PlyPH. All reactions were incubated at 15 minutes at room temperature, followed by immediate serial dilutions and plating on BHI agar for viability counts. The lytic effect of PlyPH was calculated as the ratio of *Bacillus* viability incubated with PBS to viability upon incubation with PlyPH.

PlyPH specificity for *B. anthracis* ΔSterne and *B. anthracis*-like *B. cereus* 4342 was established when applied to each strain individually. In order to confirm PlyPH specificity for *B. cereus* 4342 in a mixture of bacteria, a luminescent assay was used in the detection of bacterial lysis. In addition to corroborating the specificity of PlyPH for *B. cereus* 4342 in assays with individual bacterial strains, these experiments also demonstrate that PlyPH is able to selectively kill *B. cereus* 4342 in a mixture of bacteria (FIG. 12A). This property sets it apart from other bacteriocidal agents, like BRA, which generally have a broad spectrum of activity and kills non-discriminately (FIG. 12B).

Fifty microliters of each diluted bacterial suspension was applied to a Filtravette and washed twice with SRA. In graph A, 50 μL of PlyPH at 10 units/mL was added, followed by 50 μL of the luciferin/luciferase solution. In graph B, BRA was added instead of PlyPH. In both experiments, luminescence was measured in relative light units (RLU) on a microluminometer after a 1 minute incubation. Each reaction and luminescent reading was carried out in duplicate.

PlyPH Activity in the Presence of Rabbit Serum

A Western blot of purified PlyPH using antisera from PlyG immunized rabbits confirmed cross reactivity between both lysins. Dilutions of both the PlyG preimmune and hyperimmune rabbit sera added to PlyPH viability assays inhibited the lytic activity of PlyPH. However, the inhibition was comparable between the preimmune and hyperimmune sera reactions (FIG. 13A). An identical experiment carried out with PlyG instead of PlyPH demonstrated similar inhibition of PlyG by both preimmune and hyperimmune sera (FIG. 13B). These results indicate that some component in serum, even preimmune serum seems to affect the activities of PlyPH and PlyG. It also suggests that the overall serum inhibition effect was not the result of neutralizing antibodies. To test serum inhibition of lysins, 50 μL of PlyPH or PlyG at 800 μg/mL protein, or 128 units/mL lytic activity was incubated with 50 μL of each serum dilution for several minutes prior to the addition of 100 μL of *B. cereus* 4342 suspension. The assays were incubated at room temperature for 15 minutes, followed by plating on BHI agar for *B. cereus* viability counts. FIG. 13A shows the effect of preimmune and hyperimmune rabbit sera on PlyPH activity, while FIG. 13B shows the effect of preimmune and hyperimmune rabbit sera on PlyG activity. The effects were measured by differences in viability of *B. cereus* 4342 compared with control reactions. The starting *B. cereus* counts prior to the addition of serum or lysin (starting bact counts), and a *B. cereus*-lysin assay in the absence of serum (no ab added) served as controls. Five sets of serum dilutions are represented in the center, with 1 being undiluted, 2 being a two-fold dilution in PBS and so on. The effects of preimmune sera are represented in grey, while the effects of hyperimmune sera are represented in black.

Binding Epitope Analysis

Structurally, lysins are commonly found as modular proteins with an amino terminal domain that confers the enzymatic activity for a peptidoglycan bond and a carboxy terminal domain that confers binding specificity to a carbohydrate epitope in the bacterial cell wall. PlyPH was found to bind a carbohydrate epitope on the surface of *Bacillus*. Characterization of this carbohydrate binding epitope suggests that the carbohydrate epitope is not homogenous. The carbohydrate epitope is believed to be part of a larger complex, or a carbohydrate moiety with variable side chains.

The identification of the binding epitope of PlyPH would also likely elucidate the binding epitope of PlyG, since both enzymes are proposed to bind the same epitope. Since both lysins are highly specific for *B. anthracis*, and *B. anthracis*-like strains, the identification of a *B. anthracis* specific epitope would be valuable, for example, in the development of a highly specific antibacterial target. PlyPH and PlyG are hypothesized to bind the same carbohydrate epitope on the surface of *B. cereus* 4342 due to the extensive sequence identity in their binding domains and antisera cross reactivity. Although some binding epitope experiments below were carried out using PlyG instead of PlyPH, it is believed that information gathered from those experiments may be extrapolated to PlyPH.

Plaque assays of *Bacillus* phages gamma, W2 and W3 in the presence and absence of the *B. cereus* 4342 surface extracted carbohydrates were carried out as described in Example 13. The numbers of plaques were identical in both experiments, suggesting that PlyPH binds a different bacterial receptor than that of these three *Bacillus* phages. Using a series of increasing molecular weight filter units, information on the size of the inhibitory *B. cereus* 4342 surface carbohydrate component/s could be garnered. The PlyPH inhibitory carbohydrate component/s was unambiguously larger than 30 kDa, as evidenced by the inhibitory activity being detected in the retentate, but not the filtrate of the 30 kDa cutoff unit (not shown). However, the separation of carbohydrates through 50 and 100 kDa cutoff membranes revealed inhibitory activity in all fractions smaller than 50 kDa and larger than 100 kDa. Treatment of the extracted carbohydrates with trypsin does not alter the results obtained, implying that the inhibitory component, while shown not to be proteinaceous in nature, is not likely to be conjugated to protein either. While there is definitive evidence that the inhibitory carbohydrate component/s is larger than 30 kDa, it is not homogenous in size and ranges from 30 kDa to in excess of 100 kDa.

The separation of *B. cereus* 4342 surface carbohydrates by gel filtration yielded 48 elution fractions, each containing 0.75 mL. After an initial run, every other elution fraction was tested for inhibition of PlyPH activity, with none of the fractions tested exhibiting inhibition. Instead, only upon the pooling and concentration of all elution fractions did the inhibitory effect of PlyPH become restored. Due to the heterogeneous size of the inhibitory carbohydrate fragments, they likely eluted off the column over a large number of fractions, diluting it beyond the limits of detection in PlyPH inhibitory assays.

In a subsequent run, groups of 5 or more fractions were pooled, lyophilized and concentrated prior to testing of each group of fractions for the inhibition of PlyPH activity. Fractions 13 through 17 combined, which contained eluted fragments with estimated molecular weight between 40 to over 200 kDa, inhibited PlyPH activity more than any other sample (results not shown). This is consistent with the previously estimated size range of the PlyPH inhibitory carbohydrate fragments.

A PlyG affinity column, generated by the coupling of PlyG to cyanogen bromide-activated column was used in an attempt to purify the PlyG carbohydrate binding epitope. Despite extended incubation of the *B. cereus* 4342 extracted carbohydrates with the PlyG conjugated beads, the carbohydrates did not seem to bind the beads, as the lysin inhibitory activity remained solely in the column flow through fractions. The conjugation of PlyG to the matrix appeared to have been successful as judged by a dramatic decrease in protein concentration post conjugation. The use of buffers with extreme pH required by the coupling protocol for the removal of excess ligand may have denatured PlyG, which in turn may have affected its ability to bind its target carbohydrate epitope.

The PlyG digested *B. cereus* 4342 cell walls were separated through a gel filtration column. Fractions 20 and 21 from duplicate cell wall separations consistently inhibited the activity of PlyPH. These fractions coincided with a UV absorbance peak estimated to be at about 20 kDa when compared with molecular weight size standards run previously through the same column. Since the molecular weight of trypsin is 23.8 kDa, the inhibition of PlyPH as a result of the action of trypsin digesting PlyPH needed to be ruled out. Inhibition assays with fractions 20 and 21 were repeated with *B. cereus* 4342-PlyPH in the presence of the trypsin inhibitor leupeptin. The inhibition of PlyPH activity did not change in the presence of leupeptin, suggesting that it was due to a cell wall fragment and not the degradative action of trypsin.

Fractions 20 and 21 from two gel filtration separation procedures were pooled and sent for monosaccharide composition analysis by gas-liquid chromatography/mass spectrophotometry by a company named M-Scan. They reported very low levels of galactose, glucose, mannose and xylose in the submitted sample that was deemed likely to be insignificant. A mixture of these sugars at 12.5 μg./mL each did not inhibit PlyPH activity.

The carbohydrates on the surface of *B. anthracis* may be identified to compose predominantly of N-acetylglucosamine, N-acetylmannosamine and galactose. In order to determine if PlyPH could bind these monosaccharides, solutions of these monosaccharides either alone or in combination, were tested for inhibition of PlyPH lytic action against *B. cereus* 4342. Non-acetylated glucosamine and mannosamine were tested as well. None of the monosaccharide combinations inhibited PlyPH lytic activity, suggesting that PlyPH does not bind these monomers individually. This result was not surprising considering the large size of the inhibitory carbohydrate fragment (see above), but it seems possible these sugars may be present within the larger complex.

Treatment of intact *B. cereus* 4342 with pronase did not affect the ability of PlyPH to lyse it, confirmed by both OD and viability assays (FIG. 16 and Example 13). However, the addition of sodium periodate to *B. cereus* 4342 eliminated the lytic effect of PlyPH on that strain as analyzed by the OD assay (FIG. 16). These results suggests that the binding epitope targeted by PlyPH is carbohydrate and not proteinaceous. The carbohydrate nature of the epitope was further confirmed by the ability of surface carbohydrates from the *B. cereus* 4342 cell wall, removed by a nitrous acid extraction method, to inhibit PlyPH activity. Taken together, these results strongly suggest that PlyPH binds to a carbohydrate epitope in the *B. cereus* 4342 cell wall. The effect of PlyPH on pronase treated, sodium periodate ($NaIO_4$) treated and untreated *B. cereus* 4342 as observed by 15 minute OD assays are shown on the left panels. Control reactions with PBS instead of PlyPH are shown on the right panels. An inhibition assay of PlyPH lytic activity on *B. cereus* 4342 by 4342 extracted surface carbohydrates is shown on the bottom. Where viability assays were carried out, the bacterial counts after 15 minute incubation were listed adjacent to the corresponding reaction. The number below each graph is the $V_{max}$ value, which represents the change in optical density per unit time.

Mouse Model of *B. Cereus* 4342 Intraperitoneal Infection

In other embodiments, lysins provided herein are effective in ameliorating symptoms of infection in a mouse peritonitis model of infection with *B. cereus*. For example, in one embodiment, a mouse peritonitis model of infection with *B. cereus* 4342 demonstrated that about 40% of PlyPH treated mice recovering fully while 100% of buffer treated mice died within 38 hours. Accordingly, in one embodiment, the inhibition may partly be overcome by administrating higher concentrations of enzyme. The efficacy of PlyPH in vivo may suggest its possible application in the treatment of infections caused by *B. anthracis*. Most environmentally occurring strains of *B. anthracis* remain sensitive to most antibiotics. However, the window of treatment opportunity for exposed individuals is typically about 48 hours. Phage enzyme, used in combination with antibiotics, may extend the treatment window by controlling the growth of bacilli in the blood. In addition, *B. anthracis* has been shown to be able to acquire resistance to certain antibiotics with relative ease (Athamna, A., M. Athamna, N. Abu-Rashed, B. Medlej, D. J. Bast, and E. Rubinstein. 2004. Selection of *Bacillus anthracis* isolates resistant to antibiotics. J. AntimicroB. Chemother. 54:424-428; Bryskier, A. 2002. *Bacillus anthracis* and antibacterial agents. Clin. Microbiol. Infect. 8:467-478; Choe, C. H., S. S. Bouhaouala, I. Brook, T. B. Elliott, and G. B. Knudson. 2000. In vitro development of resistance to ofloxacin and doxycycline in *Bacillus anthracis* Sterne. AntimicroB. Agents Chemother. 44:1766; Stepanov, A. V., L. I. Marinin, A. P. Pomerantsev and N. A. Staritsin. 1996. Development of novel vaccines against anthrax in man. J. Biotechnol. 44:155-160). Should infections occur with a resistant strain of *B. anthracis* that cannot be treated by antibiotics, phage lysins may be considered as an alternative form of therapy.

The survival of BALB/c mice injected with *B. cereus* RSVF1 through the intraperitoneal route, then treated with buffer or PlyPH, was evaluated. Each BALB/c mouse was injected with a *B. cereus* 4342 PBS suspension containing approximately $2.5\times10^6$ CFU in 100 μL into the intraperitoneal cavity. About 10 minutes later, mice were either injected with 400 μL sterile buffer, or 400 μL purified and filter sterilized PlyPH containing an estimated 300 units/mL. PlyPH was able to rescue about 40% of mice completely, while 100% of buffer treated mice dead within 38 hours of infection (FIG. 14). The survival curves were significantly different (P<0.02).

Each mouse was injected with $2.5\times10^6$ CFU.100 $\mu L^{-1}$ of *B. cereus* 4342 in PBS into the intraperitoneal cavity, followed by injection 10 minutes later with 400 μL of either sterile buffer or purified PlyPH at 300 units/mL. This graph charts the survival of buffer and PlyPH treated mice over the initial 40 hour period post treatment. Thirteen mice were used in each group.

Lytic Effect of PlyPH of Germinating *Bacillus cereus* 4342 Spores

For the potential application of PlyPH in the decontamination of *B. anthracis*, PlyPH lytic activity against germinating spores was demonstrated. Spores of *B. cereus* 4342 were germinated using BHI broth containing L-alanine and inosine followed by exposure to the PlyPH enzyme with viability counts carried out. This was compared at every hour with a germinating spore suspension incubated with PBS instead. PlyPH was able to decrease the viability of germinating *B. cereus* 4342 spores by almost 3 logs after 5 hours (FIG. 15). A *B. cereus* 4342 spore preparation was heat activated by heating at 65° C. for 5 minutes. *B. cereus* 4342 spores were germinated using BHI containing 100 mM L-alanine and 1 mM inosine followed by exposure to the PlyPH enzyme at 3 mg/mL with samples taken every hour for viability counts. The lytic effect of PlyPH was compared with germinating spores incubated with PBS instead of PlyPH. A 1 in 10 dilution of the *B. cereus* 4342 spore preparation was heated to 95° C. for 5 minutes, killing all vegetative bacilli, while leaving the spore form unharmed. The viability counts before and after heat treatment, were 5.8×108 and 1.6×108 respectively. Therefore, the spore preparation contained about 30% of spores. Despite this low purity of spores, the decrease of *B. cereus* 4342 viability by almost 3-logs in 5 hours suggests that PlyPH had a significant lytic effect on germinating spores.

Variant Polypeptides

In addition to the lysins encoded by polypeptide sequences of SEQ ID NOs.: 1-6, the present disclosure also provides certain variant polypeptides, including fragments thereof and polypeptides with certain substitutions. The modified or altered form of the protein or peptides and peptide fragments, as disclosed herein, includes protein or peptides and peptide fragments that are chemically synthesized or prepared by recombinant DNA techniques, or both. These techniques include, for example, chimerization and shuffling. When the protein or peptide is produced by chemical synthesis, it is preferably substantially free of chemical precursors or other chemicals, i.e., it is separated from chemical precursors or other chemicals which are involved in the synthesis of the protein. Accordingly such preparations of the protein may have less than about 30%, 20%, 10%, or 5% (by dry weight) of chemical precursors or compounds other than the polypeptide of interest.

A "variant polypeptide sequence phage associated lytic enzyme" is preferably an active lytic enzyme polypeptide having at least about 80% amino acid sequence identity with a polypeptide sequence disclosed herein. Such lytic enzyme polypeptide variants include, for instance, lytic enzyme polypeptides wherein one or more amino acid residues are added, or deleted, at the N- or C-terminus of the full-length amino acid sequence. Preferably, a lytic enzyme polypeptide variant will have at least about 70% amino acid sequence identity, preferably at least about 75%, 80%, 81%, 82%, 83%, 84%, 85%, 86%, 87%, 88%, 89%, 90%, 91%, 92%, 93%, 94%, 95%, 96%, 97%, 98%, 99%, or 99.5% amino acid sequence identity with a full-length native sequence lytic enzyme polypeptide sequence as disclosed herein, a lytic enzyme polypeptide sequence lacking the signal peptide as disclosed herein, an extracellular domain of a lytic enzyme polypeptide, with or without the signal peptide, as disclosed herein or any other specifically defined fragment of a full-length lytic enzyme polypeptide sequence as disclosed herein. Preferably, lytic enzyme variant polypeptides are at least about 10 amino acids in length, often at least about 20, 30, 40, 50, 60, 70, 80, 90, 100, 150, 200 or 300 amino acids in length, or more.

Such phage associated lytic enzyme variants include, for instance, lytic enzyme polypeptides wherein one or more amino acid residues are added, or deleted at the N or C terminus of the sequences of SEQ ID Nos. 1-6. In an embodiment one or more amino acids are substituted, deleted, and/or added to any position(s) in the sequence, or sequence portion. "Percent amino acid sequence identity" with respect to the phage associated lytic enzyme sequences identified herein is defined as the percentage of amino acid residues in a candidate sequence that are identical with the amino acid residues in the phage associated lytic enzyme sequence, after aligning the sequences in the same reading frame and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, such as using publicly available computer software such as blast software.

Polypeptide alignment for purposes of determining percent amino acid sequence identity can be achieved in various ways that are within the skill in the art, for instance using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

The % amino acid sequence identity values may also be obtained as described below by using the WU-BLAST-2 computer program (Altschul et al., Methods in *Enzymology* 266:460-480 (1996)). Most of the WU-BLAST-2 search parameters are set to the default values. Those not set to default values are set with the following values: overlap span=1, overlap fraction=0.125, word threshold (T)=11, and scoring matrix=BLOSUM62. When WU-BLAST-2 is employed, a % amino acid sequence identity value is determined by dividing (a) the number of matching identical amino acid residues between the amino acid sequence of the lytic enzyme polypeptide of interest having a sequence derived from the native lytic enzyme polypeptide and the comparison amino acid sequence of interest (i.e., the sequence against which the lytic enzyme polypeptide of interest is being compared which may be a lytic enzyme variant polypeptide) as determined by WU-BLAST-2 by (b) the total number of amino acid residues of the lytic enzyme polypeptide of interest. For example, in the statement "a polypeptide comprising an the amino acid sequence A which has or having at least 80% amino acid sequence identity to the amino acid sequence B", the amino acid sequence A is the comparison amino acid sequence of interest and the amino acid sequence B is the amino acid sequence of the lytic enzyme polypeptide of interest.

Percent amino acid sequence identity may also be determined using the sequence comparison program NCBI-BLAST2 (Altschul et al., Nucleic Acids Res. 25:3389-3402 (1997)). The NCBI-BLAST2 sequence comparison program may be downloaded from http://www.ncbi.nlm.nih.gov. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction $X/Y$ where X is the number of amino acid residues scored as identical matches by the sequence alignment program NCBI-BLAST2 in that program's alignment of A and B, and where Y is the total number of amino acid residues in B. It will be appreciated-that where the length of amino acid sequence A is not equal to the length of amino acid sequence B, the % amino acid sequence identity of A to B will not equal the % amino acid sequence identity of B to A.

Lysin Fragments

In some embodiments, biologically active fragments of the lysins, including the polypeptide sequences such as SEQ ID NOs: 1-6 or variants thereof described herein, are provided. As used herein, a "fragment" is a variant polypeptide having an amino acid sequence that entirely is the same as part but not all of the amino acid sequence of the aforementioned polypeptides. A fragment may be "free-standing," or comprised within a larger polypeptide of which they form a part or region, most preferably as a single continuous region, a single larger polypeptide.

Biologically active portions of a protein or peptide fragment of the embodiments, as described herein, include polypeptides comprising amino acid sequences sufficiently identical to or derived from the amino acid sequence of the phage protein of the disclosure, which include fewer amino acids than the full length protein of the phage protein and exhibit at least one activity of the corresponding full length protein. Typically, biologically active portions comprise a domain or motif with at least one activity of the corresponding protein. A biologically active portion of a protein or protein fragment of the disclosure can be a polypeptide which is, for example, 10, 25, 50, 100 less or more amino acids in length. Moreover, other biologically active portions, in which other regions of the protein are deleted, or added can be prepared by recombinant techniques and evaluated for one or more of the functional activities of the native form of a polypeptide of the embodiments.

Fragments may include, for example, truncation polypeptides having a portion of an amino acid sequence corresponding to (e.g., 50% sequence identity, more preferably at least 60% more preferably, at least 70% sequence identity, more preferably at least 80% sequence identity, more preferably at least 95% sequence identity, more preferably at least 97% sequence identity and even more preferably at least or even 98% sequence identity of at least 50 amino acid long region of the Natural Binding Region, or of variants thereof, such as a continuous series of residues that includes the amino terminus, or a continuous series of residues that includes the carboxyl terminus. Degradation forms of the polypeptides of this embodiment in a host cell also are provided in some embodiments. Further provided are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions.

Also provided are fragments that have binding activities of at least $10^6$, $10^7$, $10^8$ or $10^9$ against *Bacillus anthracis*, including those with a similar activity or an improved activity, or with a decreased undesirable activity. Also advantageous are conjugates of binding site and a detectable tag or bacteriocidal tag that confers such desirable clinical function whereby the binding region specifically binds to the bacterial wall, allowing detection or killing of the anthracis.

Variants that are fragments of the polypeptides of the disclosure may be employed for producing the corresponding full-length polypeptide by peptide synthesis; therefore, these variants may be employed as intermediates for producing the full-length polypeptides of embodiments of the disclosure.

Lytic enzyme peptide fragments may be prepared by any of a number of conventional techniques. Desired peptide fragments may be chemically synthesized An alternative approach involves generating lytic enzyme fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired polypeptide fragment, by polymerase chain reaction (PCR). Oligonucleotides that define the desired termini of the DNA fragment are employed at the 5' and 3' primers in the PCR. Preferably, lytic enzyme polypeptide fragments share at least one biological and/or immunological activity with the native lytic enzyme polypeptide disclosed herein.

For example, libraries of fragments of the coding sequence of a polypeptide of the disclosure can be used to generate a variegated population of polypeptides for screening and subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N terminal and internal fragments of various sizes of the protein of interest. Several techniques are known in the art for screening gene products of combinatorial libraries made by point mutations or truncation, and for screening cDNA libraries for gene products having a selected property. The most widely used techniques, which are amenable to high through put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the disclosure (Arkin and Yourvan (1992) Proc. Natl. Acad. Sci. USA 89:7811 7815; Delgrave et al. (1993) Protein Engineering 6(3):327 331).

Immunologically active portions of a protein or peptide fragment can include regions that bind to antibodies that recognize the phage enzyme. In this context, the smallest portion of a protein (or nucleic acid that encodes the protein) according to embodiments is an epitope that is recognizable as specific for the phage that makes the lysin protein. Accordingly, the smallest polypeptide (and associated nucleic acid that encodes the polypeptide) that can be expected to bind antibody and is useful for some embodiments may be 8, 9, 10, 11, 12, 13, 15, 20, 25, 30, 35, 40, 45, 50, 55, 60, 65, 75, 85, or 100 amino acids long. Although small sequences as short as 8, 9, 10, 11, 12 or 15 amino acids long reliably comprise enough structure to act as epitopes, shorter sequences of 5, 6, or 7 amino acids long can exhibit epitopic structure in some conditions and have value in an embodiment. Thus, in some embodiments, the smallest portion of the protein described by SEQ ID Nos. 1-6 can includes polypeptides as small as 5, 6, 7, 8, 9, or 10 amino acids long.

Homologous proteins and nucleic acids can be prepared that share functionality with such small proteins and/or nucleic acids (or protein and/or nucleic acid regions of larger molecules) as will be appreciated by a skilled artisan. Such small molecules and short regions of larger molecules, that may be homologous specifically are intended as embodiments. Preferably the homology of such valuable regions is at least 50%, 65%, 75%, 85%, and more preferably at least 90%, 95%, 97%, 98%, or at least 99% compared to SEQ ID Nos. 1-6. These percent homology values do not include alterations due to conservative amino acid substitutions.

Of course, an epitope as described herein may be used to generate an antibody and also can be used to detect binding to molecules that recognize the lysin protein. Another embodiment is a molecule such as an antibody or other specific binder that may be created through use of an epitope such as by regular immunization or by a phase display approach where an epitope can be used to screen a library if potential binders. Such molecules recognize one or more epitopes of lysin protein or a nucleic acid that encodes lysin protein. An antibody that recognizes an epitope may be a monoclonal antibody, a humanized antibody, or a portion of an antibody protein. Desirably the molecule that recognizes an epitope has a specific binding for that epitope which is at least 10 times as strong as the molecule has for serum albumin. Specific binding can be measured as affinity (Km). More desirably the specific binding is at least $10^2$, $10^3$, $10^4$, $10^5$, $10^6$, $10^7$, $10^8$, or even higher than that for serum albumin under the same conditions.

In a desirable embodiment the antibody or antibody fragment is in a form useful for detecting the presence of the lysin protein. A variety of forms and methods for their synthesis are known as will be appreciated by a skilled artisan. The antibody may be conjugated (covalently complexed) with a reporter molecule or atom such as a fluor, an enzyme that creates an optical signal, a chemilumiphore, a microparticle, or a radioactive atom. The antibody or antibody fragment may be synthesized in vivo, after immunization of an animal, for example, The antibody or antibody fragment may be synthesized via cell culture after genetic recombination. The antibody or antibody fragment may be prepared by a combination of cell synthesis and chemical modification.

Variant Polypeptides

Substitutional variants are those in which at least one residue in the amino acid sequence has been removed and a different residue inserted in its place. Such substitutions may be made in accordance with the following Table 1 when it is desired to finely modulate the characteristics of the protein. Table 1 shows amino acids which may be substituted for an original amino acid in a protein and which are regarded as conservative substitutions.

TABLE 1

| Original Residue | Conservative Substitutions |
|---|---|
| Ala | ser |
| Arg | lys |
| Asn | gln, his |
| Asp | glu |
| Cys | ser |
| Gln | asn |
| Glu | asp |
| Gly | pro |
| His | asn; gln |
| Ile | leu, val |

TABLE 1-continued

| Original Residue | Conservative Substitutions |
|---|---|
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

Substantial changes in function or immunological identity are made by selecting substitutions that are less conservative than in Table 1, i.e., selecting residues that differ more significantly in their effect on maintaining: (a) the structure of the polypeptide backbone in the area of the substitution, for example, as a sheet or helical conformation; (b) the charge or hydrophobicity of the molecule at the target site; or (c) the bulk of the side chain. The substitutions which in general are expected to produce the greatest changes in protein properties will be those in which: (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine.

The effects of these amino acid substitutions or deletions or additions may be assessed for derivatives of the lytic protein by analyzing the ability of the derivative proteins to complement the sensitivity to DNA cross-linking agents exhibited by phages in infected bacteria hosts. These assays may be performed by transfecting DNA molecules encoding the derivative proteins into the bacteria as described above.

Substantial modifications in function or immunological identity of the lytic enzyme polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gin, his, lys, arg;
(5) residues that influence chain orientation: gly, pro; and
(6) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

Polypeptide variations can be made using methods known in the art such as oligonucleotide-mediated (site-directed) mutagenesis, alanine scanning, and PCR mutagenesis. Site-directed mutagenesis [Carter et al., Nucl. Acids Res., 13:4331 (1986); Zoller et al., Nucl. Acids Res., 10:6487 (1987)], cassette mutagenesis [Wells et al., Gene, 34:315 (1985)], restriction selection mutagenesis [Wells et al., Philos. Trans. R. Soc. London SerA, 317:415 (1986)] or other known techniques can be performed on the cloned DNA to produce the lytic enzyme variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, Science. 244: 1081-1085 (1989)]. Alanine is also typically preferred because it is the most common amino acid. Further, it is frequently found in both buried and exposed positions [Creighton, The Proteins, (W. H. Freeman & Co., N.Y.); Chothia, J. Mol. Biol. 150:1 (1976)]. If alanine substitution does not yield adequate amounts of variant, an isoteric amino acid can be used.

Chimeric Fusion Proteins

In some embodiments, a lytic enzyme may also be modified to form a chimeric molecule comprising lytic enzyme fused to another, heterologous polypeptide or amino acid sequence. A "chimeric protein" or "fusion protein" comprises all or (preferably a biologically active) part of a polypeptide of the disclosure operably linked to a heterologous polypeptide. Chimeric proteins or peptides are produced, for example, by combining two or more proteins having two or more active sites. Chimeric protein and peptides can act independently on the same or different molecules, and hence have a potential to treat two or more different bacterial infections at the same time. Chimeric proteins and peptides also are used to treat a bacterial infection by cleaving the cell wall in more than one location.

In one embodiment, such a chimeric molecule comprises a fusion of the lytic enzyme with a tag polypeptide which provides an epitope to which an anti-tag antibody can selectively bind. The epitope tag is generally placed at the amino- or carboxyl-terminus of the lytic enzyme. The presence of such epitope-tagged forms of the lytic enzyme can be detected using an antibody against the tag polypeptide. Also, provision of the epitope tag enables the lytic enzyme to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., Mol. Cell. Biol., 8:2159-2165 (1988)]; the c-myc tag and the 8F9, 3C7, 6E10, G4, B7 and 9E10 antibodies thereto [Evan et al., Molecular and Cellular Biology, 5:3610-3616 (1985)1; and the Herpes Simplex virus glycoprotein D (gD) tag and its antibody [Paborsky et al., Protein Engineering: (6):547-553 (1990)]. Other tag polypeptides include the Flag-peptide [Hopp et al., BioTechnology, 6:1204-1210 (1988)]; the KT3 epitope peptide [Martin et al., Science 255: 192-194 (1992)]; an α-tubulin epitope peptide (Skinner et al., J. Biol. Chem., 266:15163-15166 (1991)1; and the T7 gene 10 protein peptide tag (Lutz-Freyermuth et al., Proc. Natl. Acad. Sci. USA, 87:6393-6397 (1990)].

In an alternative embodiment, the chimeric molecule may comprise a fusion of the lytic enzyme with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a lytic enzyme polypeptide in place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995.

In another embodiment, the chimeric protein or peptide contains a heterologous signal sequence at its N terminus. For example, the native signal sequence of a polypeptide of the disclosure can be removed and replaced with a signal sequence from another protein. For example, the gp67 secretory sequence of the baculovirus envelope protein can be used as a heterologous signal sequence (Current Protocols in Molecular Biology, Ausubel et al., eds., John Wiley & Sons, 1992, incorporated herein by reference). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Sambrook et al., supra) and the protein A secretory signal (Pharmacia Biotech; Piscataway, N.J.). Another example of a useful fusion protein is a GST fusion protein in which the polypeptide of the disclosure is fused to the C terminus of a GST sequence. Such a chimeric protein can facilitate the purification of a recombinant polypeptide of the disclosure.

Another embodiment discloses an immunoglobulin fusion protein in which all or part of a polypeptide of the disclosure is fused to sequences derived from a member of the immunoglobulin protein family. An immunoglobulin fusion protein can be incorporated into a pharmaceutical composition and administered to a subject to inhibit an interaction between a ligand (soluble or membrane bound) and a protein on the surface of a cell (receptor), to thereby suppress signal transduction in vivo. The immunoglobulin fusion protein can alter bioavailability of a cognate ligand of a polypeptide of the disclosure. Inhibition of ligand/receptor interaction may be useful therapeutically, both for treating bacterial associated diseases and disorders for modulating (i.e. promoting or inhibiting) cell survival. Moreover, an immunoglobulin fusion protein of the disclosure can be used as an immunogen to produce antibodies directed against a polypeptide of the disclosure in a subject, to purify ligands and in screening assays to identify molecules which inhibit the interaction of receptors with ligands. Chimeric and fusion proteins and peptides of the disclosure can be produced by standard recombinant DNA techniques.

In another embodiment, the fusion gene can be synthesized by conventional techniques, including automated DNA synthesizers. Alternatively, PCR amplification of gene fragments can be carried out using anchor primers which give rise to complementary overhangs between two consecutive gene fragments which subsequently can be annealed and reamplified to generate a chimeric gene sequence (see, i.e., Ausubel et al., supra). Moreover, many expression vectors are commercially available that already encode a fusion moiety (i.e., a GST polypeptide). A nucleic acid encoding a polypeptide of the disclosure can be cloned into such an expression vector such that the fusion moiety is linked in frame to the polypeptide of the disclosure.

Combination with Signal Sequences

In one embodiment of the disclosure, a signal sequence of a polypeptide of can facilitate transmembrane movement of the protein and peptides and peptide fragments of the disclosure to and from mucous membranes, as well as by facilitating secretion and isolation of the secreted protein or other proteins of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the disclosure can pertain to the described polypeptides having a signal sequence, as well as to the signal sequence itself and to the polypeptide in the absence of the signal sequence (i.e., the cleavage products). In one embodiment, a nucleic acid sequence encoding a signal sequence of the disclosure can be operably linked in an expression vector to a protein of interest, such as a protein which is ordinarily not secreted or is otherwise difficult to isolate. The signal sequence directs secretion of the protein, such as from an eukaryotic host into which the expression vector is transformed, and the signal sequence is subsequently or concurrently cleaved. The protein can then be readily purified from the extracellular medium by art recognized methods. Alternatively, the signal sequence can be linked to a protein of interest using a sequence which facilitates purification, such as with a GST domain.

In another embodiment, a signal sequence can be used to identify regulatory sequences, i.e., promoters, enhancers, repressors. Since signal sequences are the most amino terminal sequences of a peptide, it is expected that the nucleic acids which flank the signal sequence on its amino terminal side will be regulatory sequences that affect transcription. Thus, a nucleotide sequence which encodes all or a portion of a signal sequence can be used as a probe to identify and isolate the signal sequence and its flanking region, and this flanking region can be studied to identify regulatory elements therein. The present disclosure also pertains to other variants of the polypeptides of the disclosure. Such variants have an altered amino acid sequence which can function as either agonists (mimetics) or as antagonists. Variants can be generated by mutagenesis, i.e., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein. Variants of a protein of the disclosure which function as either agonists (mimetics) or as antagonists can be identified by screening combinatorial libraries of mutants, i.e., truncation mutants, of the protein of the disclosure for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (i.e., for phage display). There are a variety of methods which can be used to produce libraries of potential variants of the polypeptides of the disclosure from a degenerate oligonucleotide sequence. Methods for synthesizing degenerate oligonucleotides are known in the art (see, i.e., Narang (1983) Tetrahedron 39:3; Itakura et al. (1984) Annu. Rev. Biochem. 53:323; Itakura et al. (1984) Science 198:1056; Ike et al. (1983) Nucleic Acid Res. 11:477, all herein incorporated by reference).

Shuffled Enzymes

Certain embodiments provide shuffled proteins or peptides comprising one or more lytic enzyme peptides or variants thereof disclosed herein, gene products, or peptides for more than one related phage protein or protein peptide fragments that are randomly cleaved and reassembled into a more active or specific protein. Shuffled oligonucleotides, peptides or peptide fragment molecules are selected or screened to identify a molecule having a desired functional property. This method is described, for example, in Stemmer, U.S. Pat. No. 6,132,970. (Method of shuffling polynucleotides); Kauffman, U.S. Pat. No. 5,976,862 (Evolution via Condon based Synthesis) and Huse, U.S. Pat. No. 5,808,022 (Direct Codon Synthesis). The contents of these patents are incorporated herein by reference. Shuffling is used to create a protein that is 10 to 100 fold more active than the template protein. The template protein is selected among different varieties of lysin or holin proteins. The shuffled protein or peptides constitute, for example, one or more binding domains and one or more catalytic domains. Each binding or catalytic domain is derived from the same or a different phage or phage protein. The shuffled domains are either oligonucleotide based molecules, as gene or gene products, that either alone or in combination with other genes or gene products are translatable into a peptide fragment, or they are peptide based molecules. Gene fragments include any molecules of DNA, RNA, DNA RNA hybrid, antisense RNA, Ribozymes, ESTs, SNIPs and other oligonucleotide based molecules that either alone or in combination with other molecules produce an oligonucleotide molecule capable or incapable of translation into a peptide.

Covalent Modification of Polypeptides

Other embodiments provide for covalent modifications of a lytic enzyme, or fragment or variant thereof. One type of covalent modification includes reacting targeted amino acid residues of a lytic enzyme polypeptide with an organic derivatizing agent that is capable of reacting with selected side chains or the N- or C-terminal residues of the lytic enzyme—Derivatization with bifunctional agents is useful, for instance, for crosslinking lytic enzyme to a water-insoluble support matrix or surface for use in the method for purifying anti-lytic enzyme antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl-)dithiolpropioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the $\alpha$-amino groups of lysine, arginine, and histidine side chains [T. E. Creighton, Proteins: Structure and Molecular Properties, W. H. Freeman & Co., San Francisco, pp 79-86 (1983)], acetylation of the N-terminal amine, and amidation of any C-terminal carboxyl group.

Another type of covalent modification of the lytic enzyme polypeptide provided herein comprises altering the native glycosylation pattern of the polypeptide. Altering the native glycosylation pattern is intended for purposes herein to mean deleting one or more carbohydrate moieties found in native sequence lytic enzyme (either by removing the underlying glycosylation site or by deleting the glycosylation by chemical and/or enzymatic means), and/or adding one or more glycosylation sites that are not present in the native sequence lytic enzyme. In addition, the phrase includes qualitative changes in the glycosylation of the native proteins, involving a change in the nature and proportions of the various carbohydrate moieties present.

Addition of glycosylation sites to the lytic enzyme polypeptide may be accomplished by altering the amino acid sequence. The alteration may be made, for example, by the addition of, or substitution by, one or more serine or threonine residues to the native sequence lytic enzyme (for O-linked glycosylation sites). The lytic enzyme amino acid sequence may optionally be altered through changes at the DNA level, particularly by mutating the DNA encoding the lytic enzyme polypeptide at preselected bases such that codons are generated that will translate into the desired amino acids.

Another means of increasing the number of carbohydrate moieties on the lytic enzyme polypeptide is by chemical or enzymatic coupling of glycosides to the polypeptide. Such methods are described in the art, e.g., in WO 87/05330 published Sep. 11, 1987, and in Aplin and Wriston, CRC Crit. Rev. Biochem., pp. 259-306 (1981).

Removal of carbohydrate moieties present on the lytic enzyme polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al, Arch. Biochem. Biophys., 259:52 (1987) and by Edge et al., Anal. Biochem., 118:131 (1981). Enzymatic cleavage of carbohydrate moieties on polypeptides can be achieved by the use of a variety of endo- and exo-glycosidases as described by Thotakura et al., Meth. Enzymol., 138:350 (1987).

Another type of covalent modification of lytic enzyme comprises linking the lytic enzyme polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

Han Proteins

The present disclosure also provides the use of holin proteins, for example in combination with one or more lytic enzyme peptides, or variants or fragments thereof. Holin proteins produce holes in the cell membrane. Holin proteins, or "holins," can form lethal membrane lesions. Like the lytic proteins, holin proteins are coded for and carried by a phage. Most holin protein sequences are short, and overall, hydrophobic in nature, with a highly hydrophilic carboxy terminal domain. In many cases, the putative holin protein is encoded on a different reading frame within the enzymatically active domain of the phage. In other cases, holin protein is encoded on the DNA next or close to the DNA coding for the cell wall lytic protein. Holin proteins are frequently synthesized during the late stage of phage infection and found in the cytoplasmic membrane where they cause membrane lesions.

Holins can be grouped into two general classes based on primary structure analysis. Class I holins are usually 95 residues or longer and may have three potential transmembrane domains. Class II holins are usually smaller, at approximately 65 95 residues, with the distribution of charged and hydrophobic residues indicating two TM domains (Young, et al. Trends in Microbiology v. 8, No. 4, March 2000). At least for the phages of gram positive hosts, however, the dual component lysis system may not be universal. Although the presence of holins has been shown or suggested for several phages, no genes have yet been found encoding putative holins for all phages. Holins have been shown to be present in several bacteria, including, for example, lactococcal bacteriophage Tuc2009, lactococcal NLC3, pneumococcal bacteriophage EJ 1, LactoBacillus gasseri bacteriophage Nadh, *Staphylococcus aureus* bacteriophage Twort, *Listeria monocytogenes* bacteriophages, pneumococcal phage Cp 1, *Bacillus subtillis* phage M29, LactoBacillus delbrueckki bacteriophage LL H lysin, and bacteriophage N11 of *Staphyloccous aureus*. (Loessner, et al., Journal of Bacteriology, August 1999, p. 4452 4460).

Polynucleotides

A lysin may be produced by any number of different methods. The lytic enzyme is produced by infecting said *Bacillus anthracis* with the genetic code delivered by a bacteriophage specific for said *Bacillus anthracis*. In another embodiment of the disclosure, the lytic enzyme is produced by recombinant production from a nucleic acid that comprises a DNA having the sequence of bases of a polynucleotide sequence coding for one or more polypeptides of SEQ ID Nos. 1-6, a polypeptide variant thereof (including polypeptide fragments) or a sequence that hybridizes with the complement of bases of a polynucleotide sequence coding for the polypeptide sequences of SEQ ID No. 1-6 or a polypeptide variant thereof (including polypeptide fragments) under suitable hybridization conditions. The lytic enzyme may be produced by removing a gene for the lytic enzyme from the phage genome, introducing said gene into a transfer vector, and cloning said transfer vector into an expression system, wherein the transfer vector is a plasmid. The expression system may be a bacteria, selected from any of the above listed groups, or, most preferably, from the group consisting of *E. coli* and *Bacillus*. In another expression system production of the enzyme is by cell free expression system.

In addition to the full-length native polynucleotide sequences encoding lytic enzyme polypeptides described herein, it is contemplated that lytic enzyme variants can be prepared. The degeneracy of the genetic code further widens the scope of the embodiments as it enables major variations in the nucleotide sequence of a DNA molecule while maintaining the amino acid sequence of the encoded protein. For example, a representative amino acid residue is alanine. This may be encoded in the cDNA by the nucleotide codon triplet GCT. Because of the degeneracy of the genetic code, three other nucleotide codon triplets—GCT, GCC and GCA—also code for alanine. Thus, the nucleotide sequence of the gene could be changed at this position to any of these three codons without affecting the amino acid composition of the encoded protein or the characteristics of the protein. The genetic code and variations in nucleotide codons for particular amino acids are well known to the skilled artisan. Based upon the degeneracy of the genetic code, variant DNA molecules may be derived from the cDNA molecules disclosed herein using standard DNA mutagenesis techniques as described above, or by synthesis of DNA sequences. DNA sequences which do not hybridize under stringent conditions to the cDNA sequences disclosed by virtue of sequence variation based on the degeneracy of the genetic code are herein comprehended by this disclosure.

Lytic enzyme variants can be prepared, for example, by introducing appropriate nucleotide changes into the lytic enzyme DNA, and/or by synthesis of the desired lytic enzyme polypeptide. Those skilled in the art will appreciate that amino acid changes may alter post-translational processes of the lytic enzyme, such as changing the number or position of glycosylation sites or altering the membrane anchoring characteristics.

One skilled in the art will recognize that the DNA mutagenesis techniques described here can produce a wide variety of DNA molecules that code for a bacteriophage lysin specific for *Bacillus anthracis* yet that maintain the essential characteristics of the lytic protein. Newly derived proteins may also be selected in order to obtain variations on the characteristic of the lytic protein, as will be more fully described below. Such derivatives include those with variations in amino acid sequence including minor deletions, additions and substitutions. While the site for introducing an amino acid sequence variation is predetermined, the mutation per se does not need to be predetermined. For example, in order to optimize the performance of a mutation at a given site, random mutagenesis may be conducted at the target codon or region and the expressed protein variants screened for the optimal combination of desired activity. Techniques for making substitution mutations at predetermined sites in DNA having a known sequence as described above are well known. Amino acid substitutions are typically of single residues; insertions usually will be on the order of about from 1 to 10 amino acid residues; and deletions will range about from 1 to 30 residues. Deletions or insertions may be in single form, but preferably are made in adjacent pairs, i.e., a deletion of 2 residues or insertion of 2 residues. Substitutions, deletions, insertions or any combination thereof may be combined to arrive at a final construct. Obviously, the mutations that are made in the DNA encoding the protein should not place the sequence out of reading frame and preferably will not create complementary regions that could produce secondary mRNA structure (EP 75,444A).

"Percent nucleic acid sequence identity" with respect to the phage associated lytic enzyme sequences identified herein is defined as the percentage of nucleotides in a candidate sequence that are identical with the nucleotides in the phage associated lytic enzyme sequence, after aligning the sequences and introducing gaps, if necessary, to achieve the maximum percent sequence identity. Alignment for purposes of determining percent nucleic acid sequence identity can be achieved in various ways that are within the scope of those skilled in the art, including but not limited to the use of publicly available computer software.

Having herein provided nucleotide sequences that code for lytic enzyme genetically coded for by a bacteriophage specific for *Bacillus anthracis* and fragments of that enzyme, correspondingly provided are the complementary DNA strands of the cDNA molecule and DNA molecules which hybridize under stringent conditions to the lytic enzyme cDNA molecule or its complementary strand. Such hybridizing molecules include DNA molecules differing only by minor sequence changes, including nucleotide substitutions, deletions and additions. Also contemplated by this disclosure are isolated oligonucleotides comprising at least a segment of the cDNA molecule or its complementary strand, such as oligonucleotides which may be employed as effective DNA hybridization probes or primers useful in the polymerase chain reaction. Hybridizing DNA molecules and variants on the lytic enzyme cDNA may readily be created by standard molecular biology techniques.

A large variety of isolated cDNA sequences that encode phage associated lysing enzymes and partial sequences that hybridize with such gene sequences are useful for recombinant production of the lysing enzyme. Representative nucleic acid sequences in this context are polynucleotide sequences coding for the polypeptides of SEQ ID NO:1, SEQ ID NO:2, SEQ ID NO:3, SEQ ID NO:4, SEQ ID NO:5 or SEQ ID NO:6, sequence and sequences that hybridize, under stringent conditions, with complementary sequences of the DNA encoding the FIG. 1 polypeptide sequences. Still further variants of these sequences and sequences of nucleic acids that hybridize with those shown in the Figures also are contemplated for use in production of lysing enzymes according to the disclosure, including natural variants that may be obtained.

The detection of specific DNA mutations may be achieved by methods such as hybridization using specific oligonucleotides (Wallace et al. (1986). Cold Spring Harbor Symp. Quant. Biol. 51:257-261), direct DNA sequencing (Church and Gilbert (1988). Proc. Natl. Acad. Sci. USA 81:1991-1995), the use of restriction enzymes (Flavell et al. (1978). Cell 15:25), discrimination on the basis of electrophoretic mobility in gels with denaturing reagent (Myers and Maniatis (1986). Cold Spring Harbor Symp. Quant. Biol. 51:275-284), RNase protection (Myers et al. (1985). Science 230:1242), chemical cleavage (Cotton et al. (1985). Proc. Natl. Acad. Sci. USA 85:4397-4401) (incorporated herein by reference), and the ligase-mediated detection procedure (Landegren et al., 1988).

Many of the contemplated variant DNA molecules include those created by standard DNA mutagenesis techniques, such as M13 primer mutagenesis. Details of these techniques are provided in Sambrook et al. (1989) In Molecular Cloning: A Laboratory Manual, Cold Spring Harbor, N.Y. (incorporated herein by reference). By the use of such techniques, variants may be created which differ in minor ways from those disclosed. DNA molecules and nucleotide sequences which are derivatives of those specifically disclosed herein and which differ from those disclosed by the deletion, addition or substitution of nucleotides while still encoding a protein which possesses the functional characteristic of the BSMR protein are contemplated by the disclosure. Also included are one small DNA molecules which are derived from the disclosed DNA molecules. Such small DNA molecules include oligonucleotides suitable for use as hybridization probes or polymerase chain reaction (PCR) primers. As such, these small DNA molecules will comprise at least a segment of a lytic enzyme genetically coded for by a bacteriophage specific for *Bacillus anthracis* and, for the purposes of PCR, will comprise at least a 10-15 nucleotide sequence and, more preferably, a 15-30 nucleotide sequence of the gene. DNA molecules and nucleotide sequences which are derived from the disclosed DNA molecules as described above may also be defined as DNA sequences which hybridize under stringent conditions to the DNA sequences disclosed, or fragments thereof.

Oligonucleotides specific to normal or mutant sequences are chemically synthesized using commercially available machines, labeled radioactively with isotopes (such as $^{32}P$) or non-radioactively (with tags such as biotin (Ward and Langer et al. Proc. Natl. Acad. Sci. USA 78:6633-6657 1981) (incorporated herein by reference), and hybridized to individual DNA samples immobilized on membranes or other solid supports by dot-blot or transfer from gels after electrophoresis. The presence or absence of these specific sequences are visualized by methods such as autoradiography or fluorometric or colorimetric reactions (Gebeyehu et al. Nucleic Acids Res. 15:4513-4534 1987) (incorporated herein by reference).

Sequence differences between normal and mutant forms of the gene may also be revealed by the direct DNA sequencing method of Church and Gilbert (1988) (incorporated herein by reference). Cloned DNA segments may be used as probes to detect specific DNA segments. The sensitivity of this method is greatly enhanced when combined with PCR (Stoflet et al. Science 239:491-494, 1988) (incorporated herein by reference). In this approach, a sequencing primer which lies within the amplified sequence is used with double-stranded PCR product or single-stranded template generated by a modified PCR. The sequence determination is performed by conventional procedures with radiolabeled nucleotides or by automatic sequencing procedures with fluorescent tags. Such sequences are useful for production of lytic enzymes according to embodiments of the disclosure.

Hybridization conditions corresponding to particular degrees of stringency vary depending upon the nature of the hybridization method of choice and the composition and length of the hybridizing DNA used. Generally, the temperature of hybridization and the ionic strength (especially the sodium ion concentration) of the hybridization buffer will determine the stringency of hybridization. Calculations regarding hybridization conditions required for attaining particular degrees of stringency are discussed by Sambrook et al. (1989), In Molecular Cloning: A Laboratory Manual, Cold Spring Harbor, N.Y., chapters 9 and 11, (herein incorporated by reference).

An example of such calculation is as follows. A hybridization experiment may be performed by hybridization of a DNA molecule (for example, a natural variation of the lytic enzyme genetically coded for by a bacteriophage specific for *Bacillus anthracis*) to a target DNA molecule. A target DNA may be, for example, the corresponding cDNA which has been electrophoresed in an agarose gel and transferred to a nitrocellulose membrane by Southern blotting (Southern (1975). J. Mol. Biol. 98:503), a technique well known in the art and described in Sambrook et al. (1989) In Molecular Cloning: A Laboratory Manual, Cold Spring Harbor, N.Y. (incorporated herein by reference). Hybridization with a target probe labeled with isotopic P (32) labeled-dCTP is carried out in a solution of high ionic strength such as 6 times SSC at a temperature that is 20-25 degrees Celsius below the melting temperature, Tm, (described infra). For such Southern hybridization experiments where the target DNA molecule on the Southern blot contains 10 ng of DNA or more, hybridization is carried out for 6-8 hours using 1-2 ng/ml radiolabeled probe (of specific activity equal to $10^9$ CPM/mug or greater). Following hybridization, the nitrocellulose filter is washed to remove background hybridization. The washing conditions are as stringent as possible to remove background hybridization while retaining a specific hybridization signal. The term "Tm" represents the temperature above which, under the prevailing ionic conditions, the radiolabeled probe molecule will not hybridize to its target DNA molecule.

The Tm of such a hybrid molecule may be estimated from the following equation: Tm=81.5 degrees C. −16.6 log 10 of sodium ion concentration)+0.41(% G+C)−0.63(% formamide)−(600/I) where I=the length of the hybrid in base pairs. This equation is valid for concentrations of sodium ion in the range of 0.01M to 0.4M, and it is less accurate for calculations of Tm in solutions of higher sodium ion concentration (Bolton and McCarthy (1962). Proc. Natl. Acad. Sci. USA 48:1390) (incorporated herein by reference). The equation also is valid for DNA having G+C contents within 30% to 75%, and also applies to hybrids greater than 100 nucleotides in length. The behavior of oligonucleotide probes is described in detail in Ch. 11 of Sambrook et al. (1989), In Molecular Cloning: A Laboratory Manual, Cold Spring Harbor, N.Y. (incorporated herein by reference). The preferred exemplified conditions described here are particularly contemplated for use in selecting variations of the lytic gene.

Thus, by way of example, of a 150 base pair DNA probe derived from the first 150 base pairs of the open reading frame of a cDNA having a % GC=45%, a calculation of hybridization conditions required to give particular stringencies may be made as follows:

Assuming that the filter will be washed in 0.3×SSC solution following hybridization, sodium ion=0.045M; %

GC=45%; Formamide concentration=0 I=150 base pairs (see equation in Sambrook et al.) and so Tm=74.4 degrees C. The Tm of double-stranded DNA decreases by 1-1.5 degrees C. with every 1% decrease in homology (Bonner et al. (1973). J. Mol. Biol. 81:123). Therefore, for this given example, washing the filter in 0.3 times SSC at 59.4-64.4 degrees C. will produce a stringency of hybridization equivalent to 90%; DNA molecules with more than 10% sequence variation relative to the target BSMR cDNA will not hybridize. Alternatively, washing the hybridized filter in 0.3 times SSC at a temperature of 65.4-68.4 degrees C. will yield a hybridization stringency of 94%; DNA molecules with more than 6% sequence variation relative to the target BSMR cDNA molecule will not hybridize. The above example is given entirely by way of theoretical illustration. One skilled in the art will appreciate that other hybridization techniques may be utilized and that variations in experimental conditions will necessitate alternative calculations for stringency.

In preferred embodiments of the present disclosure, stringent conditions may be defined as those under which DNA molecules with more than 25% sequence variation (also termed "mismatch") will not hybridize. In a more preferred embodiment, stringent conditions are those under which DNA molecules with more than 15% mismatch will not hybridize, and more preferably still, stringent conditions are those under which DNA sequences with more than 10% mismatch will not hybridize. Preferably, stringent conditions are those under which DNA sequences with more than 6% mismatch will not hybridize.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0-1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1.times.SSC at about 37-50° C. The skilled artisan will recognize how to adjust the temperature, ionic strength, etc. as necessary to accommodate factors such as probe length and the like.

Vectors/Host Cells Expressing Polynucleotides for Lysins

Embodiments of the disclosure also include vectors that comprise a polynucleotide or polynucleotides encoding one of the lysin polypeptide sequences described herein, or variants or fragments thereof, including just the binding region, or as much as the entire lysin protein or ligation/conjugate of binding region with other protein. Other embodiments concern host cells that are genetically engineered with vectors of the disclosure and the production of polypeptides of the disclosure by recombinant techniques. Cell-free translation systems can also be employed to produce such proteins using RNAs derived from the DNA constructs of the disclosure.

For recombinant production, host cells can be genetically engineered to incorporate expression systems or portions thereof or polynucleotides of the disclosure. Introduction of a polynucleotide into the host cell can be effected by methods described in many standard laboratory manuals, such as Davis et al., BASIC METHODS IN MOLECULAR BIOLOGY, (1986) and Sambrook et al., MOLECULAR CLONING: A LABORATORY MANUAL, 2nd Ed., Cold Spring Harbor Laboratory Press, Cold Spring Harbor, N.Y. (1989), such as, calcium phosphate transfection, DEAE-dextran mediated transfection, transvection, microinjection, cationic lipid-mediated transfection, electroporation, transduction, scrape loading, ballistic introduction and infection.

Representative examples of appropriate hosts include bacterial cells, such as Streptococci, Staphylococci, Enterococci *E. coli, Streptomyces* and *Bacillus subtilis* cells; fungal cells, such as yeast cells and *Aspergillus* cells; insect cells such as *Drosophila* S2 and *Spodoptera* Sf9 cells; animal cells such as CHO, COS, HeLa, C127, 3T3, BHK, 293 and Bowes melanoma cells; and plant cells.

A great variety of expression systems can be used to produce the polypeptides of the disclosure. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression system constructs may contain control regions that regulate as well as engender expression. Generally, any system or vector suitable to maintain, propagate or express polynucleotides and/or to express a polypeptide in a host may be used for expression in this regard. The appropriate DNA sequence may be inserted into the expression system by any of a variety of well-known and routine techniques, such as, for example, those set forth in Sambrook et al., MOLECULAR CLONING, A LABORATORY MANUAL, (supra).

For secretion of the translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

Polypeptides of the disclosure can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography. High performance liquid chromatography is also employed for purification. Well known techniques for refolding protein may be employed to regenerate active conformation when the polypeptide is denatured during isolation and or purification.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

Diagnostic Assays

Detection assays advantageously utilize a heterogeneous format wherein a binding reaction between a conjugated binding agent and an analyte occurs followed by a wash step to remove unbound conjugated binding agent. For example, gold sol particles may be prepared with protein that comprises the binding region with the binding protein immobilized on the particle surfaces. As binding occurs between the protein and bacteria, the particles merge and form a colored product. Analogously, the binding protein may be complexed, preferably covalently with an enzyme such as beta galactosidase, peroxidase, or horseradish peroxidase. After wash, the remaining bound enzyme can be detected by adding a substrate such as a fluorogenic or chemilumigenic substrate. The binding protein may be complexed with any other reagent that can make a signal such as a rare earth fluor and detected by time resolved fluorescence, a radioactive material and detected by radioactivity measurement, or a regular fluorescent tag, and detected by fluorescence.

The conjugation of the binding region with a detectable tag may be carried out by synthetic chemistry or a biological process. For example, a DNA sequence coding for the binding region or of the entire lysine protein can be linked to genetic information that encodes a detectable marker such as green fluorescent protein (GFP) or an enzyme such as alkaline phosphatase. This could be accomplished by separating the DNA for the binding domain by removing the N-terminal catalytic domain and replacing it in frame with indicator molecules such as green flouorescent protein (GFP) and purifying the expressed fusion molecule for the identification of *Bacillus anthracis*. Since the binding domain has a similar binding affinity of an immunoglobulin G molecule, the marked binding domain will effectively identify *Bacillus anthracis* with little false positive activity. One also could fuse the GFP molecule or an enzyme at the 5' end of the whole lysin enzyme if necessary, by doing so the enzymatic domain will be at least partly inactivated, still allowing the binding domain to function to bind to its substrate in the *Bacillus* cell wall.

The isolated binding domain separated from the catalytic domain may be expressed, purified and labeled using a number of fluorescent molecules such as fluorescein isothiocyanate, rhodamine isothiocyanate and others known by skilled artisans. The binding domain may be modified with biotin to allow formation of a biotin-avidin complex after the binding region adheres to the *Bacillus anthracis* for identification.

Other catalytic domains may be added to the binding region. As exemplified by Diaz et al. Proc. Natl. Acad. Sci. U.S.A., 87:8125 (1990) for another system, the catalytic domain may be replaced with catalytic domains from other phage lytic enzymes to cleave other bonds in the peptidoglycan cell wall of *Bacillus anthracis*. For example, the portion of the 5' end of the gamma lysin gene that codes for the N-terminal catalytic domain (an amidase) may be removed and replaced with the catalytic domain from phage lytic enzymes of other *Bacillus* phage and even from phage of other gram-positive and gram-negative bacteria. These catalytic domains may be other amidases (which may have higher activity or special features), muramidases, glucaminidases, or endopeptidases, all of which, when genetically fused to the binding domain of the gamma lysin will cleave their respective bonds in the peptidoglycan of the *Bacillus anthracis*. In a related embodiment two or three (or more) tandem catalytic domains of different specificities may be fused (i.e., muramidases-glucaminidases-amidase) to a single gamma lysin binding domain to cleave these bonds in the *Bacillus anthracis* cell wall peptidoglycan producing a highly active cleaving enzyme. Navarre (Identification of a D alanyl glycine endopeptidase activity. J Biol Chem. 1999 May 28; 274: 15847 56.) has shown that triple enzymatic domains may exist in bacteriophage lytic enzymes.

Various conventional linkers can be used, e.g., diisocyanates, diisothiocyanates, carbodiimides, bis-hydroxysuccinimide esters, maleimide-hydroxysuccinimide esters, glutaraldehyde and the like, preferably a selective sequential linker such as the anhydride-isothiocyante linker disclosed in U.S. Pat. No. 4,680,338.

Therapeutic Compositions

In some embodiments, the present disclosure pertains to lytic enzymes as a prophylactic treatment for preventing those who have possibly been exposed to *Bacillus anthracis*, or as a therapeutic treatment for those who have already become ill from the infection. The phage associated lytic enzymes described herein are specific for *Bacillus anthracis* and preferably effectively and efficiently break down the cell wall of the *Bacillus anthracis*.

The lytic enzyme polypeptides described herein may also be employed as a therapeutic agent. The lytic enzyme polypeptides of the present invention can be formulated according to known methods to prepare pharmaceutically useful compositions, whereby the lytic enzyme product hereof is combined in admixture with a pharmaceutically acceptable carrier vehicle. Compositions which may be used for the prophylactic and therapeutic treatment of a *Bacillus anthracis* infection also includes the shuffled and/or chimeric enzyme and a means of application (such as a carrier system or an oral delivery mode) to the mucosal lining of the oral and nasal cavity, such that the enzyme is put in the carrier system or oral delivery mode to reach the mucosa lining.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

Prior to, or at the time the modified lytic enzyme is put in the carrier system or oral delivery mode, it is the enzyme may be in a stabilizing buffer environment for maintaining a suitable pH range, such as between about 3.0 and about 12.0, between about 4.0 and about 11.0, between about 4.0 and about 10.0, between about 4.0 and about 9.0, between about 4.0 and about 8.0, between about 4.0 and about 7.0, between about 4.0 and about 6.0, or more preferably between about 4.0 and about 10.0, most preferably between about 4.0 and about 8.0, including 0.1 pH units therebetween.

Therapeutic formulations are prepared for storage by mixing the active ingredient having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™ or PEG.

Any of the carriers for the lytic enzyme may be manufactured by conventional means. However, if alcohol is used in the carrier, the enzyme should be in a micelle, liposome, or a "reverse" liposome, to prevent denaturing of the enzyme. Similarly, when the lytic enzyme is being placed in the carrier, and the carrier is, or has been heated, such placement should be made after the carrier has cooled somewhat, to avoid heat denaturation of the enzyme. In a preferred embodiment of the invention, the carrier is sterile. One or more lytic enzymes may be added to these substances in a liquid form or in a lyophilized state, whereupon it will be solubilized when it meets a liquid body.

Stabilizing Buffers

A stabilizing buffer should allow for the optimum activity of the lysin enzyme. The buffer may contain a reducing reagent, such as dithiothreitol. The stabilizing buffer may also be or include a metal chelating reagent, such as ethylenediaminetetracetic acid disodium salt, or it may also contain a phosphate or citrate phosphate buffer, or any other buffer. The DNA coding of these phages and other phages may be altered to allow a recombinant enzyme to attack one cell wall at more than two locations, to allow the recombinant enzyme to cleave the cell wall of more than one species of bacteria, to allow the recombinant enzyme to attack other bacteria, or any combinations thereof. The type and number of alterations to a recombinant bacteriophage produced enzyme are incalculable. Any number of chimeric and shuffled lytic enzymes, alone or along with holin proteins, may be assembled to treat the exposure to *Bacillus anthracis.*

Mucoadhesives

In some embodiments, a therapeutic composition comprises a mucoadhesive and a lytic enzyme, or chimeric and/or shuffled lytic enzymes, or their peptide fragments when the composition is directed to the mucosal lining to kill colonizing disease bacteria. The mucosal lining, as disclosed and described herein, includes, for example, the upper and lower respiratory tract, eye, buccal cavity, nose, rectum, vagina, periodontal pocket, intestines and colon. Due to natural eliminating or cleansing mechanisms of mucosal tissues, conventional dosage forms are not retained at the application site for any significant length of time.

For these and other reasons it is advantageous to have materials which exhibit adhesion to mucosal tissues, to be administered with one or more phage enzymes and other complementary agents over a period of time. Materials having controlled release capability are particularly desirable, and the use of sustained release mucoadhesives has received a significant degree of attention.

J. R. Robinson (U.S. Pat. No. 4,615,697, incorporated herein by reference) provides a review of the various controlled release polymeric compositions used in mucosal drug delivery. The patent describes a controlled release treatment composition which includes a bioadhesive and an effective amount of a treating agent. The bioadhesive is a water swellable, but water insoluble fibrous, crosslinked, carboxy functional polymer containing (a) a plurality of repeating units of which at least about 80 percent contain at least one carboxyl functionality, and (b) about 0.05 to about 1.5 percent crosslinking agent substantially free from polyalkenyl polyether. While the polymers of Robinson are water swellable but insoluble, they are crosslinked, not thermoplastic, and are not as easy to formulate with active agents, and into the various dosage forms, as the copolymer systems of the present application. Micelles and multi lamellar micelles may also be used to control the release of enzyme.

Other approaches involving mucoadhesives which are the combination of hydrophilic and hydrophobic materials, are known. Orahesive® from E. R. Squibb & Co is an adhesive which is a combination of pectin, gelatin, and sodium carboxymethyl cellulose in a tacky hydrocarbon polymer, for adhering to the oral mucosa. However, such physical mixtures of hydrophilic and hydrophobic components eventually fall apart. In contrast, the hydrophilic and hydrophobic domains in the present disclosure produce an insoluble copolymer.

U.S. Pat. No. 4,948,580, also incorporated by reference, describes a bioadhesive oral drug delivery system. The composition includes a freeze dried polymer mixture formed of the copolymer poly(methyl vinyl ether/maleic anhydride) and gelatin, dispersed in an ointment base, such as mineral oil containing dispersed polyethylene. U.S. Pat. No. 5,413,792 (incorporated herein by reference) discloses paste like preparations comprising (A) a paste like base comprising a polyorganosiloxane and a water soluble polymeric material which are preferably present in a ratio by weight from 3:6 to 6:3, and (B) an active ingredient. U.S. Pat. No. 5,554,380 claims a solid or semisolid bioadherent orally ingestible drug delivery system containing a water in oil system having at least two phases. One phase comprises from about 25% to about 75% by volume of an internal hydrophilic phase and the other phase comprises from about 23% to about 75% by volume of an external hydrophobic phase, wherein the external hydrophobic phase is comprised of three components: (a) an emulsifier, (b) a glyceride ester, and (c) a wax material.

U.S. Pat. No. 5,942,243 describes some representative release materials useful for administering antibacterial agents according to embodiments of the disclosure.

An embodiment of a features therapeutic compositions containing polymeric mucoadhesives consisting essentially of a graft copolymer comprising a hydrophilic main chain and hydrophobic graft chains for controlled release of biologically active agents. The graft copolymer is a reaction product of (1) a polystyrene macromonomer having an ethylenically unsaturated functional group, and (2) at least one hydrophilic acidic monomer having an ethylenically unsaturated functional group. The graft chains consist essentially of polystyrene, and the main polymer chain of hydrophilic monomeric moieties, some of which have acidic functionality. The weight percent of the polystyrene macromonomer in the graft copolymer is between about 1 and about 20% and the weight percent of the total hydrophilic monomer in the graft copolymer is between 80 and 99%, and wherein at least 10% of said total hydrophilic monomer is acidic, said graft copolymer when fully hydrated having an equilibrium water content of at least 90%.

Compositions containing the copolymers gradually hydrate by sorption of tissue fluids at the application site to yield a very soft jelly like mass exhibiting adhesion to the mucosal surface. During the period of time the composition is adhering to the mucosal surface, it provides sustained release of the pharmacologically active agent, which is absorbed by the mucosal tissue.

Mucoadhesivity of the compositions of these embodiments are, to a large extent, produced by the hydrophilic acidic monomers of the chain in the polystyrene graft copolymer. The acidic monomers include, but are not limited to, acrylic and methacrylic acids, 2 acrylamido 2 methyl propane sulfonic acid, 2 sulfoethyl methacrylate, and vinyl phosphonic acid. Other copolymerizable monomers include, but are not limited to N,N dimethylacrylamide, glyceryl methacrylate, polyethylene glycol monomethacrylate, etc.

The compositions of the disclosure may optionally contain other polymeric materials, such as poly(acrylic acid), poly, (vinyl pyrrolidone), and sodium carboxymethyl cellulose plasticizers, and other pharmaceutically acceptable excipients in amounts that do not cause a deleterious effect upon mucoadhesivity of the composition. The dosage forms of the compositions of this disclosure can be prepared by conventional methods.

Pharmaceuticals

The present disclosure also provides compositions comprising one or more pharmaceutical agents and one or more lysins. Further provided are methods of treatment combining administration of one or more pharmaceutical agents and one or more lysins administered separately or in combination.

Pharmaceuticals for use in all embodiments of this disclosure include antimicrobial agents, anti-inflammatory agents, antiviral agents, local anesthetic agents, corticosteroids, destructive therapy agents, antifungals, and antiandrogens. Active pharmaceuticals that may be used in topical formulations include antimicrobial agents, especially those having anti-inflammatory properties such as dapsone, erythromycin, minocycline, tetracycline, clindamycin, and other antimicrobials. The preferred weight percentages for the antimicrobials are 0.5% to 10%.

Local anesthetics include tetracaine, tetracaine hydrochloride, lidocaine, lidocaine hydrochloride, dyclonine, dyclonine hydrochloride, dimethisoquin hydrochloride, dibucaine, dibucaine hydrochloride, butambenpicrate, and pramoxine hydrochloride. A preferred concentration for local anesthetics is about 0.025% to 5% by weight of the total composition. Anesthetics such as benzocaine may also be used at a preferred concentration of about 2% to 25% by weight.

Corticosteroids that may be used include betamethasone dipropionate, fluocinolone actinide, betamethasone valerate, triamcinolone actinide, clobetasol propionate, desoximetasone, diflorasone diacetate, amcinonide, flurandrenolide, hydrocortisone valerate, hydrocortisone butyrate, and desonide are recommended at concentrations of about 0.01% to 1.0% by weight. Preferred concentrations for corticosteroids such as hydrocortisone or methylprednisolone acetate are from about 0.2% to about 5.0% by weight.

Destructive therapy agents such as salicylic acid or lactic acid may also be used. A concentration of about 2% to about 40% by weight is preferred. Cantharidin is preferably utilized in a concentration of about 5% to about 30% by weight. Typical antifungals that may be used in topical compositions and their preferred weight concentrations include: oxiconazole nitrate (0.1% to 5.0%), ciclopirox olamine (0.1% to 5.0%), ketoconazole (0.1% to 5.0%), miconazole nitrate (0.1% to 5.0%), and butoconazole nitrate (0.1% to 5.0%). Other topical agents may be included to address a variety of topical co-infections that may occur as will be appreciated by skilled artisans.

Typically, treatments using a combination of drugs include antibiotics in combination with local anesthetics such as polymycin B sulfate and neomycin sulfate in combination with tetracaine for topical antibiotic gels to provide prophylaxis against infection and relief of pain. Another example is the use of minoxidil in combination with a corticosteroid such as betamethasone diproprionate for the treatment of alopecia ereata. The combination of an anti-inflammatory such as cortisone with an antifungal such as ketoconazole for the treatment of tinea infections is also an example.

In a preferred embodiment, the composition comprises dapsone and ethoxydiglycol, which allows for an optimized ratio of micro particulate drug to dissolved drug. This ratio determines the amount of drug delivered, compared to the amount of drug retained in or above the stratum corneum to function in the supracorneum domain. The system of dapsone and ethoxydiglycol may include purified water combined with "CARBOPOL®" gelling polymer, methylparaben, propylparaben, titanium dioxide, BHA, and a caustic material to neutralize the "CARBOPOL®"

In order to accelerate treatment of the infection, the therapeutic agent may further include at least one complementary agent which can also potentiate the bactericidal activity of the lytic enzyme. The complementary agent can be erythromycin, clarithromycin, azithromycin, roxithromycin, other members of the macrolide family, penicillins, cephalosporins, and any combinations thereof in amounts which are effective to synergistically enhance the therapeutic effect of the lytic enzyme. Virtually any other antibiotic may be used with the modified lytic enzyme. Similarly, other lytic enzymes may be included in the carrier to treat other bacterial infections. Holin proteins may be included in the therapeutic treatment.

In some embodiments, a mild surfactant in an amount effective to potentiate the therapeutic effect of the modified lytic enzyme may be used in or in combination with a therapeutic composition. Suitable mild surfactants include, inter alia, esters of polyoxyethylene sorbitan and fatty acids (Tween series), octylphenoxy polyethoxy ethanol (Triton X series), n Octyl beta.D glucopyranoside, n Octyl betaD thioglucopyranoside, n Decal beta D glucopyranoside, n Dodecyl betaD glucopyranoside, and biologically occurring surfactants, e.g., fatty acids, glycerides, monoglycerides, deoxycholate and esters of deoxycholate. While this treatment, as with all of the other treatments, may be used in any mammalian species or any animal species that can contract or transmit anthrax, the most common use of this product may be for a human during biological warfare or terrorism.

Administration of Compositions Comprising Lysins

Therapeutic compositions comprising one or more lytic enzymes, such as PlyPH, or variants or fragments thereof, can be administered to a subject by any suitable means. Means of application of the lytic enzyme(s) (modified or unmodified) include, but are not limited to direct, indirect, carrier and special means or any combination of means. Direct application of the lytic enzyme may be by nasal sprays, nasal drops, nasal ointments, nasal washes, nasal injections, nasal packings, bronchial sprays and inhalers, or indirectly through use of throat lozenges, mouthwashes or gargles, or through the use of ointments applied to the nasal flares, or any combination of these and similar methods of application. The forms in which the lytic enzyme may be administered include but are not limited to lozenges, troches, candies, injectants, chewing gums, tablets, powders, sprays, liquids, ointments, and aerosols. It is most probable that exposure to the *Bacillus anthracis* will be through the nose. It is best to be treated for exposure to the bacteria as soon as possible.

When the lytic enzyme(s) is introduced directly by use of nasal sprays, nasal drops, nasal ointments, nasal washes, nasal injections, nasal packing, bronchial sprays, oral sprays, and inhalers, the enzyme is preferably in a liquid or gel environment, with the liquid acting as the carrier. A dry anhydrous version of the modified enzyme may be administered by the inhaler and bronchial spray, although a liquid form of delivery is preferred.

The lozenge, tablet, or gum into which the enzyme is added may contain sugar, corn syrup, a variety of dyes, non sugar sweeteners, flavorings, any binders, or combinations thereof. Similarly, any gum based products may contain acacia, carnauba wax, citric acid, corn starch, food colorings, flavorings, non sugar sweeteners, gelatin, glucose, glycerin, gum base, shellac, sodium saccharin, sugar, water, white wax, cellulose, other binders, and combinations thereof.

Lozenges may further contain sucrose, corn starch, acacia, gum tragacanth, anethole, linseed, oleoresin, mineral oil, and cellulose, other binders, and combinations thereof. In another embodiment of the disclosure, sugar substitutes are used in place of dextrose, sucrose, or other sugars.

As noted above, the enzyme may also be placed in a nasal spray, wherein the spray is the carrier. The nasal spray can be a long acting or timed release spray, and can be manufactured by means well known in the art. An inhalant may also be used, so that the enzyme may reach further down into the bronchial tract, including into the lungs.

Any of the carriers for the lytic enzyme may be manufactured by conventional means. However, it is preferred that any mouthwash or similar type products not contain alcohol to prevent denaturing of the enzyme, although enzymes in liposomes and in other protective modes and forms may be used in alcohol. Similarly, when the enzyme(s) is (are) being placed in a cough drop, gum, candy or lozenge during the manufacturing process, such placement should be made prior to the hardening of the lozenge or candy but after the cough drop or candy has cooled somewhat, to avoid heat denaturation of the enzyme. The enzyme can also be sprayed over the surface of the cough drop gum, candy, or lozenge, in high enough dosages to be effective.

The enzyme may be added to these substances in a liquid form or in a lyophilized state, whereupon it will be solubilized when it meets body fluids such as saliva. The enzyme may also be in a micelle or liposome.

Dosage of Lysins

The effective dosage rates or amounts of the enzyme(s) to treat the infection will depend in part on whether the enzyme(s) will be used therapeutically or prophylactically, the duration of exposure of the recipient to the infectious bacteria, the size and weight of the individual, etc. The duration for use of the composition containing the enzyme also depends on whether the use is for prophylactic purposes, wherein the use may be hourly, daily or weekly, for a short time period, or whether the use will be for therapeutic purposes wherein a more intensive regimen of the use of the composition may be needed, such that usage may last for hours, days or weeks, and/or on a daily basis, or at timed intervals during the day. Any dosage form employed should provide for a minimum number of units for a minimum amount of time. The concentration of the active units of enzyme that may provide for an effective amount or dosage of enzyme may be in the range of about (e.g. exactly) 100 units/ml to about 500,000 units/ml of fluid in the wet or damp environment of the nasal and oral passages, and topically as well and possibly in the range of about 100 units/ml to about 50,000 units/ml. Representative values thus include about 200 units/ml, 300 units/ml, 500 units/ml, 1,000 units/ml, 2,500 units/ml, 5,000 units/ml, 10,000 units/ml, 20,000 units/ml, 30,000 units/ml, and 40,000 units/ml. More specifically, time exposure to the active enzyme units may influence the desired concentration of active enzyme units per ml. It should be noted that carriers that are classified as "long" or "slow" release carriers (such as, for example, certain nasal sprays or lozenges) could possess or provide a lower concentration of active (enzyme) units per ml, but over a longer period of time, whereas a "short" or "fast" release carrier (such as, for example, a gargle) could possess or provide a high concentration of active (enzyme) units per ml, but over a shorter period of time. The amount of active units per ml and the duration of time of exposure depends on the nature of infection, whether treatment is to be prophylactic or therapeutic, and other variables. Thus, the number of dosages will be dependent upon the circumstances and can range from 1-4 times per day or more, with durations from one day to multiple weeks. Infections can occur in the skin and thus such compositions may be formulated for topical application as well, using well known vehicles such as those described in U.S. Pat. Nos. 6,056,954 and 6,056,955.

Methods of Treatment

There are a number of advantages to using lytic enzymes to treat bacterial infections, particularly *Bacillus anthracis*. The modular design of lysins, with their distinct catalytic and binding domains, makes them ideal for domain swapping experiments in which bacterial specificities and catalytic activities can be improved or adapted for use against alternate pathogens. Since the catalytic and binding targets of lysins (peptidoglycan and associated carbohydrates, respectively) are largely essential for viability, lysin resistance will be rare. Consequently, the use of the phage lytic enzymes directed against *Bacillus anthracis* appears to be a viable means of treating an anthrax infection of an organism, or treating anthrax contamination of an object or a surface area.

"Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

"Mammal" for purposes of treatment refers to any animal classified as a mammal, including humans, domestic and farm animals, and zoo, sports, or pet animals, such as dogs, cats, cattle, horses, sheep, pigs, goats, rabbits, etc. Preferably, the mammal is human.

The formulations to be used for in vivo administration are preferably sterile. This is readily accomplished by filtration through sterile filtration membranes, prior to or following lyophilization and reconstitution. Therapeutic compositions herein generally are placed into a container having a sterile access port, for example, an intravenous solution bag or vial having a stopper pierceable by a hypodermic injection needle.

The route of administration is in accord with known methods, e.g. injection or infusion by intravenous, intraperitoneal, intracerebral, intramuscular, intraocular, intraarterial or intralesional routes, topical administration, or by sustained release systems. When treating an anthrax exposure or infection, the lytic enzyme may be administered preferably, either parenterally or through the oral or nasal cavity.

Dosages and desired drug concentrations of pharmaceutical compositions of the present invention may vary depending on the particular use envisioned. The determination of the appropriate dosage or route of administration is well within the skill of an ordinary physician. Animal-experiments provide reliable guidance for the determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42-96.

When in vivo administration of a lytic enzyme is employed, normal dosage amounts may vary from about 10 ng/kg to up to 100 mg/kg of mammal body weight or more per day, preferably about 1 μg/kg/day to 10 mg/kg/day, depending upon the route of administration. Guidance as to particular dosages and methods of delivery is also provided below, as well as in the literature. It is anticipated that different formulations will be effective for different treatment compounds and different disorders, that administration targeting one organ or tissue, for example, may necessitate delivery in a manner different from that to another organ or tissue.

Where sustained-release administration of a lytic enzyme is desired in a formulation with release characteristics suitable for the treatment of any disease or disorder requiring administration of the lytic enzyme, microencapsulation of the lytic enzyme is contemplated. Microencapsulation of recombinant proteins for sustained release has been successfully performed with human growth hormone (rhGH), interferon-(rhIFN-), interleukin-2, and MN rgp120. Johnson et al., Nat. Med., 2:795-799 (1996); Yasuda, Biomed. Ther., 27:1221-1223 (1993); Hora et al., Bio/Technology. 8:755-758 (1990); Cleland, "Design and Production of Single Immunization Vaccines Using Polylactide Polyglycolide Microsphere Systems." in Vaccine Design The Subunit and Adjuvant Approach, Powell and Newman, eds, (Plenum Press: New York, 1995), pp. 439462; WO 97/03692, WO 96/40072, WO 96/07399; and U.S. Pat. No. 5,654,010.

The sustained-release formulations of these proteins can use poly-lactic-coglycolic acid (PLGA) polymer due to its biocompatibility and wide range of biodegradable properties. The degradation products of, PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer," in: M. Chasin and R. Langer (Eds.), Biodegradable Polymers as Drul: Delivery Systems (Marcel Dekker: New York, 1990), pp. 1-41.

Cutaneous Anthrax

About 95% of naturally occurring anthrax cases are in the cutaneous form, the least harmful manifestation of the disease, with inhalational anthrax making up 5% of the cases and gastrointestinal anthrax accounting for 0 to 5% of cases. Cutaneous anthrax occurs when *B. anthracis* spores enters the body through a break in the skin. It begins with the development of a pruritic papule at the site of inoculation. A series of vesicles then form around the original papule, which eventually dries to form the characteristic black eschar associated with cutaneous anthrax. Major edema develops around the site. Once the infection is established, antibiotics do not prevent the progression of cutaneous anthrax to formation of the eschar. Surprisingly, pain is minimal in incidents of cutaneous anthrax. In many cases, the lesion resolves without antibiotics. However, about 20% of patients develop systemic infection originating from the cutaneous lesion, and in those cases, death results without treatment.

Compositions for treating topical infections comprise an effective amount of at least one lytic enzyme produced according to this disclosure and a carrier for delivering at least one lytic enzyme to the infected skin. The mode of application for the lytic enzyme includes a number of different types and combinations of carriers which include, but are not limited to an aqueous liquid, an alcohol base liquid, a water soluble gel, a lotion, an ointment, a nonaqueous liquid base, a mineral oil base, a blend of mineral oil and petrolatum, lanolin, liposomes, protein carriers such as serum albumin or gelatin, powdered cellulose carmel, and combinations thereof. A mode of delivery of the carrier containing the therapeutic agent includes, but is not limited to a smear, spray, a time-release patch, a liquid absorbed wipe, and combinations thereof. The lytic enzyme may be applied to a bandage either directly or in one of the other carriers. The bandages may be sold damp or dry, wherein the enzyme is in a lyophilized form on the bandage. This method of application is most effective for the treatment of infected skin.

The carriers of topical compositions may comprise semi-solid and gel-like vehicles that include a polymer thickener, water, preservatives, active surfactants or emulsifiers, antioxidants, sun screens, and a solvent or mixed solvent system. U.S. Pat. No. 5,863,560 (Osborne) discusses a number of different carrier combinations which can aid in the exposure of the skin to a medicament.

Polymer thickeners that may be used include those known to one skilled in the art, such as hydrophilic and hydroalcoholic gelling agents frequently used in the cosmetic and pharmaceutical industries. Preferably, the hydrophilic or hydroalcoholic gelling agent comprises "CARBOPOL®" (B.F. Goodrich, Cleveland, Ohio), "HYPAN®" (Kingston Technologies, Dayton, N.J.), "NATROSOL®" (Aqualon, Wilmington, Del.), "KLUCEL®" (Aqualon, Wilmington, Del.), or "STABILEZE®" (ISP Technologies, Wayne, N.J.). Preferably, the gelling agent comprises between about 0.2% to about 4% by weight of the composition. More particularly, the preferred compositional weight percent range for "CARBOPOLO®" is between about 0.5% to about 2%, while the preferred weight percent range for "NATROSOL®" and "KLUCEL®" is between about 0.5% to about 4%. The preferred compositional weight percent range for both "HYPAN®" and "STABILEZE®" is between about 0.5% to about 4%.

"CARBOPOL®" is one of numerous cross-linked acrylic acid polymers that are given the general adopted name carbomer. These polymers dissolve in water and form a clear or slightly hazy gel upon neutralization with a caustic material such as sodium hydroxide, potassium hydroxide, triethanolamine, or other amine bases. "KLUCEL®" is a cellulose polymer that is dispersed in water and forms a uniform gel upon complete hydration. Other preferred gelling polymers include hydroxyethylcellulose, cellulose gum, MVE/MA decadiene crosspolymer, PVM/MA copolymer, or a combination thereof.

Preservatives may also be used in this invention and preferably comprise about 0.05% to 0.5% by weight of the total composition. The use of preservatives assures that if the product is microbially contaminated, the formulation will prevent or diminish microorganism growth. Some preservatives useful in this invention include methylparaben, propylparaben, butylparaben, chloroxylenol, sodium benzoate, DMDM Hydantoin, 3-Iodo-2-Propylbutyl carbamate, potassium sorbate, chlorhexidine digluconate, or a combination thereof.

Titanium dioxide may be used as a sunscreen to serve as prophylaxis against photosensitization. Alternative sun screens include methyl cinnamate. Moreover, BHA may be used as an antioxidant, as well as to protect ethoxydiglycol and/or dapsone from discoloration due to oxidation. An alternate antioxidant is BHT.

In one embodiment, the invention comprises a dermatological composition having about 0.5% to 10% carbomer and about 0.5% to 10% of a pharmaceutical that exists in both a dissolved state and a micro particulate state. The dissolved pharmaceutical has the capacity to cross the stratum corneum, whereas the micro particulate pharmaceutical does not. Addition of an amine base, potassium, hydroxide solution, or sodium hydroxide solution completes the formation of the gel. More particularly, the pharmaceutical may include dapsone, an antimicrobial agent having anti-inflammatory properties. A preferred ratio of micro particulate to dissolved dapsone is five or less.

In another embodiment, the invention comprises about 1% carbomer, about 80-90% water, about 10% ethoxydiglycol, about 0.2% methylparaben, about 0.3% to 3.0% dapsone including both micro particulate dapsone and dissolved dapsone, and about 2% caustic material. More particularly, the carbomer may include "CARBOPOL® 980" and the caustic material may include sodium hydroxide solution.

Most *Bacillus anthracis* infections occur when the bacterium, normally in the form of a spore, is inhaled into the nose. There, the spore can be inhaled further into the body, and into the lung, where, through a series of steps, it can germinate and lead to a systemic infection and death. Consequently, it is important to treat the infection as soon as possible, preferably while it is still in the nasal or oral cavity. When treating the infection, the carrier should further comprise a germinant, preferably L-alanine, so that the lytic enzyme (and/or the chimeric and/or shuffled lytic enzymes) can be most effective.

The infectious dose to cause inhalational anthrax has been projected to be between 2,500 to 50,000 spores. *B. anthracis* spore particles smaller than 5 μm can be inhaled through the airway into the pulmonary alveoli where they are ingested by pulmonary macrophages. Within the macrophages, the germinating spores are transported to the mediastinal lymph nodes where bacterial multiplication overwhelms the node and enters the bloodstream. The illness is often described as being biphasic, with the first phase manifesting in nonspecific 'flu-like' symptoms. After the first phase, some patients reportedly experience a brief period of improvement prior to the rapid degeneration into the second deadly phase, characterized by fever, shortness of breath, cyanosis, and respiratory failure as the body goes into shock. Inhalational anthrax is associated with high mortality rates. Early treatment of patients with inhalational anthrax can be hampered by nonspecific symptoms.

A serious complication of systemic infection with *B. anthracis* is the development of hemorrhagic meningitis. It is often associated with bacteremia arising from inhalational anthrax, and considerably less often with other forms of anthrax. Up to 50% of patients with systemic anthrax disease develop hemorrhagic meningitis, with mortality close to 100%.

In one embodiment, if there is a bacterial infection of the upper respiratory tract, the infection can be prophylactically or therapeutically treated with a composition comprising an effective amount of at least one lytic enzyme produced by a bacteria being infected with a bacteriophage specific for that bacteria, and a carrier for delivering the lytic enzyme to a mouth, throat, or nasal passage. The lytic enzyme may be a lytic enzyme, a chimeric lytic enzyme, and/or shuffled lytic enzyme which may be used in conjunction with a holin protein or a combination thereof. The lytic enzyme may be in an environment having a pH which allows for activity of the lytic enzyme. For example, the pH range for the PlyPH enzyme is about 3-12, with a pH of about 4-8 being the most optimal. If an individual has been exposed to someone with the upper respiratory disorder, the lytic enzyme will reside in the mucosal lining and prevent any colonization of the infecting bacteria.

Parenteral Administration

Once the *Bacillus anthracis* gets past the nasal oral cavity, the likelihood of a systemic infection increases. Thus, it becomes necessary for the infection to be treated parenterally. The enzymes which can be used are, as above, lytic enzymes, chimeric lytic, enzymes, shuffled lytic enzymes, and combinations thereof. The enzymes can be administered intramuscularly, intravenously, subcutaneously, subdermally, or combinations thereof. Intravenous treatment is most likely the best treatment for a full blown anthrax infection.

In one embodiment, infections may be treated by injecting into the patient a therapeutic agent comprising the appropriate shuffled and/or chimeric lytic enzyme(s) and a carrier for the enzyme. The carrier may be comprised of distilled water, a saline solution, albumin, a serum, or any combinations thereof. More specifically, solutions for infusion or injection may be prepared in a conventional manner, e.g. with the addition of preservatives such as p-hydroxybenzoates or stabilizers such as alkali metal salts of ethylene diamine tetraacetic acid, which may then be transferred into fusion vessels, injection vials or ampules. Alternatively, the compound for injection may be lyophilized either with or without the other ingredients and be solubilized in a buffered solution or distilled water, as appropriate, at the time of use. Non aqueous vehicles such as fixed oils, liposomes, and ethyl oleate are also useful herein. Other phage associated lytic enzymes, along with a holin protein, may be included in the composition.

In cases where intramuscular injection is the chosen mode of administration, an isotonic formulation is preferably used. Generally, additives for isotonicity can include sodium chloride, dextrose, mannitol, sorbitol and lactose. In some cases, isotonic solutions such as phosphate buffered saline are used. Stabilizers include gelatin and albumin. In some embodiments, a vasoconstriction agent is added to the formulation.

The pharmaceutical preparations are provided sterile and pyrogen free. Generally, as noted above, intravenous injection may be most appropriate.

The carrier suitably contains minor amounts of additives such as substances that enhance isotonicity and chemical stability. Such materials are non toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; glycine; amino acids such as glutamic acid, aspartic acid, histidine, or arginine; monosaccharides, disaccharides, and other carbohydrates including cellulose or its derivatives, glucose, mannose, trehalose, or dextrins; chelating agents such as EDTA; sugar alcohols such as mannitol or sorbitol; counter ions such as sodium; non ionic surfactants such as polysorbates, poloxamers, or polyethylene glycol (PEG); and/or neutral salts, e.g., NaCl, KCl, $MgCl_2$, $CaCl_2$, etc.

Glycerin or glycerol (1,2,3 propanetriol) is commercially available for pharmaceutical use. It may be diluted in sterile water for injection, or sodium chloride injection, or other pharmaceutically acceptable aqueous injection fluid, and used in concentrations of 0.1 to 100% (v/v), preferably 1.0 to 50% more preferably about 20%.

DMSO, is an aprotic solvent with a remarkable ability to enhance penetration of many locally applied drugs. DMSO may be diluted in sterile water for injection, or sodium chloride injection, or other pharmaceutically acceptable aqueous injection fluid, and used in concentrations of 0.1 to 100% (v/v).

The vehicle may also include Ringer's solution, a buffered solution, and dextrose solution, particularly when an intravenous solution is prepared.

Prior to, or at the time the enzyme is put in the carrier system or oral delivery mode, it may be desirable for the enzymes be in a stabilizing buffer environment, maintaining a pH range between about 4.0 and about 8.0, more preferably between about 6.5 and about 7.5.

The stabilizing buffer should allow for the optimum activity of the enzyme. The buffer may be a reducing reagent, such as dithiothreitol. The stabilizing buffer may also be or include a metal chelating reagent, such as ethylenediaminetetracetic acid disodium salt, or it may also contain a phosphate or citrate phosphate buffer. The buffers found in the carrier can serve to stabilize the environment for the lytic enzymes.

The effective dosage rates or amounts of the enzyme to be administered parenterally, and the duration of treatment will depend in part on the seriousness of the infection, the weight of the patient, the duration of exposure of the recipient to the infectious bacteria, the seriousness of the infection, and a variety of a number of other variables. The composition may be applied anywhere from once to several times a day, and may be applied for a short or long term period. The usage may last for days or weeks. Any dosage form employed should provide for a minimum number of units for a minimum amount of time. The concentration of the active units of enzyme believed to provide for an effective amount or dosage of enzyme may be in the range of about 100 units/ml to about 10,000,000 units/ml of composition, in a range of about 1000 units/ml to about 10,000,000 units/ml, and from about 10,000 to 10,000,000 units/ml. The amount of active units per ml and the duration of time of exposure depends on the nature of infection, and the amount of contact the carrier allows the lytic enzyme to have. It is to be remembered that the enzyme works best when in a fluid environment. Hence, effectiveness of the enzyme is in part related to the amount of moisture trapped by the carrier. The concentration of the enzyme for the treatment is dependent upon the bacterial count in the blood and the blood volume.

In order to accelerate treatment of the infection, the therapeutic agent may further include at least one complementary agent which can also potentiate the bactericidal activity of the lytic enzyme. The complementary agent can be any antibiotic effective against *Bacillus anthracis*. Similarly, other lytic enzymes may be included to treat other bacterial infections.

Additionally, a number of methods can be used to assist in transporting the enzyme across the cell membrane. The enzyme can be transported in a liposome, with the enzyme be "inserted" in the liposomes by known techniques. Similarly, the enzyme may be in a reverse micelle. The enzyme can also be pegylated, attaching the polyethylene glycol to the non-active part of the enzyme. Alternatively, hydrophobic molecules can be used to used to transport the enzyme across the cell membrane. Finally, the glycosylation of the enzyme can be used to target specific internalization receptors on the membrane of the cell.

Gastrointestinal Anthrax

In other embodiments, compositions for the treatment of gastrointestinal anthrax are provided, and methods of using the same. Compositions preferably comprise a lysin and a carrier, as described herein. Gastrointestinal anthrax results from the ingestion of contaminated meat. Despite being the rarest form of anthrax, it is also the most deadly. Gastrointestinal anthrax resembles cutaneous anthrax in that it causes the formation of ulcers on the gastrointestinal epithelium that develop into eschars. There are two variants to this disease, an oropharyngeal form and an intestinal form, depending on the location of the primary site of infection. Both forms have an incubation period between 1 and 6 days. Other than fever, each form of gastrointestinal anthrax is characterized by a unique set of symptoms. Oropharyngeal anthrax is distinguished by ulceration of the oropharynx, in addition to severe sore throat, difficulty in swallowing, and significant swelling of the neck. Intestinal anthrax is characterized by nausea, vomiting, severe abdominal pain and bloody stool. Nonspecific symptoms such as fever, severe abdominal pain and vomiting make diagnosing gastrointestinal anthrax difficult, contributing to the high mortality rate associated with this manifestation of anthrax.

Decontamination

In one embodiment, compositions for decontamination and methods of using the same, are provided. In the case of a potential contamination of a surface or an area, such as a room, a composition comprising a lytic enzyme directed against *Bacillus anthracis* may be sprayed over the entire surface of the room, and can be sprayed on the surface of any air ducts leading into, and away from, the room. The carrier for the enzyme may have a pH in the range of from about 4.0 to about 12.0, with a more optimum range of from about 5.5 to about 7.5. Additionally, the carrier should be buffered. The enzyme may function the stabilizing buffer can have a pH range between about 4.0 and about 12.0, or even between about 5.5 and about 7.5.

The stabilizing buffer should allow for the optimum activity of the lysin enzyme. The buffer may contain a reducing reagent, such as dithiothreitol. The stabilizing buffer may also be or include a metal chelating reagent, such as ethylenediaminetetracetic acid disodium salt, or it may also contain a phosphate or citrate-phosphate buffer, or any other buffer. The concentration of the active units of enzyme believed to provide for an effective amount or dosage of enzyme may be in the range of about 100 units/ml to about 500,000 units/ml of fluid. In some cases, the range of the active units per ml of fluid may be much higher. Additionally, the carrier may also include (but is not limited to) a preservative, and an anti-bacterial agent to keep the carrier free of bacterial organisms.

In addition to using the lytic enzyme as described by a sequence shown in FIG. 1 (SEQ ID Nos.: 1-6), or polypeptide variants (including fragments) of SEQ ID NOs.: 1-6, and with the possible substitutional variants in the above listed table, there may also be, either in addition to or as a substitute for the lytic enzyme, chimeric and shuffled lytic enzymes.

The carrier may also include L-alanine, which may assist in the germination of any *Bacillus anthracis* spores present.

Due to the specificity of both enzymes for *B. anthracis*, their abilities to retain lytic activity under such a broad range of conditions, and an enhancement of killing activity when used together, it is proposed that PlyPH and PlyG may be applied for the decontamination of *B. anthracis* in the event of accidental or deliberate release. A mathematical model calculated the time required for decontamination after the release of 1.5 kilograms of anthrax spores in lower Manhattan (Wein, L. M., Y. Liu, and T. J. Leighton. 2005. HEPA/vaccine plan for indoor anthrax remediation. Emerging Infect. Dis. 11:69-76). Fumigation with chlorine dioxide gas, the method used in building decontamination after the 2001 mail attacks, would take an estimated 42 years before the buildings are deemed inhabitable. The same group proposed a combination of the fumigation technique and a HEPA filter/vacuuming/vaccination approach which would reduce the time taken for decontamination, but would still take at least 8 years. Here, the phage lysins PlyPH and PlyG are proposed to be used in conjunction with other decontamination methods to hasten the *B. anthracis* decontamination process. In preliminary experiments, an aqueous germinant in combination with PlyG resulted in a 3-log reduction in viability of *B. anthracis* spores. Being an aqueous solution, it avoids the corrosive effects of chlorine dioxide and related chemicals.

EXAMPLES

A bacteriophage lysin, PlyPH, with specific activity against *Bacillus anthracis* was identified and characterized in a series of exemplary embodiments described below. PlyPH is a prophage lysin that was originally identified in the *B. anthracis* Ames genome sequence and subsequently amplified from *B. anthracis* ΔSterne genomic DNA. More specifically, in the examples described below, the efficacy of PlyPH in killing *B. anthracis* and *B. anthracis*-like *B. cereus* was studied both in vitro and in vivo. The PlyPH lysin was cloned, purified and biochemically characterized, with its spectrum of activity examined against a range of bacterial species. The catalytic activity and binding affinity of the lysin were also investigated. The PlyPH *B. anthracis* phage lysin was also studied in combination with the phage lysin PlyG. PlyG was previously isolated from the γ phage and shown to have activity against *B. anthracis* (Schuch, R., D. Nelson, and V. A. Fischetti. 2002. A bacteriolytic agent that detects and kills *Bacillus anthracis*. Nature. 418:884-888).

For the examples described below, unless otherwise indicated, the following bacterial strains, plasmids and media were used.

Bacterial strains used:

Bacterial strains used:

| Bacterial strain | Source |
|---|---|
| *Escherichia coli* | |
| *Escherichia coli* XL1-Blue | 1 |
| *Escherichia coli* TOP10 | 2 |
| *Bacillus* | |
| *Bacillus anihracis* ΔSterne | 3 |
| *Bacillus cereus* ATCC4342 | 3 |
| *Bacillus cereus* ATCC10987 | 3 |
| *Bacillus cereus* 14579 | 3 |
| *Bacillus cereus* 13472 | 3 |
| *Bacillus cereus* T | 3 |
| *Bacillus thuringiensis* HD1 | 3 |
| *Bacillus thuringiensis* HD73 | 3 |
| *Bacillus subtilis* SL4 | 3 |
| *Bacillus pumilus* SL4680 | 3 |
| *Bacillus megaterium* RS77 | 3 |
| *BreviBacillus laterosporus* ATCC9141 | 3 |

1, Strategene, La Jolla CA; 2, Invitrogen, Carlsbad CA; 3, Raymond Schuch, Rockefeller University, New York NY.

In the work with *Bacillus* phage lysins, *B. cereus* strain ATCC4342 was used as a safe alternative to *B. anthracis*. *B. cereus* 4342 has been demonstrated to be closely related to *B. anthracis* strains by amplified fragment length polymorphism and multienzyme electrophoresis (Helgason, E., O. A. Okstad, D. A. Caugant, H. A. Johansen, A. Fouet, M. Mock, I. Hegna, and A.-B. Kolsto. 2000. *Bacillus anthracis, Bacillus cereus*, and *Bacillus thuringiensis*-one species on the basis of genetic evidence. Appl. Environ. Microbiol. 66:2627-2630; Ticknor, L. O., A.-B. Kolsto, K. K. Hill, P. Kein, M. T. Laker, M. Tonks, and P. J. Jackson. 2001. Fluorescent amplified fragment length polymorphism analysis of Norwegian *Bacillus cereus* and *Bacillus thuringiensis* soil isolates. Appl. Environ. Microbiol. 67:4863-4873). In addition, this strain also has qualities that are reflective of *B. anthracis*, rather than *B. cereus*. Like *B. anthracis, B. cereus* 4342 is non-motile, and it grows in long chains reminiscent of filaments on nutrient agar (Koehler, T. M. 2000. *Bacillus anthracis*., p. 519-528. In V. A. Fischetti, R. P. Novick, J. J. Ferretti, D. A. Portnoy, and J. I. Rood (ed.), Gram-positive pathogens. American Society for Microbiology, Washington, D.C.; Oncu, S., S. Oncu, and S. Sakarya. 2003. Anthrax—an overview. Med. Sci. Monit. 9:RA276-283; Swartz, M. N. 2001. Recognition and management of anthrax—an update. N. Eng. J. Med. 345:1621-1626; Turnbull, P. C. B. 2002. Introduction: anthrax history, disease and ecology. Curr. Top. Microbiol. Immunol. 271:1-19). It is also sensitive to the γ phage which is generally highly specific for *B. anthracis* (R. Schuch, personal communication).

Competent Bacterial Cells and DNA Transformation

Chemically competent *E. coli* were either purchased from commercial sources, or made competent in the laboratory using a calcium chloride method and transformed according to standard protocols (Sambrook, J., E. F. Fritsch, and T. Maniatis. 1989. Molecular cloning: a laboratory manual, 2nd ed. Cold Spring Harbor Laboratory Press, Cold Spring Harbor).

Plasmids

All plasmids were extracted from bacteria using QIAprep spin miniprep and maxi plasmid kits (Qiagen, Valencia Calif.). Unless otherwise indicated, plasmids generated in this work were constructed by polymerase chain reaction (PCR) amplification of a selected open reading frame (ORF) with primers harboring restriction sites on the 5' end. When possible, different restriction sites were used to achieve directional cloning. The digested PCR product and corresponding phosphatase treated (USB, Cleveland Ohio) plasmid vector were then ligated. Resulting plasmid clones were confirmed to be correct by DNA sequencing, restriction digest pattern and/or PCR.

Plasmids used and constructed in these experiments.

| Plasmid | Features | References |
|---|---|---|
| pBAD18 | Arabinose inducible cloning vector for *E. coli*, lacking a ribosome binding site | 1 |
| pBAD18-plyG | Inducible expression of PlyG | 2 |
| pBAD24 | Arabinose inducible cloning vector for *E. coli*, containing a ribosome binding site | 1 |
| pBAD24-BA2446 | Inducible expression of *B. anthracis* BA2446 | 3 |
| pBAD24-PlyPH | Inducible expression of *B. anthracis* PlyPH | 3 |
| pBAD24-BA3737 | Inducible expression of *B. anthracis* BA3737 | 3 |
| pBAD24-BA3767 | Inducible expression of *B. anthracis* BA3767 | 3 |
| pBAD24-BA4073 | Inducible expression of *B. anthracis* BA4073 | 3 |
| pBAD TOPO | Arabinose inducible TOPO cloning vector | 1 |

1, Invitrogen, Carlsbad CA;
2, Raymond Schuch, Rockefeller University, New York NY;
3, Pauline Yoong, Raymond Schuch, Daniel Nelson, Vincent Fischetti, Rockefeller University, New York NY.

Media

Luria-Bertani (LB) media was used for the growth of *E. coli* strains. BHI was used for growth of *Bacillus* strains. For solid medium, agar was added to 1.5%, while 0.75% was added to soft agar employed in overlays.

Where necessary, antibiotics were added to media for the selection and maintenance of plasmids. Ampicillin at 100 μg./mL was used in the selection of pBAD based vectors. For pBAD based vectors, protein expression was induced upon the addition of arabinose to 0.25%

Unless otherwise stated, molecular cloning enzymes were purchased from New England Biolabs (Beverly Mass.), and reagents from Sigma-Aldrich (St. Louis, Mo.).

Example 1

Identification and Cloning of Phage Lysins

Adapter Amplified Shotgun Expression Libraries (AASEL)

The LASL method was modified by Collin and Schuch and renamed adapter amplified shotgun expression libraries or AASEL. This new method involves the generation of a partial DNA digest using the restriction enzyme Tsp509I followed by its ligation to commercially available adapters with compatible EcoRI overhangs. Primers specific to the adapters were used for the amplification of the DNA library by PCR. Restriction digest and PCR conditions were optimized to obtain amplified DNA between the sizes of 0.5 and 3.5 kB. Upon completion of cloning the DNA library into pBAD TOPO and transformation into *E. coli* TOP10, DNA inserts from several clones were examined to ensure heterogeneity and that they were indeed within the desired size range.

Cloning of the Lysin Gene from *Bacillus* Phage ϕW2

The lysin encoding gene from ϕW2, a *Bacillus* phage isolated from a Pennsylvania soil sample, was cloned using this method. The phage genomic DNA library was permeabilized with chloroform vapor. Overlays of the *E. coli* library of ϕW2 DNA consisted of 200 μL of an overnight culture of *B. cereus* strain 4342 mixed with 6 mL of BHI soft agar. An estimated 8,000 colonies were screened. One positive clone was sent for DNA sequencing with the resulting sequence entered into the ORF Finder program within the NCBI website for the identification of putative ORFs.

Identification and Cloning of *B. Anthracis* Lysogenic Phage Lysins

Five putative lysogenic phage lysin open reading frames were selected for cloning by performing a BLAST search against four *B. anthracis* strains on the NCBI website using PlyG, the lysin from the *B. anthracis* gamma phage, as the query sequence. The *B. anthracis* genomes searched included the 'Ames Ancestor', Ames, A2012 and Steme strains. The ORFs selected were BA2446, PlyPH, BA3737, BA3767 and BA4073, nomenclature based on the *B. anthracis* Ames strain. Please note that although the names used for these ORFs correspond to the *B. anthracis* Ames strain, they were amplified by PCR using DNA from the attenuated *B. anthracis* ΔSterne strain. All ORFs were directionally cloned into pBAD24.

Example 2

Bacterial Lysis

Chloroform Extraction

This method was used to extract heterologous proteins expressed in *E. coli*. The bacterial culture was pelleted by centrifugation, and the resulting pellet washed with 50 mM potassium phosphate buffer at pH 7.4 or phosphate buffered saline (PBS). This wash step was repeated and the pellet suspended in phosphate buffer at 1/20 the original culture volume. Chloroform was added at 1/5 volume of the bacterial suspension and the mixture was rotated gently at room temperature for 1 hour. The mixture was centrifuged at 4,000 rpm, and the top layer containing the cell lysate was carefully removed.

Homogenization

Bacterial cultures were centrifuged and suspended in 1/20 volume of an appropriate buffer. The bacterial suspension was passaged through a high pressure homogenizer (EmulsiFlex®-05; Avestin Inc., Ottowa, Canada) above 15,000 pounds per square inch (psi) between 3 to 4 times to effectively lyse the cells. A centrifugation step at 7,000 rpm was required to remove the cell debris.

Examples 3A-3D

Assays for Phage Lysin Activity Against Bacteria

Example 3A

Overlay Method

The overlay method was outlined in the screening of phage genomic DNA libraries for lysins against *B. cereus* in previous sections. To summarize, this method entailed the spotting of *E. coli* clones on the surface of agar plates, growing these clones overnight, then exposure to chloroform vapor in order to permeabilize the cell membrane, followed by an overlay with the indicator bacterial strain. For the screening of lytic activity against *B. cereus*, the overlay consisted of 200 μL of an overnight culture of *B. cereus* strain 4342 mixed with 6 mL of BHI soft agar. These plates were incubated at room temperature during the day, and kept at 4° C. overnight.

Example 3B

Optical Density Assay of PlyPH Lytic Activity

For assays with the PlyPH lytic enzyme, *Bacillus* strains were grown at 30° C. for 3 hours, washed once in PBS and suspended in PBS at half the original culture volume. One hundred microliters of *B. cereus* suspension was mixed with 1004 of lysate containing PlyPH or purified PlyPH in a 96 well plate. $OD_{600}$ was read on a spectrophotometric plate reader (SpectraMax Plus384; Molecular Devices, Sunnyvale Calif.) every 15 to 30 seconds over a 15 minute to 1 hour time period to monitor any OD changes. Control reactions were set up in parallel containing PBS instead of lysin.

Example 3C

Viability Assay

*B. cereus* 4342 was grown as above. Bacterial suspensions and lysin were mixed together in a similar manner as the previous section. At the end of the incubation period, the reactions were serially diluted in PBS to $10^{-2}$, $10^{-4}$, $10^{-6}$ and $10^{-8}$ with 50 μL of each dilution plated on a quadrant of a BHI agar plate. Resulting viability counts were calculated from the number of colonies that arise following overnight incubation at 37° C.

Example 4

OD Quantitation of Lysin Activity

The quantitation of lysin activity is based on the OD assay method. The *B. cereus* indicator strain for the PlyPH enzyme was grown and washed as described, while the lysin sample to be quantified was serially diluted 2-fold with PBS. One hundred microliters of each bacterial suspension was added to an equal volume of each lysin dilution. The starting optical density of each bacterial suspension was typically 2.0. The optical density change of each reaction was monitored for 15 minutes. The lytic activity of lysins is expressed in units per milliliter, in which units represent the reciprocal of the highest dilution of enzyme resulting in a 50% reduction in bacterial $OD_{600}$ in 15 minutes.

Example 5

Determining the pH Profile of PlyPH Activity

Universal buffer was made up with equal parts of 40 mM boric acid and 40 mM phosphoric acid, followed by titration of the buffer from pH 2 to 12 with sodium hydroxide using a pH meter. At each pH point, 12 mL was removed. The pH of each sample was double checked using narrow range pH paper (Micro Essential Laboratory, Brooklyn N.Y.). To test the activity of PlyPH at different pH values, purified PlyPH, normally in 50 mM acetate buffer at pH 5.5, was dialyzed against the same buffer at 5 mM. Log phase *B. cereus* 4342 were washed and suspended in universal buffers at pH ranging from 2 to 12. One hundred eighty microliters of each *B. cereus* suspension was added to 20 μL of purified PlyPH at 40 units/mL. All reactions were incubated at room temperature for 15 minutes, followed by plating for viability counts. The final pH of each reaction was checked by pH paper. It is the final pH of the reaction that was recorded, not the pH of the buffer prior to addition of PlyPH.

Example 6

Analyzing Lysin Activities in Increasing Salt Concentrations

A 5M sodium chloride stock was added to *B. cereus* 4342-PlyPH assays to achieve final concentrations of NaCl up to 500 mM in each reaction. NaCl was added to 50, 200 and 500 mM in *B. cereus* 4342-PlyPH reactions, with the effects measured by a 15 minute viability assay.

Example 7

PlyPH Specificity Against *B. Cereus* 4342 in a Mixture of Bacteria by the Detection of ATP Release ATP release was indirectly measured as luminescence in relative light units (RLU) upon the addition of a solution of luciferin/luciferase to a mixture of the PlyPH enzyme and bacteria. ATP is released from bacteria upon lysis, while luciferin luminescence is dependent on luciferase and ATP. A PROFILE™-1 model 3550i microluminometer, with the PROFILE™-1 Reagent Kit was used for the measurement of luminescence (New Horizons Diagnostics Corporation, Columbia Md.). *B. cereus* 4342, *B. cereus* 14579, *B. thuringiensis* HD1 and *B. subtilis* SL4 were grown in BHI and washed with PBS as described above. Each bacterial suspension was diluted 1 in 500, with 50 μL applied to a Filtravette. The bacteria were washed twice with Somatic Cell Releasing Agent (SRA) according to manufacturer's instructions for the removal of somatic cells. Fifty microliters of PlyPH at 10 units./mL was added to the bacteria, followed by 50 μL of the luciferin/luciferase solution. Each reading was taken after 1 minute incubation. As a positive control, Bacterial Cell Releasing Agent (BRA) was added instead of the PlyPH enzyme. BRA is a non-specific bacterial lysis reagent that should lyse and release ATP from all bacterial samples indiscriminately. Each reaction and luminescent reading was carried out in duplicate.

Example 8

Effect of Serum on PlyPH and PlyG Activities

In these assays, preimmune and hyperimmune sera from rabbits before and after immunization with purified PlyG were used (Covance Research Products Inc., Denver Pa.). A Western blot of purified PlyPH enzyme using the hyperimmune sera from PlyG immunized rabbits was conducted. Two-fold dilutions of each serum sample were carried out in PBS. Fifty microliters of PlyPH or PlyG, both at 800 μg/mL protein or approximately 128 units./mL lytic activity, was added to 50 μL of each serum dilution. This mixture was preincubated for several minutes before the addition of a 100 μL suspension of *B. cereus* 4342 in PBS. All reactions were incubated at room temperature for 15 minutes, immediately followed by serial dilutions and plating for viability counts.

Monosaccharide Inhibition Assays of PlyPH Lytic Activity

N-acetylglucosamine, N-acetylmannosamine, galactose, glucosamine, glucose, mannosamine, mannose and xylose were tested either individually or in combination for inhibition of PlyPH lytic activity. The final concentration of each monosaccharide was at least 12.5 μg/mL, diluted from stock concentrations of 200 μL. Fifty microliters of PlyPH at 2.5 units/mL was incubated for several minutes with an equal volume of monosaccharide/s prior to the addition of a 100 μL *B. cereus* 4342 suspension. A reaction with PBS instead of monosaccharide served as a control. The reactions were incubated at room temperature for 15 minutes, and then plated on BHI agar for viability counts.

Effect of Cysteine Active Site Inhibitors and a Divalent Cation Chelator on Lysin Activities Cysteine active site inhibitors N-ethylmaleimide, iodoacetamide and sodium tetrathionate were added to lytic assays of PlyPH and *B. cereus* 4342 at a final concentration of 2 mM, while dithiopyridine was added at a final concentration of 30 μM due to low solubility. To duplicate reactions, dithiothreitol (DTT) was added to 8 mM, as N-ethylmaleimide is reversible by DTT. EDTA, a chelator of divalent cations, was used at 5 mM. Reactions were monitored by a 15 minute OD assay to determine if these compounds have an effect on PlyPH lytic activity.

Example 9

Purification of *B. Anthracis* Lysogenic Phage Lysins by Ion Exchange Chromatography The *B. anthracis* lytic enzymes BA2446, PlyPH and BA3767 have predicted isoelectric points (pl) of 5.85, 6.15 and 6.96 respectively. The expression of these enzymes from the pBAD24 expression vector was induced with the addition of arabinose for 4 hours at 37° C. The *E. coli* cultures were centrifuged at 7,000 rpm for 10 minutes. The bacterial pellets were suspended in 50 mM potassium phosphate buffer at pH 7.4 at 1/20 the original culture volume. All bacterial suspensions were lysed by homogenization. The purification of these proteins was initially attempted through a HiTrap Q FF 5 mL anion exchange column (Amersham Biosciences). The cell lysates were loaded onto the column, followed by washing with 50 mM potassium phosphate buffer at pH 7.4 until OD280 reached baseline. Proteins were eluted with a 20 column volume linear salt gradient of 50 mM potassium phosphate buffer at pH 7.4 containing up to 1M NaCl.

Subsequently, purification of the PlyPH and BA3767 enzymes were achieved through cation exchange chromatography on HiTrap SP HP columns. *E. coli* cultures were grown in the same manner as above. After the centrifugation step, the bacterial pellets were suspended in 50 mM acetate buffer at pH 5.5 instead of 50 mM potassium phosphate buffer at pH 7.4. The cell lysates were loaded onto the column, followed by washing with 50 mM acetate buffer at pH 5.5 until OD280 reached baseline. Proteins bound to the column were eluted with a 20 column volume linear salt gradient of 50 mM acetate buffer at pH 5.5 containing up to 1M NaCl.

Example 10

Mouse *B. Cereus* Peritonitis Model

All mice used were female BALB/c mice ranging between 5 to 8 weeks old (Charles River Laboratories, Inc., Wilmington Mass.). For these experiments, mice weighing an average of 16.5 grams were used. *B. cereus* 4342 was grown in BHI for 3 hours with aeration at 30° C., centrifuged and suspended in PBS to $OD_{600}$ of 0.75. One hundred microliters of this suspension was injected into the peritoneal cavity of each mouse. Ten minutes post infection, mice were either injected with 400 μL of purified PlyPH enzyme at an estimated 300 units/mL, or 400 μL of sterile 50 mM acetate buffer at pH 5.5. One hundred microliters of *B. cereus* suspension typically contained $2.5\times10^6$ CFU/mL. Mice were followed for 5 days and their clinical signs recorded.

Example 11

Electron Microscopy

*B. cereus* 4342 was grown in BHI broth for 3 hours at 30° C. with gyratory shaking. The bacterial culture was washed once in PBS at 1/20 the original culture volume. One hundred microliters of purified PlyPH enzyme at various concentrations were added to 100 μL of *B. cereus* 4342 suspension. PlyPH at 10, 40 and 100 units./mL were used. After 1 minute incubation, 200 μL of a 2× fixative solution was added to stop each reaction. This section transmission electron microscopy was carried out by Eleana Sphicas of the Rockefeller University Bio-Imaging Resource Center.

Example 12

Lytic Effect of PlyPH of Germinating *Bacillus cereus* 4342 Spores

Leighton-Doi Sporulation Media

Eight grams of nutrient broth mix and 16 g of agar were added to 900 mL of distilled water and autoclaved. Upon autoclaving, allow the mixture to cool by placing it in a 55° C. water bath for approximately 30 minutes. Meanwhile, stock solutions of 0.4 g manganese sulfate monohydrate ($MnSO_4.H_2O$) in 100 mL water, 5 g magnesium sulfate heptahydrate ($MgSO_4$ $7H2_O$) in 100 mL water and 0.06 g ferrous sulfate heptahydrate ($FeSO_4.7H_2O$) in 100 mL water were prepared. Also, a salt solution containing 3.8 g potassium chloride, 0.6 g calcium chloride and 1.8 g glucose in 200 mL of water was prepared, with 1 mL of the $MnSO_4.H_2O$, $MgSO_4.7H_2O$ and $FeSO_4.7H_2O$ stock solutions added. The salt solution was filter sterilized with 100 mL added to the 900 mL of cooled nutrient agar. The media was then poured into approximately 40 petri dishes to generate Leighton-Doi sporulation agar plates.

Sporulation of *B. Cereus* 4342 and Purification of Spores

One hundred microliters of an overnight culture of *B. cereus* 4342 was spread on each Leighton-Doi sporulation agar plate. Plates were incubated at 37° C. for 3 days. Each plate was flooded with 3 mL of ice cold distilled water, with the bacterial growth scraped off the agar surface and transferred into 50 mL centrifuge tubes. The bacterial suspensions were centrifuged at 10,000 rpm for 10 minutes. The spores appeared as a central white pellet, while contaminating vegetative bacilli and debris appeared as an off white outer rim surrounding the white central pellet. The contaminants were washed away by gentle pipetting of ice cold distilled water. The centrifugation and washing steps were repeated over 2 days for at least 5 times until only the white pellet remains.

Germination of Spores, Followed by Exposure to PlyPH Enzyme

One milliliter of a 1 in 10 diluted spore preparation was heat activated by incubation at 65° C. for 5 minutes, followed by centrifugation at 14,000 rpm for 1 minute. The pelleted, heat activated spores were suspended in 1 mL of germination media of BHI broth containing 100 mM L-alanine and 1 mM inosine. The suspension was incubated at 37° C. for 1 hour, centrifuged again as above and suspended in 1 mL PBS. Equal volumes of the germinating *B. cereus* 4342 spore suspension and purified PlyPH at 3 mg./mL were mixed. PBS was added to a control reaction instead of PlyPH. Both suspensions were incubated at 37° C., with aliquots removed every hour up to 5 hours for viability counts.

The above examples are illustrative only, and should not be interpreted as limiting since further modifications of the disclosed embodiments will be apparent to those skilled in the art in view of this teaching. All such modifications are deemed to be within the scope of the embodiments disclosed herein.

Example 13

Phage Lysins Binding Epitope Analyses

*B. cereus* RSVF1 was either treated with pronase to degrade all surface proteins, treated with sodium periodate to oxidize the surface carbohydrates, or left untreated. The diminished capacity for PlyPH to lyse periodate treated *B cersus* RSVF1, and untreated *B. cereus* RSVF1 in the presence of extracted RSVF1 surface carbohydrates suggests that PlyPH binds to a carbohydrate epitope. Table 2 below summarizes the results of *B. cereus* RSVF1 subjected to different treatments and the resulting ability for PlyPH to lyse the treated bacterial cells.

TABLE 2

| Sample | PlyPH dependent lysis? |
|---|---|
| Untreated *B. cereus* RSVF1 | YES |
| Pronase treated *B. cereus* RSVF1 | YES |
| Periodate treated *B. cereus* RSVF1 | NO |
| Un treated *B. cereus* RSVF1 + extracted RSVF1 surface carbohydrates | NO |

Extraction of Surface Carbohydrates from *B. Cereus* 4342

The surface carbohydrates of *B. cereus* 4342 were extracted using a nitrous acid extraction method. One liter of overnight grown bacteria was centrifuged, washed in PBS and suspended in 80 mL PBS. On a rotary shaker in the fume hood, 10 mL 4N sodium nitrite and 10 mL glacial acetic acid were added to the suspension and shaken vigorously for 15 minutes. The mixture was centrifuged at 7,000 g for 15 minutes to remove the bacterial cells. The supernatant containing the extracted carbohydrates was neutralized with sodium hydroxide and dialyzed at 4° C. overnight through a 1 kDa membrane against distilled water. The dialysate was lyophilized to obtain a crude dried carbohydrate preparation. This procedure was scaled up or down where necessary.

Estimating the Molecular Mass of BA2805 Specific *B. Cereus* 4342 Carbohydrate Epitope For an estimation of the molecular weight of the BA2805 enzyme inhibitory molecule or complex, the extracted surface carbohydrates were separated through a series of increasing molecular weight cutoff centrifuge concentrator units (Amicon Ultra; Millipore). Upon separation, the retentate and filtrate were tested for inhibition of lytic activity of the BA2805 enzyme. Carbohydrate inhibition assays were described in a previous section. Filter units with molecular weight cutoffs between 3 and 100 kDa were used.

Separation of *B. Cereus* 4342 Extracted Surface Carbohydrates Through a Gel Filtration Column A 100 μL solution of *B. cereus* 4342 crude surface carbohydrates at a concentration of 500 mg./mL was separated through a Superose™ 12 gel filtration column (Amersham Biosciences). Ammonium bicarbonate at 100 mM was used as the equilibration and elution buffer over 1.5 column volumes, with 0.75 mL fractions collected throughout. In an initial run, every other fraction was tested for inhibitory activity against the BA2805 enzyme. Carbohydrate inhibition assays were described in a previous section. All eluted fractions were pooled, dialyzed against distilled water and lyophilized. Lyophilization resulted in 2.5 mg of a fluffy white substance, which was dissolved in 100 μL sterile water. This solution was again tested for inhibition of BA2805 lytic activity. In a subsequent run, groups of 5 or more fractions were pooled and lyophilized. Each pooled sample was resuspended in 800 μL sterile water prior to testing for its inhibition of BA2805 lytic activity.

Purification of PlyG specific *B. cereus* 4342 Carbohydrate Epitope with a PlyG Affinity Column Approximately 9 mg of PlyG was conjugated to 1 g CNBR (cyanogen bromide)-activated Sepharose™ (Amersham Biosciences) as recommended by manufacturer's guidelines. Bicinchoninic acid assays to determine protein concentrations carried out before and after PlyG conjugation indicated that conjugation was successful. The manually packed column was washed in 50 mM Tris buffer at pH 6 prior to the application of the *B. cereus* 4342 carbohydrate suspension that was redialyzed against distilled water to remove any residual salt. The carbohydrate was incubated with the matrix with gentle rotation for 45 minutes. The column was washed with 50 mM Tris buffer at pH 6 to remove any unbound carbohydrate, while bound carbohydrate was eluted in a single step with the same buffer containing 1M NaCl. Fractions were collected at 1 mL each. Fractions from the wash of unbound carbohydrate were pooled, while fractions from the elution step were pooled. Both pools were concentrated by lyophilization and tested for inhibition of BA2805 lytic activity.

*B. Cereus* 4342 Cell Wall Extraction and Digestion with PlyG

Two liters of *B. cereus* 4342 was grown at 30° C. for 3 hours with gyratory shaking. The culture was centrifuged, suspended in 100 mL PBS and lysed by homogenization. The lysate was centrifuged at 1,000 rpm for 15 minutes to pellet any undigested bacteria. The supernatant was centrifuged at 6,000 rpm for 1 hour to pellet the cells walls. The cell walls were washed once with 50 mM Tris buffer at pH 6 containing 400 mM NaCl, and suspended in 1 mL of the same buffer. The cell wall suspension was sonicated briefly, followed by the addition of 2 mL PlyG at 3 mg./mL. The cell wall digest was incubated at 37° C. for 5 hours with gentle shaking, at which time another milliliter of PlyG was added and incubation proceeded overnight at 4° C. The digest was dialyzed against 50 mM Tris buffer at pH 8 through a 1 kDa cutoff membrane for 3 hours at 4° C. One microgram of trypsin was added into the dialysis tubing. Dialysis proceeded at room temperature for 6 hours, and continued overnight at 4° C. The digested cell walls were tested for inhibition of BA2805 lytic activity.

Separation of PlyG Digested Cell Walls of *B. Cereus* 4342 Through a Gel Filtration Column Two hundred microliters of ten-fold concentrated PlyG digested *B. cereus* 4342 cell walls were separated through a Superose™ 12 gel filtration column in a similar manner as the separation of surface carbohydrates in the preceding section. Every other fraction was tested for inhibition of BA2805 lytic activity. To rule out the possibility that trypsin was present in active peaks thereby inhibiting the lytic activity with its protease activity, inhibition assays were repeated in the presence of 1 μg./mL leupeptin, a trypsin inhibitor. Fractions 20 and 21, which showed inhibitory activity under all conditions, were lyophilized and sent for monosaccharide composition analysis by M-Scan Inc. (West Chester Pa.).

Pronase Treatment of *B. Cereus* 4342

*B. cereus* 4342 was grown in liquid media for two and a half hours, at which point the culture was divided into two. Pronase was added to one batch to a final concentration of 1 mg./mL, while PBS was added to the other at the same volume and the cultures were allowed to grow for an additional 30 minutes. Bacteria were then washed twice in PBS. *B. cereus* suspensions were assayed with purified BA2805 enzyme. All reactions were monitored by the OD assay for 15 minutes, followed by immediate plating for viability counts.

Periodate Treatment of *B. Cereus* 4342

*B. cereus* 4342 was grown in liquid media for 3 hours, centrifuged and suspended in PBS. The suspension was divided equally, and sodium periodate was added to one tube to a final concentration of 10 mM, while PBS was added to the other at the same volume. The reactions were incubated at room temperature for 10 minutes, followed by washing of bacterial cells twice with PBS. *B. cereus* suspensions were then assayed with the purified BA2805 enzyme. All reactions were monitored by the OD assay for 15 minutes.

---

We claim:

1. A composition comprising an isolated lysin polypeptide and one or more antimicrobial agent, anti-inflammatory agent, or mucoadhesive, wherein the polypeptide comprises the amino acid sequence set out in SEQ ID NO: 1 or an amino acid sequence that has at least 95% amino acid sequence identity to SEQ ID NO: 1, and wherein the polypeptide has killing activity against *B. anthracis* bacteria.

2. The composition of claim 1 comprising a polypeptide having an amino acid sequence set out in SEQ ID NO: 1.

3. The composition of claim 1 further comprising a pharmaceutically acceptable carrier or vehicle, or stabilizing buffer.

4. The composition of claim 3 formulated for administration to a subject orally, nasally, topically or parenterally.

5. The composition of claim 1 comprising one or more antibiotic.

6. The composition of claim 1 comprising a holin protein.

7. The composition of claim 1 wherein the polypeptide has killing activity against at least *B. cereus* 4342 and *B. anthracis* Sterne.

8. The composition of claim 1 wherein the polypeptide has in vivo killing activity against *B. cereus* RSVF1 at a pH of 4-12.

9. The composition of claim 1 wherein the polypeptide selectively kills *B. cereus* 4342 in the presence of one or more other *B. cereus, B. thuringiensis* or *B. subtilis* strains which are not killed.

10. A composition comprising an isolated polypeptide and one or more antimicrobial agent, anti-inflammatory agent, or mucoadhesive, wherein the polypeptide is a chimeric protein or fusion protein comprising the catalytic domain of the amino terminal portion or the binding domain of the carboxy terminal portion of the amino acid sequence set out in SEQ ID NO: 1, or an amino acid sequence that has at least 95% amino acid sequence identity to SEQ ID NO: 1 and has lytic or binding activity against *B. anthracis* bacteria.

11. The composition of claim 10 further comprising a pharmaceutically acceptable carrier or vehicle, or stabilizing buffer.

12. The composition of claim 10 formulated for administration to a subject orally, nasally, topically or parenterally.

13. The composition of claim 10 comprising one or more antibiotics.

14. A method of decontaminating a surface or area comprising contacting the surface or area with a composition comprising an isolated lysin polypeptide having killing activity against *B. anthracis* bacteria wherein the polypeptide comprises the amino acid sequence set out in SEQ ID NO: 1 or an amino acid sequence that has at least 95% amino acid sequence identity to SEQ ID NO: 1 and has killing activity against *B. anthracis* bacteria.

15. The method of claim 14 wherein the polypeptide has the amino acid sequence set out in SEQ ID NO: 1.

* * * * *